US011965884B2

(12) United States Patent
Dysinger et al.

(10) Patent No.: US 11,965,884 B2
(45) Date of Patent: Apr. 23, 2024

(54) METHOD OF QUANTITATING UNBOUND C5 IN A SAMPLE

(71) Applicant: Alexion Pharmaceuticals, Inc., Boston, MA (US)

(72) Inventors: Mark Dysinger, Killingworth, CT (US); Mark Ma, Madison, CT (US); Bruce A. Andrien, Guilford, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 1202 days.

(21) Appl. No.: 16/342,245

(22) PCT Filed: Oct. 19, 2017

(86) PCT No.: PCT/US2017/057372
§ 371 (c)(1),
(2) Date: Apr. 16, 2019

(87) PCT Pub. No.: WO2018/075758
PCT Pub. Date: Apr. 26, 2018

(65) Prior Publication Data
US 2019/0250157 A1  Aug. 15, 2019

Related U.S. Application Data

(60) Provisional application No. 62/410,009, filed on Oct. 19, 2016.

(51) Int. Cl.
*G01N 33/543*  (2006.01)

(52) U.S. Cl.
CPC .  *G01N 33/54393* (2013.01); *G01N 33/54313* (2013.01); *G01N 33/54353* (2013.01); *G01N 2333/4716* (2013.01)

(58) Field of Classification Search
None
See application file for complete search history.

(56) References Cited

U.S. PATENT DOCUMENTS

| 6,319,469 B1 * | 11/2001 | Mian | B01L 3/50273 422/63 |
|---|---|---|---|
| 2002/0015957 A1 * | 2/2002 | Hageman | A61P 37/02 351/200 |
| 2003/0175267 A1 * | 9/2003 | Wang | A61P 29/00 530/389.3 |
| 2006/0067935 A1 | 3/2006 | Ambati | |
| 2010/0173793 A1 | 7/2010 | Dilly et al. | |
| 2011/0014182 A1 * | 1/2011 | Alard | A61P 27/12 514/17.8 |
| 2014/0056878 A1 * | 2/2014 | McConnell | C07K 16/18 435/328 |
| 2016/0263126 A1 * | 9/2016 | Kulikowski | A61P 7/10 |
| 2016/0266136 A1 * | 9/2016 | Cochran | G01N 33/574 |
| 2019/0242893 A1 * | 8/2019 | Dysinger | G01N 33/54366 |

FOREIGN PATENT DOCUMENTS

| CA | 2797856 | * | 4/2011 | ............. C07K 16/18 |
|---|---|---|---|---|
| EP | 0097440 A1 | | 1/1984 | |
| JP | S595958 B2 | | 2/1984 | |
| JP | 2010-151738 A | | 7/2010 | |
| JP | 2016-520542 A | | 7/2016 | |
| WO | WO 2005072380 | * | 8/2005 | |
| WO | 2008/140483 A2 | | 11/2008 | |
| WO | 2011/137395 A1 | | 11/2011 | |
| WO | WO 2012088247 | * | 12/2011 | ........... A61K 39/395 |
| WO | 2012/045451 A1 | | 4/2012 | |
| WO | WO 2015021166 | * | 8/2014 | ............. G01N 33/68 |
| WO | 2014/160958 A1 | | 10/2014 | |
| WO | 2016/151558 A1 | | 9/2016 | |
| WO | 2018/075758 A1 | | 4/2018 | |
| WO | 2018/075761 A1 | | 4/2018 | |

OTHER PUBLICATIONS

U.S. Appl. No. 16/342,217, filed Apr. 16, 2019, Mark Dysinger.
International Preliminary Report on Patentability, PCT/US2017/057372, dated Apr. 23, 2019, 9 pages.
International Search Report and Written Opinion, PCT/US2017/057372, dated Mar. 23, 2018, 15 pages.
Thermo Scientific et al: "ELISA technical guide and protocols Table of Contents," Jan. 25, 2010, Retrieved from the Internet: URL:https://tools.thermofisher.com/content/sfs/brochures/TR0065-ELISA-guide.pdf [retrieved on Jan. 10, 2018.
Thermo Scientific et al.: "ELISA technical guide and protocols," Jan. 25, 2010, Retrieved from the Internet: URL: https://tools.thermofisher.com/content/sfs/brochures/TR0065-ELISA-guide.pdf [retrieved on Jan. 10, 2018.
Given, A. et al., "Development and validation of an alpha fetoprotein immunoassay using Gyros technology," Journal Of Pharmaceutical and Biomedical Analysis, vol. 64-65, May 1, 2012, pp. 8-15.
Haukanes, B-I et al., "Application of Magnetic Beads in Bioassays," Biotechnology. The International Monthly for Industrial Biology, Nature Publishing Group, US, vol. 11 (11):60-63 (1993).
Hudlikar, M. et al., "Controlled Multi-functionalization Facilitates Targeted Delivery of Nanoparticles to Cancer Cells," Chemistry, vol. 22(4): 1415-1423 (2016).
International Preliminary Report on Patentability, PCT/US2017/057377, dated Apr. 29, 2019, 7 pages.
International Search Report and Written Opinion, PCT/US2017/057377, dated Jan. 31, 2019, 11 pages.

(Continued)

*Primary Examiner* — Ann Montgomery
(74) *Attorney, Agent, or Firm* — Nelson Mullins Riley & Scarborough LLP; Jane E. Remillard, Esq.; Jill Gorny Sloper, Esq.

(57) ABSTRACT

A method of quantitating free (unbound) human C5 complement protein (C5) from a sample comprising: binding biotinylated anti-C5 capture antibody to strepavidin-coated particles; capturing the free (unbound) C5 in the sample; detecting the captured free C5; and quantitating the captured free C5 using laser-induced fluorescence detection; wherein the method is performed in a Gyros Bioaffy 200 CD in a Gyrolab xPlore or a Gyrolab XP instrument.

9 Claims, 6 Drawing Sheets

Specification includes a Sequence Listing.

(56) References Cited

OTHER PUBLICATIONS

Mora, J. et al., "Application of the Gyrolab(TM) platform to ligand-binding assays: a user's perspective," Bioanalysis, vol. 2 (10):1711-1715 (Oct. 1, 2010).

Scalia, G. et al., "Lifetime of fluorescent dye molecules in dense aqueous suspensions of polystyrene nanoparticles," Opt Express, vol. 23(23):29342-52 (2015).

Zhang, S. et al., "Visualizing Dengue Virus through Alexa Fluor Labeling," JoVE, vol. 53, 4 pages (2011).

Cai, H. et al., "Automation of ELISAs & evaluation of emerging technologies for high throughout quantitation of protein impurities," Pharmaceutical Bioprocessing, vol. 3(7): 427-441 (2015).

Genetic News, New Tools Aim to Reduce Turnaround Times in Biotherapeutic Development and Production, 8 pages (2011).

Given, A. et al., "Development and validation of an alpha fetoprotein immunoassay using Gyros technology," Journal of Pharmaceutical and Biomedical Analysis, vol. 64-65:8-15 (2012).

Heo, J. et al., "A microfluidic approach to high throughput quantification of host cell protein impurities for bioprocess development," Pharm. Bioprocess, vol. 2(2):129-139 (2014).

Leary, B. et al., "Bioanalytical platform comparison using a generic human IgG PK assay format," Journal of Immunological Methods, vol. 397: 28-36 (2013).

Patel, V. et al., "Automating bioanalytical sample analysis through enhanced system integration," Bioanalysis, vol. 5 (13):1649-1659 (2013).

Press Release, Gyros Protein Technologies Introduces the Gyrolab xPand New platform aims to improve immunoassay workflow, flexibility, and speed in biotherapeutic discovery, development, and production UPPSALA, Sweden, Mar. 19, 2018, 2 pages.

* cited by examiner

| Identity | Conc | X dilution | % Recovery |
|---|---|---|---|
| 01-025 | 67.7 | 67.7 | NA |
| 01-050 | 38.2 | 76.4 | 112.9 |
| 01-100 | 15.9 | 63.7 | 94.2 |
| 01-200 | 7.4 | 59.3 | 87.7 |
| 02-025 | 109.2 | 109.2 | NA |
| 02-050 | 49.2 | 98.4 | 90.1 |
| 02-100 | 21.3 | 85.3 | 78.1 |
| 02-200 | 13.1 | 104.6 | 95.8 |
| 04-025 | 71.4 | 71.4 | NA |
| 04-050 | 38.7 | 77.4 | 108.4 |
| 04-100 | 18.6 | 74.2 | 103.9 |
| 04-200 | 7.4 | 59.5 | 83.3 |
| 05-025 | 63.0 | 63.0 | NA |
| 05-050 | 23.4 | 46.8 | 74.3 |
| 05-100 | 10.9 | 43.4 | 68.9 |
| 05-200 | 4.7 | 37.8 | 60.0 |
| 06-025 | 83.2 | 83.2 | NA |
| 06-050 | 36.4 | 72.9 | 87.6 |
| 06-100 | 18.1 | 72.4 | 87.0 |
| 06-200 | 9.7 | 77.6 | 93.2 |
| 07-025 | 64.3 | 64.3 | NA |
| 07-050 | 27.8 | 55.5 | 86.3 |
| 07-100 | 15.1 | 60.6 | 94.2 |
| 07-200 | 8.5 | 68.0 | 105.8 |
| 08-025 | 55.0 | 55.0 | NA |
| 08-050 | 30.5 | 60.9 | 110.6 |
| 08-100 | 14.4 | 57.7 | 104.8 |
| 08-200 | 7.3 | 58.3 | 105.9 |

FIG. 3

| Identity | Expected Conc | Mean Measured Conc | CV Conc | S/B | % Bias |
|---|---|---|---|---|---|
| LLOQ1 | 0.005 | 0.0086 | 5.9 | 3.7 | 71.7 |
| LLOQ2 | 0.015 | 0.0129 | 15.7 | 5.0 | -14.2 |
| LQC | 0.045 | 0.0413 | 4.3 | 12.0 | -8.2 |
| MQC | 10 | 9.35 | 0.2 | 2036.0 | -6.5 |
| HQC | 240 | 227.0 | 1.2 | 15804.1 | -5.4 |
| ULOQ | 300 | 286.7 | 3.9 | 17141.9 | -4.4 |
| LLOQ1 | 0.005 | BLQ | NA | 2.6 | NA |
| LLOQ2 | 0.015 | 0.0163 | 10.9 | 5.8 | 8.5 |
| LQC | 0.045 | 0.0458 | 0.0 | 12.8 | 1.7 |
| MQC | 10 | 9.29 | 0.4 | 2031.2 | -7.1 |
| HQC | 240 | 223.4 | 2.9 | 15629.7 | -6.9 |
| ULOQ | 300 | 255.4 | 8.2 | 16220.4 | -14.9 |
| LLOQ1 | 0.005 | 0.0070 | 10.9 | 3.4 | 39.5 |
| LLOQ2 | 0.015 | 0.0163 | 7.8 | 5.8 | 8.5 |
| LQC | 0.045 | 0.0465 | 5.4 | 13.4 | 3.3 |
| MQC | 10 | 8.93 | 4.8 | 1898.8 | -10.7 |
| HQC | 240 | 244.8 | 4.9 | 16538.2 | 2.0 |
| ULOQ | 300 | 272.8 | 9.0 | 16594.0 | -9.1 |

FIG. 4A

| QC Level | Expected µg/mL | Mean Measured µg/mL | Std Dev | %CV | %Recovery |
|---|---|---|---|---|---|
| ULOQ | 300 | 271.8 | 16.390 | 6.0 | 90.6 |
| HQC | 240 | 235.5 | 9.032 | 3.8 | 98.1 |
| MQC | 10 | 8.61 | 0.656 | 7.6 | 86.1 |
| LQC | 0.045 | 0.0391 | 0.006 | 15.9 | 87.0 |
| LLOQ | 0.015 | 0.0152 | 0.003 | 17.1 | 101.5 |

FIG. 4B

| Sample | Mean Unspiked (Endogenous) | CV% | Mean Spiked | CV% | Corrected (Blk Endog + Spiked Conc) Conc | % Bias |
|---|---|---|---|---|---|---|
| SEL01 | 48.3 | 4.1 | 108.9 | 8.9 | 98.3 | 10.8 |
| SEL02 | 151.9 | 4.4 | 205.8 | 4.0 | 201.9 | 1.9 |
| SEL03 | 56.3 | 3.2 | 111.3 | 7.4 | 106.3 | 4.8 |
| SEL04 | 140.2 | 10.3 | 194.8 | 1.1 | 190.2 | 2.4 |
| SEL05 | 96.3 | 3.0 | 180.5 | 8.9 | 146.3 | 23.4 |
| SEL06 | 136.4 | 9.5 | 178.2 | 3.9 | 186.4 | -4.4 |
| SEL07 | 143.8 | 4.2 | 207.3 | 2.4 | 193.8 | 7.0 |
| SEL08 | 95.4 | 1.5 | 164.3 | 1.5 | 145.4 | 13.0 |
| SEL09 | 149.9 | 5.7 | 209.7 | 2.7 | 199.9 | 4.9 |
| SEL10 | 110.6 | 0.3 | 167.5 | 4.1 | 160.6 | 4.3 |
| Spike Control | 51.6 | 2.2 | - | - | - | - |

| UNKNOWNS | | | | | | | | | | |
|---|---|---|---|---|---|---|---|---|---|---|
| IDENTITY | RESPONSE | S/B | CALC CONC [ ] | AVERAGE CONC [ ] | CV CONC [%] | AVERAGE RESPONSE | CV RESPONSE [%] | DILUTION | CD ID | CD STRUCT |
| LLOQ01 | 0.076 | 2.285 | 0.014 | 0.014 | 1.746 | 0.078 | 1.936 | 1.000 | 0003475-321 | A2 |
| LLOQ01 | 0.079 | 2.348 | 0.015 | 0.014 | 1.746 | 0.078 | 1.936 | 1.000 | 0003475-321 | F44 |
| LLOQ02 | 0.080 | 2.388 | 0.015 | 0.015 | 3.449 | 0.079 | 1.694 | 1.000 | 0003475-321 | A4 |
| LLOQ02 | 0.078 | 2.332 | 0.014 | 0.015 | 3.449 | 0.079 | 1.694 | 1.000 | 0003475-321 | F46 |
| LLOQ03 | 0.081 | 2.429 | 0.015 | 0.015 | 5.112 | 0.080 | 2.791 | 1.000 | 0003475-321 | A5 |
| LLOQ03 | 0.078 | 2.335 | 0.014 | 0.015 | 5.112 | 0.080 | 2.791 | 1.000 | 0003475-321 | F47 |
| LLOQ04 | 0.081 | 2.418 | 0.015 | 0.015 | 3.289 | 0.082 | 1.157 | 1.000 | 0003475-321 | A7 |
| LLOQ04 | 0.082 | 2.458 | 0.016 | 0.015 | 3.289 | 0.082 | 1.157 | 1.000 | 0003475-321 | G49 |
| LLOQ05 | 0.070 | 2.098 | 0.012 | 0.013 | 4.041 | 0.071 | 1.871 | 1.000 | 0003475-321 | B9 |
| LLOQ05 | 0.072 | 2.154 | 0.013 | 0.013 | 4.041 | 0.071 | 1.871 | 1.000 | 0003475-321 | G51 |
| LLOQ06 | 0.078 | 2.339 | 0.014 | 0.015 | 3.449 | 0.079 | 0.937 | 1.000 | 0003475-321 | B11 |
| LLOQ06 | 0.079 | 2.370 | 0.015 | 0.015 | 3.449 | 0.079 | 0.937 | 1.000 | 0003475-321 | G53 |
| LLOQ07 | 0.076 | 2.277 | 0.014 | 0.013 | 11.785 | 0.072 | 7.761 | 1.000 | 0003475-321 | B12 |
| LLOQ07 | 0.068 | 2.040 | 0.012 | 0.013 | 11.785 | 0.072 | 7.761 | 1.000 | 0003475-321 | G54 |
| LLOQ08 | 0.082 | 2.438 | 0.015 | 0.015 | 5.112 | 0.079 | 4.223 | 1.000 | 0003475-321 | B14 |
| LLOQ08 | 0.077 | 2.297 | 0.014 | 0.015 | 5.112 | 0.079 | 4.223 | 1.000 | 0003475-321 | G56 |
| ULOQ01 | 250.802 | 7494.278 | 265.606 | 269.462 | 2.024 | 252.054 | 0.702 | 1.000 | 0003475-321 | B16 |
| ULOQ01 | 253.305 | 7569.071 | 273.318 | 269.462 | 2.024 | 252.054 | 0.702 | 1.000 | 0003475-321 | H58 |
| ULOQ02 | 253.987 | 7569.450 | 275.461 | 282.144 | 3.350 | 256.053 | 1.141 | 1.000 | 0003475-321 | C18 |
| ULOQ02 | 258.118 | 7712.889 | 288.827 | 282.144 | 3.350 | 256.053 | 1.141 | 1.000 | 0003475-321 | H60 |
| ULOQ03 | 250.725 | 7491.977 | 265.372 | 280.658 | 7.703 | 255.480 | 2.632 | 1.000 | 0003475-321 | C19 |
| ULOQ03 | 260.235 | 7776.148 | 295.944 | 280.658 | 7.703 | 255.480 | 2.632 | 1.000 | 0003475-321 | H61 |
| ULOQ04 | 260.987 | 7798.618 | 298.518 | 285.722 | 6.333 | 257.084 | 2.147 | 1.000 | 0003475-321 | C21 |
| ULOQ04 | 253.180 | 7565.335 | 272.927 | 285.722 | 6.333 | 257.084 | 2.147 | 1.000 | 0003475-321 | H63 |
| ULOQ05 | 258.776 | 7732.551 | 291.019 | 272.882 | 9.399 | 252.960 | 3.252 | 1.000 | 0003475-321 | C23 |
| ULOQ05 | 247.144 | 7384.972 | 254.746 | 272.882 | 9.399 | 252.960 | 3.252 | 1.000 | 0003475-321 | I65 |
| ULOQ06 | 244.744 | 7313.257 | 247.876 | 266.671 | 9.968 | 250.922 | 3.482 | 1.000 | 0003475-321 | D25 |
| ULOQ06 | 257.099 | 7682.440 | 285.466 | 266.671 | 9.968 | 250.922 | 3.482 | 1.000 | 0003475-321 | I67 |
| ULOQ07 | 252.312 | 7539.398 | 270.230 | 278.886 | 4.389 | 255.021 | 1.502 | 1.000 | 0003475-321 | D26 |
| ULOQ07 | 257.730 | 7701.295 | 287.542 | 278.886 | 4.389 | 255.021 | 1.502 | 1.000 | 0003475-321 | I68 |
| ULOQ08 | 253.215 | 7566.381 | 273.037 | 277.918 | 2.484 | 254.748 | 0.851 | 1.000 | 0003475-321 | D28 |
| ULOQ08 | 256.281 | 7657.997 | 282.799 | 277.918 | 2.484 | 254.748 | 0.851 | 1.000 | 0003475-321 | I70 |
| LLOQ09 | 0.087 | 2.002 | 0.017 | 0.016 | 9.428 | 0.084 | 5.927 | 1.000 | 0003475-321 | D30 |

FIG. 6

| Parameter | MPI ECL Assay (1210 Coat) | Alexion/CRO Gyros Assay |
|---|---|---|
| Status | Validated | Pre-validation |
| Dynamic Range | 0.0274 - 20.0 | 0.015 - 300 µg/mL |
| MRD | 20 (Pre), 2 (Post) | 30 |
| Assay Time | ~ 3.5 Hours | ~ 65 Minutes |
| Parallelism | No | Yes |
| Linearity | To 320 | To 15625 |
| Selectivity | Yes | Yes |
| Carryover | NA | None |

FIG. 7

SEQUENCE LISTING

<160> NUMBER OF SEQ ID NOS: 33

<210> SEQ ID NO 1
<211> LENGTH: 741
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: CDS
<222> LOCATION: (1)..(738)

<400> SEQUENCE: 1

| | | | | | | | | | | | | | | | | |
|---|---|---|---|---|---|---|---|---|---|---|---|---|---|---|---|---|
| gat | atc | cag | atg | acc | cag | tcc | ccg | tcc | tcc | ctg | tcc | gcc | tct | gtg | ggc | 48 |
| Asp | Ile | Gln | Met | Thr | Gln | Ser | Pro | Ser | Ser | Leu | Ser | Ala | Ser | Val | Gly | |
| 1 | | | | 5 | | | | | 10 | | | | | 15 | | |

| gat | agg | gtc | acc | atc | acc | tgc | ggc | gcc | agc | gaa | aac | atc | tat | ggc | gcg | 96 |
|---|---|---|---|---|---|---|---|---|---|---|---|---|---|---|---|---|
| Asp | Arg | Val | Thr | Ile | Thr | Cys | Gly | Ala | Ser | Glu | Asn | Ile | Tyr | Gly | Ala | |
| | | | 20 | | | | | 25 | | | | | 30 | | | |

| ctg | aac | tgg | tat | caa | cag | aaa | ccc | ggg | aaa | gct | ccg | aag | ctt | ctg | att | 144 |
|---|---|---|---|---|---|---|---|---|---|---|---|---|---|---|---|---|
| Leu | Asn | Trp | Tyr | Gln | Gln | Lys | Pro | Gly | Lys | Ala | Pro | Lys | Leu | Leu | Ile | |
| | | | 35 | | | | | 40 | | | | | 45 | | | |

| tac | ggt | gcg | acg | aac | ctg | gca | gat | gga | gtc | cct | tct | cgc | ttc | tct | gga | 192 |
|---|---|---|---|---|---|---|---|---|---|---|---|---|---|---|---|---|
| Tyr | Gly | Ala | Thr | Asn | Leu | Ala | Asp | Gly | Val | Pro | Ser | Arg | Phe | Ser | Gly | |
| | 50 | | | | | 55 | | | | | 60 | | | | | |

| tcc | ggc | tcc | gga | acg | gat | ttc | act | ctg | acc | atc | agc | agt | ctg | cag | cct | 240 |
|---|---|---|---|---|---|---|---|---|---|---|---|---|---|---|---|---|
| Ser | Gly | Ser | Gly | Thr | Asp | Phe | Thr | Leu | Thr | Ile | Ser | Ser | Leu | Gln | Pro | |
| 65 | | | | | 70 | | | | | 75 | | | | | 80 | |

| gaa | gac | ttc | gct | acg | tat | tac | tgt | cag | aac | gtt | tta | aat | act | ccg | ttg | 288 |
|---|---|---|---|---|---|---|---|---|---|---|---|---|---|---|---|---|
| Glu | Asp | Phe | Ala | Thr | Tyr | Tyr | Cys | Gln | Asn | Val | Leu | Asn | Thr | Pro | Leu | |
| | | | | 85 | | | | | 90 | | | | | 95 | | |

| act | ttc | gga | cag | ggt | acc | aag | gtg | gaa | ata | aaa | cgt | act | ggc | ggt | ggt | 336 |
|---|---|---|---|---|---|---|---|---|---|---|---|---|---|---|---|---|
| Thr | Phe | Gly | Gln | Gly | Thr | Lys | Val | Glu | Ile | Lys | Arg | Thr | Gly | Gly | Gly | |
| | | | 100 | | | | | 105 | | | | | 110 | | | |

| ggt | tct | ggt | ggc | ggt | gga | tct | ggt | ggt | ggc | ggt | tct | caa | gtc | caa | ctg | 384 |
|---|---|---|---|---|---|---|---|---|---|---|---|---|---|---|---|---|
| Gly | Ser | Gly | Gly | Gly | Gly | Ser | Gly | Gly | Gly | Gly | Ser | Gln | Val | Gln | Leu | |
| | | 115 | | | | | 120 | | | | | 125 | | | | |

| gtg | caa | tcc | ggc | gcc | gag | gtc | aag | aag | cca | ggg | gcc | tca | gtc | aaa | gtg | 432 |
|---|---|---|---|---|---|---|---|---|---|---|---|---|---|---|---|---|
| Val | Gln | Ser | Gly | Ala | Glu | Val | Lys | Lys | Pro | Gly | Ala | Ser | Val | Lys | Val | |
| | 130 | | | | | 135 | | | | | 140 | | | | | |

| tcc | tgt | aaa | gct | agc | ggc | tat | att | ttt | tct | aat | tat | tgg | att | caa | tgg | 480 |
|---|---|---|---|---|---|---|---|---|---|---|---|---|---|---|---|---|
| Ser | Cys | Lys | Ala | Ser | Gly | Tyr | Ile | Phe | Ser | Asn | Tyr | Trp | Ile | Gln | Trp | |
| 145 | | | | | 150 | | | | | 155 | | | | | 160 | |

| gtg | cgt | cag | gcc | ccc | ggg | cag | ggc | ctg | gaa | tgg | atg | ggt | gag | atc | tta | 528 |
|---|---|---|---|---|---|---|---|---|---|---|---|---|---|---|---|---|
| Val | Arg | Gln | Ala | Pro | Gly | Gln | Gly | Leu | Glu | Trp | Met | Gly | Glu | Ile | Leu | |
| | | | | 165 | | | | | 170 | | | | | 175 | | |

| ccg | ggc | tct | ggt | agc | acc | gaa | tat | acc | gaa | aat | ttt | aaa | gac | cgt | gtt | 576 |
|---|---|---|---|---|---|---|---|---|---|---|---|---|---|---|---|---|
| Pro | Gly | Ser | Gly | Ser | Thr | Glu | Tyr | Thr | Glu | Asn | Phe | Lys | Asp | Arg | Val | |
| | | | 180 | | | | | 185 | | | | | 190 | | | |

| act | atg | acg | cgt | gac | act | tcg | act | agt | aca | gta | tac | atg | gag | ctc | tcc | 624 |
|---|---|---|---|---|---|---|---|---|---|---|---|---|---|---|---|---|
| Thr | Met | Thr | Arg | Asp | Thr | Ser | Thr | Ser | Thr | Val | Tyr | Met | Glu | Leu | Ser | |
| | | 195 | | | | | 200 | | | | | 205 | | | | |

| agc | ctg | cga | tcg | gag | gac | acg | gcc | gtc | tat | tat | tgc | gcg | cgt | tat | ttt | 672 |
|---|---|---|---|---|---|---|---|---|---|---|---|---|---|---|---|---|
| Ser | Leu | Arg | Ser | Glu | Asp | Thr | Ala | Val | Tyr | Tyr | Cys | Ala | Arg | Tyr | Phe | |
| | 210 | | | | | 215 | | | | | 220 | | | | | |

| ttt | ggt | tct | agc | ccg | aat | tgg | tat | ttt | gat | gtt | tgg | ggt | caa | gga | acc | 720 |
|---|---|---|---|---|---|---|---|---|---|---|---|---|---|---|---|---|
| Phe | Gly | Ser | Ser | Pro | Asn | Trp | Tyr | Phe | Asp | Val | Trp | Gly | Gln | Gly | Thr | |
| 225 | | | | | 230 | | | | | 235 | | | | | 240 | |

```
ctg gtc act gtc tcg agc tga                                    741
Leu Val Thr Val Ser Ser
                245
```

<210> SEQ ID NO 2
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Gly Gly Gly
            100                 105                 110

Gly Ser Gly Gly Gly Gly Ser Gly Gly Gly Gly Ser Gln Val Gln Leu
        115                 120                 125

Val Gln Ser Gly Ala Glu Val Lys Lys Pro Gly Ala Ser Val Lys Val
    130                 135                 140

Ser Cys Lys Ala Ser Gly Tyr Ile Phe Ser Asn Tyr Trp Ile Gln Trp
145                 150                 155                 160

Val Arg Gln Ala Pro Gly Gln Gly Leu Glu Trp Met Gly Glu Ile Leu
                165                 170                 175

Pro Gly Ser Gly Ser Thr Glu Tyr Thr Glu Asn Phe Lys Asp Arg Val
            180                 185                 190

Thr Met Thr Arg Asp Thr Ser Thr Ser Thr Val Tyr Met Glu Leu Ser
        195                 200                 205

Ser Leu Arg Ser Glu Asp Thr Ala Val Tyr Tyr Cys Ala Arg Tyr Phe
    210                 215                 220

Phe Gly Ser Ser Pro Asn Trp Tyr Phe Asp Val Trp Gly Gln Gly Thr
225                 230                 235                 240

Leu Val Thr Val Ser Ser
                245
```

<210> SEQ ID NO 3
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

```
Gly Gly Gly Gly Ser Gly Gly Gly Gly Ser Gly Gly Gly Gly Ser
1               5                   10                  15
```

```
<210> SEQ ID NO 4
<211> LENGTH: 1676
<212> TYPE: PRT
<213> ORGANISM: Homo sapiens

<400> SEQUENCE: 4

Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
            20                  25                  30

Val Gly Ala Ser Glu Asn Ile Val Ile Gln Val Tyr Gly Tyr Thr Glu
        35                  40                  45

Ala Phe Asp Ala Thr Ile Ser Ile Lys Ser Tyr Pro Asp Lys Lys Phe
    50                  55                  60

Ser Tyr Ser Ser Gly His Val His Leu Ser Ser Glu Asn Lys Phe Gln
65                  70                  75                  80

Asn Ser Ala Ile Leu Thr Ile Gln Pro Lys Gln Leu Pro Gly Gly Gln
                85                  90                  95

Asn Pro Val Ser Tyr Val Tyr Leu Glu Val Val Ser Lys His Phe Ser
            100                 105                 110

Lys Ser Lys Arg Met Pro Ile Thr Tyr Asp Asn Gly Phe Leu Phe Ile
        115                 120                 125

His Thr Asp Lys Pro Val Tyr Thr Pro Asp Gln Ser Val Lys Val Arg
    130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Val Asp Met Val Glu Glu
                165                 170                 175

Ile Asp His Ile Gly Ile Ile Ser Phe Pro Asp Phe Lys Ile Pro Ser
            180                 185                 190

Asn Pro Arg Tyr Gly Met Trp Thr Ile Lys Ala Lys Tyr Lys Glu Asp
        195                 200                 205

Phe Ser Thr Thr Gly Thr Ala Tyr Phe Glu Val Lys Glu Tyr Val Leu
    210                 215                 220

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
                245                 250                 255

Asn Lys Val Val Thr Glu Ala Asp Val Tyr Ile Thr Phe Gly Ile Arg
            260                 265                 270

Glu Asp Leu Lys Asp Asp Gln Lys Glu Met Met Gln Thr Ala Met Gln
        275                 280                 285

Asn Thr Met Leu Ile Asn Gly Ile Ala Gln Val Thr Phe Asp Ser Glu
    290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
                325                 330                 335

Ser Glu Glu Ala Glu Ile Pro Gly Ile Lys Tyr Val Leu Ser Pro Tyr
            340                 345                 350

Lys Leu Asn Leu Val Ala Thr Pro Leu Phe Leu Lys Pro Gly Ile Pro
        355                 360                 365

Tyr Pro Ile Lys Val Gln Val Lys Asp Ser Leu Asp Gln Leu Val Gly
    370                 375                 380
```

```
Gly Val Pro Val Ile Leu Asn Ala Gln Thr Ile Asp Val Asn Gln Glu
385                 390                 395                 400

Thr Ser Asp Leu Asp Pro Ser Lys Ser Val Thr Arg Val Asp Asp Gly
            405                 410                 415

Val Ala Ser Phe Val Leu Asn Leu Pro Ser Gly Val Thr Val Leu Glu
            420                 425                 430

Phe Asn Val Lys Thr Asp Ala Pro Asp Leu Pro Glu Glu Asn Gln Ala
            435                 440                 445

Arg Glu Gly Tyr Arg Ala Ile Ala Tyr Ser Ser Leu Ser Gln Ser Tyr
        450                 455                 460

Leu Tyr Ile Asp Trp Thr Asp Asn His Lys Ala Leu Leu Val Gly Glu
465                 470                 475                 480

His Leu Asn Ile Ile Val Thr Pro Lys Ser Pro Tyr Ile Asp Lys Ile
                485                 490                 495

Thr His Tyr Asn Tyr Leu Ile Leu Ser Lys Gly Lys Ile Ile His Phe
            500                 505                 510

Gly Thr Arg Glu Lys Phe Ser Asp Ala Ser Tyr Gln Ser Ile Asn Ile
        515                 520                 525

Pro Val Thr Gln Asn Met Val Pro Ser Ser Arg Leu Leu Val Tyr Tyr
    530                 535                 540

Ile Val Thr Gly Glu Gln Thr Ala Glu Leu Val Ser Asp Ser Val Trp
545                 550                 555                 560

Leu Asn Ile Glu Glu Lys Cys Gly Asn Gln Leu Gln Val His Leu Ser
                565                 570                 575

Pro Asp Ala Asp Ala Tyr Ser Pro Gly Gln Thr Val Ser Leu Asn Met
            580                 585                 590

Ala Thr Gly Met Asp Ser Trp Val Ala Leu Ala Ala Val Asp Ser Ala
        595                 600                 605

Val Tyr Gly Val Gln Arg Gly Ala Lys Lys Pro Leu Glu Arg Val Phe
    610                 615                 620

Gln Phe Leu Glu Lys Ser Asp Leu Gly Cys Gly Ala Gly Gly Gly Leu
625                 630                 635                 640

Asn Asn Ala Asn Val Phe His Leu Ala Gly Leu Thr Phe Leu Thr Asn
                645                 650                 655

Ala Asn Ala Asp Asp Ser Gln Glu Asn Asp Glu Pro Cys Lys Glu Ile
            660                 665                 670

Leu Arg Pro Arg Arg Thr Leu Gln Lys Lys Ile Glu Glu Ile Ala Ala
        675                 680                 685

Lys Tyr Lys His Ser Val Val Lys Lys Cys Cys Tyr Asp Gly Ala Cys
    690                 695                 700

Val Asn Asn Asp Glu Thr Cys Glu Gln Arg Ala Ala Arg Ile Ser Leu
705                 710                 715                 720

Gly Pro Arg Cys Ile Lys Ala Phe Thr Glu Cys Cys Val Val Ala Ser
                725                 730                 735

Gln Leu Arg Ala Asn Ile Ser His Lys Asp Met Gln Leu Gly Arg Leu
            740                 745                 750

His Met Lys Thr Leu Leu Pro Val Ser Lys Pro Glu Ile Arg Ser Tyr
        755                 760                 765

Phe Pro Glu Ser Trp Leu Trp Glu Val His Leu Val Pro Arg Arg Lys
    770                 775                 780

Gln Leu Gln Phe Ala Leu Pro Asp Ser Leu Thr Thr Trp Glu Ile Gln
785                 790                 795                 800
```

-continued

```
Gly Ile Gly Ile Ser Asn Thr Gly Ile Cys Val Ala Asp Thr Val Lys
            805                 810                 815

Ala Lys Val Phe Lys Asp Val Phe Leu Glu Met Asn Ile Pro Tyr Ser
        820                 825                 830

Val Val Arg Gly Glu Gln Ile Gln Leu Lys Gly Thr Val Tyr Asn Tyr
        835                 840                 845

Arg Thr Ser Gly Met Gln Phe Cys Val Lys Met Ser Ala Val Glu Gly
    850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Gly Ser Ser His Leu Val
            885                 890                 895

Thr Phe Thr Val Leu Pro Leu Glu Ile Gly Leu His Asn Ile Asn Phe
        900                 905                 910

Ser Leu Glu Thr Trp Phe Gly Lys Glu Ile Leu Val Lys Thr Leu Arg
        915                 920                 925

Val Val Pro Glu Gly Val Lys Arg Glu Ser Tyr Ser Gly Val Thr Leu
    930                 935                 940

Asp Pro Arg Gly Ile Tyr Gly Thr Ile Ser Arg Arg Lys Glu Phe Pro
945                 950                 955                 960

Tyr Arg Ile Pro Leu Asp Leu Val Pro Lys Thr Glu Ile Lys Arg Ile
            965                 970                 975

Leu Ser Val Lys Gly Leu Leu Val Gly Glu Ile Leu Ser Ala Val Leu
        980                 985                 990

Ser Gln Glu Gly Ile Asn Ile Leu  Thr His Leu Pro Lys  Gly Ser Ala
        995                 1000                1005

Glu Ala  Glu Leu Met Ser Val  Val Pro Val Phe Tyr  Val Phe His
    1010                1015                1020

Tyr Leu  Glu Thr Gly Asn His  Trp Asn Ile Phe His  Ser Asp Pro
    1025                1030                1035

Leu Ile  Glu Lys Gln Lys Leu  Lys Lys Lys Leu Lys  Glu Gly Met
    1040                1045                1050

Leu Ser  Ile Met Ser Tyr Arg  Asn Ala Asp Tyr Ser  Tyr Ser Val
    1055                1060                1065

Trp Lys  Gly Gly Ser Ala Ser  Thr Trp Leu Thr Ala  Phe Ala Leu
    1070                1075                1080

Arg Val  Leu Gly Gln Val Asn  Lys Tyr Val Glu Gln  Asn Gln Asn
    1085                1090                1095

Ser Ile  Cys Asn Ser Leu Leu  Trp Leu Val Glu Asn  Tyr Gln Leu
    1100                1105                1110

Asp Asn  Gly Ser Phe Lys Glu  Asn Ser Gln Tyr Gln  Pro Ile Lys
    1115                1120                1125

Leu Gln  Gly Thr Leu Pro Val  Glu Ala Arg Glu Asn  Ser Leu Tyr
    1130                1135                1140

Leu Thr  Ala Phe Thr Val Ile  Gly Ile Arg Lys Ala  Phe Asp Ile
    1145                1150                1155

Cys Pro  Leu Val Lys Ile Asp  Thr Ala Leu Ile Lys  Ala Asp Asn
    1160                1165                1170

Phe Leu  Leu Glu Asn Thr Leu  Pro Ala Gln Ser Thr  Phe Thr Leu
    1175                1180                1185

Ala Ile  Ser Ala Tyr Ala Leu  Ser Leu Gly Asp Lys  Thr His Pro
    1190                1195                1200
```

```
Gln Phe Arg Ser Ile Val Ser Ala Leu Lys Arg Glu Ala Leu Val
1205                1210                1215

Lys Gly Asn Pro Pro Ile Tyr Arg Phe Trp Lys Asp Asn Leu Gln
1220                1225                1230

His Lys Asp Ser Ser Val Pro Asn Thr Gly Thr Ala Arg Met Val
1235                1240                1245

Glu Thr Thr Ala Tyr Ala Leu Leu Thr Ser Leu Asn Leu Lys Asp
1250                1255                1260

Ile Asn Tyr Val Asn Pro Val Ile Lys Trp Leu Ser Glu Glu Gln
1265                1270                1275

Arg Tyr Gly Gly Gly Phe Tyr Ser Thr Gln Asp Thr Ile Asn Ala
1280                1285                1290

Ile Glu Gly Leu Thr Glu Tyr Ser Leu Leu Val Lys Gln Leu Arg
1295                1300                1305

Leu Ser Met Asp Ile Asp Val Ser Tyr Lys His Lys Gly Ala Leu
1310                1315                1320

His Asn Tyr Lys Met Thr Asp Lys Asn Phe Leu Gly Arg Pro Val
1325                1330                1335

Glu Val Leu Leu Asn Asp Asp Leu Ile Val Ser Thr Gly Phe Gly
1340                1345                1350

Ser Gly Leu Ala Thr Val His Val Thr Thr Val His Lys Thr
1355                1360                1365

Ser Thr Ser Glu Glu Val Cys Ser Phe Tyr Leu Lys Ile Asp Thr
1370                1375                1380

Gln Asp Ile Glu Ala Ser His Tyr Arg Gly Tyr Gly Asn Ser Asp
1385                1390                1395

Tyr Lys Arg Ile Val Ala Cys Ala Ser Tyr Lys Pro Ser Arg Glu
1400                1405                1410

Glu Ser Ser Ser Gly Ser Ser His Ala Val Met Asp Ile Ser Leu
1415                1420                1425

Pro Thr Gly Ile Ser Ala Asn Glu Glu Asp Leu Lys Ala Leu Val
1430                1435                1440

Glu Gly Val Asp Gln Leu Phe Thr Asp Tyr Gln Ile Lys Asp Gly
1445                1450                1455

His Val Ile Leu Gln Leu Asn Ser Ile Pro Ser Asp Phe Leu
1460                1465                1470

Cys Val Arg Phe Arg Ile Phe Glu Leu Phe Glu Val Gly Phe Leu
1475                1480                1485

Ser Pro Ala Thr Phe Thr Val Tyr Glu Tyr His Arg Pro Asp Lys
1490                1495                1500

Gln Cys Thr Met Phe Tyr Ser Thr Ser Asn Ile Lys Ile Gln Lys
1505                1510                1515

Val Cys Glu Gly Ala Ala Cys Lys Cys Val Glu Ala Asp Cys Gly
1520                1525                1530

Gln Met Gln Glu Glu Leu Asp Leu Thr Ile Ser Ala Glu Thr Arg
1535                1540                1545

Lys Gln Thr Ala Cys Lys Pro Glu Ile Ala Tyr Ala Tyr Lys Val
1550                1555                1560

Ser Ile Thr Ser Ile Thr Val Glu Asn Val Phe Val Lys Tyr Lys
1565                1570                1575

Ala Thr Leu Leu Asp Ile Tyr Lys Thr Gly Glu Ala Val Ala Glu
1580                1585                1590
```

```
Lys Asp Ser Glu Ile Thr Phe Ile Lys Lys Val Thr Cys Thr Asn
    1595                1600                1605

Ala Glu Leu Val Lys Gly Arg Gln Tyr Leu Ile Met Gly Lys Glu
1610                1615                1620

Ala Leu Gln Ile Lys Tyr Asn Phe Ser Phe Arg Tyr Ile Tyr Pro
1625                1630                1635

Leu Asp Ser Leu Thr Trp Ile Glu Tyr Trp Pro Arg Asp Thr Thr
1640                1645                1650

Cys Ser Ser Cys Gln Ala Phe Leu Ala Asn Leu Asp Glu Phe Ala
1655                1660                1665

Glu Asp Ile Phe Leu Asn Gly Cys
1670                1675

<210> SEQ ID NO 5
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 6
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 7
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285
```

```
Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Leu His Glu Ala
            420                 425                 430

Leu His Ser His Tyr Thr Gln Lys Ser Leu Ser Leu Ser Leu Gly Lys
            435                 440                 445

<210> SEQ ID NO 8
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Tyr Ile Phe Ser Asn Tyr Trp Ile Gln
1               5                   10

<210> SEQ ID NO 10
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Glu Ile Leu Pro Gly Ser Gly Ser Thr Glu Tyr Thr Glu Asn Phe Lys
1               5                   10                  15

Asp

<210> SEQ ID NO 11
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Tyr Phe Phe Gly Ser Ser Pro Asn Trp Tyr Phe Asp Val
1               5                   10

<210> SEQ ID NO 12
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Ala Ser Glu Asn Ile Tyr Gly Ala Leu Asn
1               5                   10

<210> SEQ ID NO 13
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 13

Gly Ala Thr Asn Leu Ala Asp
1               5

<210> SEQ ID NO 14
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gln Asn Val Leu Asn Thr Pro Leu Thr
1               5

<210> SEQ ID NO 15
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser
        115                 120

<210> SEQ ID NO 16
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Asn Val Leu Asn Thr Pro Leu
                 85                  90                  95

Thr Phe Gly Gln Gly Thr Lys Val Glu Ile Lys
            100                 105
```

<210> SEQ ID NO 17
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

```
Gly Gly Gly Gly Ser Gly Gly Gly Gly Ser
1               5                   10
```

<210> SEQ ID NO 18
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

```
Gly Gly Gly Gly Ser Gly Gly Gly Gly Ser Gly Gly Gly Gly Ser
1               5                   10                  15
```

<210> SEQ ID NO 19
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

```
Gly Gly Gly Ser Gly Gly Gly Ser Gly Gly Gly Ser Gly Gly Gly Ser
1               5                   10                  15
```

<210> SEQ ID NO 20
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

```
Gly Gly Gly Ser
1
```

<210> SEQ ID NO 21
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 21

Ser Gly Gly Gly Gly
1               5

<210> SEQ ID NO 22
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Ser Gly Gly Gly Gly Ser Gly Gly Gly Gly
1               5                   10

<210> SEQ ID NO 23
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240
```

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 24
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser
        115                 120

<210> SEQ ID NO 25
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

```
Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
             85                  90                  95

Thr Val Glu Arg Lys Cys Cys Val Glu Cys Pro Pro Cys Pro Ala Pro
        100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Leu His Glu Ala Leu His Ser His Tyr Thr Gln Lys Ser Leu
305                 310                 315                 320

Ser Leu Ser Leu Gly Lys
            325

<210> SEQ ID NO 26
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Ser Ser Asn Phe Gly Thr Gln Thr
 65                  70                  75                  80
```

```
Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Tyr Ile Thr Arg Glu Pro Glu Val Thr Cys Val Val Val Asp
130             135                 140

Val Ser His Glu Asp Pro Glu Val Gln Phe Asn Trp Tyr Val Asp Gly
145             150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Glu Met Thr Lys Asn
225             230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305             310                 315                 320

Ser Leu Ser Pro Gly Lys
                325

<210> SEQ ID NO 27
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
                20                  25                  30

Trp Ile Gln Trp Val Arg Gln Ala Pro Gly Gln Gly Leu Glu Trp Met
            35                  40                  45

Gly Glu Ile Leu Pro Gly Ser Gly Ser Thr Glu Tyr Thr Glu Asn Phe
        50                  55                  60

Lys Asp Arg Val Thr Met Thr Arg Asp Thr Ser Thr Ser Thr Val Tyr
65              70                  75                  80

Met Glu Leu Ser Ser Leu Arg Ser Glu Asp Thr Ala Val Tyr Tyr Cys
                85                  90                  95
```

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Thr Ser Ser Asn Phe Gly Thr Gln Thr Tyr Thr Cys Asn Val Asp
    195                 200                 205

His Lys Pro Ser Asn Thr Lys Val Asp Lys Thr Val Glu Arg Lys Cys
        210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Tyr Ile Thr Arg
            245                 250                 255

Glu Pro Glu Val Thr Cys Val Val Val Asp Val Ser His Glu Asp Pro
        260                 265                 270

Glu Val Gln Phe Asn Trp Tyr Val Asp Gly Met Glu Val His Asn Ala
    275                 280                 285

Lys Thr Lys Pro Arg Glu Glu Gln Phe Asn Ser Thr Phe Arg Val Val
        290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
            325                 330                 335

Ile Ser Lys Thr Lys Gly Gln Pro Arg Glu Pro Gln Val Tyr Thr Leu
        340                 345                 350

Pro Pro Ser Arg Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

<210> SEQ ID NO 28
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

```
<400> SEQUENCE: 28

Gly Ala Ser Glu Asn Ile Tyr His Ala Leu Asn
1               5                   10

<210> SEQ ID NO 29
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Glu Ile Leu Pro Gly Ser Gly His Thr Glu Tyr Thr Glu Asn Phe Lys
1               5                   10                  15
Asp

<210> SEQ ID NO 30
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Asp Tyr Lys Asp Asp Asp Asp Lys
1               5

<210> SEQ ID NO 31
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 31

His His His His His His
1               5

<210> SEQ ID NO 32
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Tyr Pro Tyr Asp Val Pro Asp Tyr Ala
1               5

<210> SEQ ID NO 33
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 33

Gly His Ile Phe Ser Asn Tyr Trp Ile Gln
1               5                   10
```

METHOD OF QUANTITATING UNBOUND C5 IN A SAMPLE

RELATED APPLICATIONS

This application is a 35 U.S.C. 371 national stage filing of International Application No. PCT/US2017/057372, filed on Oct. 19, 2017, which claims priority from U.S. Provisional Application No. 62/410,009, filed on Oct. 19, 2016. The contents of these applications are incorporated herein by reference in their entireties.

SEQUENCE LISTING

The instant application contains a Sequence Listing which has been submitted electronically in ASCII format and is hereby incorporated by reference in its entirety. Said ASCII copy, created on Apr. 16, 2019 is named AXJ_263US_SEQ.txt and is 54413 bytes in size.

TECHNICAL FIELD

This invention relates to the field of immunologically related diseases and assays for quantifying free (unbound) drug target.

BACKGROUND

Complement protein C5 is an important component of the complement cascade, and a target of drugs, such as eculizumab and ALXN1210. Proper quantification of this target is essential for monitoring disease state, modeling, dosage selection, label claims, etc. Many ligand binding assay formats using drug as a capture reagent for free target are inherently flawed in that during sample incubation, the capture reagent can set up a dynamic equilibrium with target that is already bound to drug in matrix. Due to this equilibrium, it is possible for the assay to overestimate the amount of free target in matrix, thus leading to potentially inaccurate modeling, dosage selection, filing data, and label claims.

A common strategy for overcoming this overestimation in ligand binding assays is to abbreviate sample incubation time, thus reducing the opportunity for capture reagent to pull bound target from drug in matrix. To accomplish this, it is often necessary to increase the coating reagent concentration by as much as 5 times, which can in essence minimize the effects of the shortened sample incubation. Also, pretreatment samples tend to have much higher levels of free target than post treatment samples, often requiring different sample dilutions for each situation.

SUMMARY

This disclosure provides a method of quantitating free (unbound) human C5 complement protein (C5) from a sample comprising:
  a. binding biotinylated anti-C5 capture antibody to strepavidin-coated particles; wherein said biotinylated anti-C5 capture antibody is added by capillary action to a Gyros Bioaffy 200 CD comprising columns with the strepavidin-coated particles; wherein said CD is subjected to centrifugal force inside a Gyrolab xPlore or a Gyrolab XP instrument, thus driving the biotinylated anti-C5 capture antibody to the strepavidin-coated particles in the columns;
  b. capturing the free (unbound) C5 in the sample; wherein the sample is added to the CD by capillary action; wherein said CD is subjected to centrifugal force inside the Gyrolab xPlore or a Gyrolab XP instrument, thus driving the sample to the biotinylated anti-C5 capture antibody bound to the strepavidin-coated particles in the columns;
  c. detecting the captured free C5; wherein an AlexaFluor labeled anti-C5 detection antibody is added to the CD by capillary action, wherein said anti-C5 detection antibody binds C5 at a different epitope from the epitope bound by the capture antibody; wherein said CD is subjected to centrifugal force inside the Gyrolab xPlore or a Gyrolab XP instrument, thus driving the detection antibody to the free C5 bound to the capture antibody bound to the strepavidin-coated particles in the columns; and
  d. quantitating the captured free C5 using laser-induced fluorescence detection.

Without limiting the disclosure, a number of embodiments of the disclosure are described below for purpose of illustration.

Item 1. A method of quantitating free (unbound) human C5 complement protein (C5) from a sample comprising: a. binding biotinylated anti-C5 capture antibody to strepavidin-coated Meso Scale Discovery® (MSD®) 96-well assay plate; b. capturing the free (unbound) C5 in the sample by adding the sample to the plate; c. detecting the captured free C5 by adding sulfo-tagged anti-C5 detection antibody to the plate; and d. quantitating the captured free C5 using electrochemiluminescence; wherein the sample is diluted by about 1:2; wherein the sample is kept on ice; wherein steps b.-c. are about 15 to 30 minutes, and wherein the biotinylated capture anti-C5 antibody is added at a concentration of about 5 µg/mL.

Item 2. A method of quantitating free (unbound) human C5 complement protein (C5) from a sample comprising: a. binding biotinylated anti-C5 capture antibody to strepavidin-coated particles; wherein said biotinylated anti-C5 capture antibody is added by capillary action to a Gyros Bioaffy 200 CD comprising columns with the strepavidin-coated particles; wherein said CD is subjected to centrifugal force inside a Gyrolab xPlore or a Gyrolab XP instrument, thus driving the biotinylated anti-C5 capture antibody to the strepavidin-coated particles in the columns; b. capturing the free (unbound) C5 in the sample; wherein the sample is added to the CD by capillary action; wherein said CD is subjected to centrifugal force inside the Gyrolab xPlore or a Gyrolab XP instrument, thus driving the sample to the biotinylated anti-C5 capture antibody bound to the strepavidin-coated particles in the columns; c. detecting the captured free C5; wherein an AlexaFluor labeled anti-C5 detection antibody is added to the CD by capillary action, wherein said anti-C5 detection antibody binds C5 at a different epitope from the epitope bound by the capture antibody; wherein said CD is subjected to centrifugal force inside the Gyrolab xPlore or a Gyrolab XP instrument, thus driving the detection antibody to the free C5 bound to the capture antibody bound to the strepavidin-coated particles in the columns; and d. quantitating the captured free C5 using laser-induced fluorescence detection.

Item 3. The method of item 1, further comprising calculating the concentration or amount of free C5 antibody by comparing the data obtained from step d. to a standard curve prepared from known amounts of C5 added to a C5 depleted sample using the method of item 1.

Item 4. The method of item 2, further comprising calculating the concentration or amount of free C5 antibody by comparing the data obtained from step d. to a standard curve prepared from known amounts of C5 added to a C5 depleted sample using the method of item 2.

Item 5. The method of item 3, further comprising calculating the concentration of free C5 antibody with the Gyros Evaluator software.

Item 6. The method of any one of the preceding items, wherein the sample is obtained from a human patient.

Item 7. The method of item 6, wherein said sample is a serum sample or a plasma sample.

Item 8. The method of any one of the preceding items, wherein the patient has been treated with an anti-C5 antibody.

Item 9. The method of item 8, wherein the patient has been treated with eculizumab.

Item 10. The method of item 8, wherein the patient has been treated with ALXN1210.

Item 11. The method of any one of the preceding items, wherein the biotinylated capture antibody is eculizumab or ALXN1210.

Item 12. The method of any one of the preceding items, wherein the detection anti-C5 antibody is N19-8 (mouse anti-human C5 antibody).

Item 13. The method of item 2, wherein Rexxip A buffer is used for diluting samples and Rexxip F buffer is used for diluting the detection antibody.

Item 14. The method of item 2, further comprising priming the Gyros instrument two separate times with Bioaffy wash 1 and pH 11 buffer.

Item 15. The method of item 2, wherein the sample is a human serum sample from a patient, wherein the free C5 of the patient's pre-treatment and post-treatment with an anti-C5 antibody serum samples are quantitated, and wherein both the pre-treatment and the post-treatment sample is diluted to the same dilution.

Item 16. The method of item 15, wherein the both the pre-treatment and the post-treatment sample is diluted by a 1:20 to a 1:30 dilution.

Numerous other aspects are provided in accordance with these and other aspects of the invention. Other features and aspects of the present invention will become more fully apparent from the following detailed description and the appended claims.

BRIEF DESCRIPTION OF THE DRAWINGS

FIG. 3 shows parallelism of 7 individual donor sera.

Early Contract Research Organization (CRO) assay transfer results are shown in FIG. 4A and FIG. 4B

FIG. 6 shows that no carryover in a carryover assessment.

FIG. 7 shows a summary comparison.

DETAILED DESCRIPTION

Figure 1:
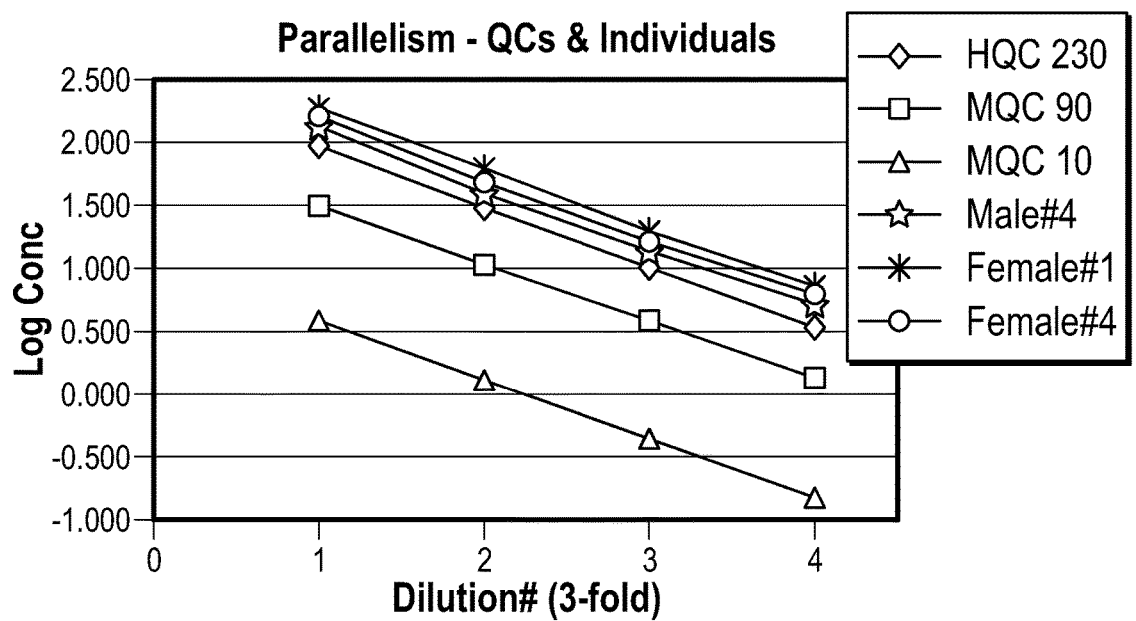
FIG. 1 is a graph showing parallelism.

As used herein, the word "a" or "plurality" before a noun represents one or more of the particular noun. For example, the phrase "a mammalian cell" represents "one or more mammalian cells."

The term "mammalian cell" is known in the art and can refer to any cell from or derived from any mammal including, for example, a human, a hamster, a mouse, a green monkey, a rat, a pig, a cow, a hamster, or a rabbit. In some embodiments, the mammalian cell can be an immortalized cell, a differentiated cell, an undifferentiated cell, a stem cell, etc.

As used herein, the terms "subject" and "patient" are used interchangeably. A patient or a subject can be a human patient or a human subject.

The term "recombinant protein" is known in the art. Briefly, the term "recombinant protein" can refer to a protein that can be manufactured using a cell culture system. The cells in the cell culture system can be derived from, for example, a mammalian cell, including a human cell, an insect cell, a yeast cell, or a bacterial cell. In general, the cells in the cell culture contain an introduced nucleic acid encoding the recombinant protein of interest (which nucleic acid can be borne on a vector, such as a plasmid vector). The nucleic acid encoding the recombinant protein can also contain a heterologous promoter operably linked to a nucleic acid encoding the protein.

The term "immunoglobulin" is known in the art. Briefly, the term "immunoglobulin" can refer to a polypeptide containing an amino acid sequence of at least 15 amino acids (e.g., at least 20, 30, 40, 50, 60, 70, 80, 90, or 100 amino acids, or more than 100 amino acids) of an immunoglobulin protein (e.g., a variable domain sequence, a framework sequence, or a constant domain sequence). The immunoglobulin can, for example, include at least 15 amino acids of a light chain immunoglobulin, e.g., at least 15 amino acids of a heavy chain immunoglobulin, such as a CDRH3. The immunoglobulin may be an isolated antibody (e.g., an IgG, IgE, IgD, IgA, or IgM). The immunoglobulin may be a subclass of IgG (e.g., IgG1, IgG2, IgG3, or IgG4). The immunoglobulin can be an antibody fragment, e.g., a Fab fragment, a F(ab')$_2$ fragment, or a scFv. The immunoglobulin can also be an engineered protein containing at least one immunoglobulin domain (e.g., a fusion protein). The engineered protein or immunoglobulin-like protein can also be a bi-specific antibody or a tri-specific antibody, or a dimer, trimer, or multimer antibody, or a diabody, a DVD-Ig, a CODV-Ig, an Affibody®, or a Nanobody®. Non-limiting examples of immunoglobulins are described herein and additional examples of immunoglobulins are known in the art.

The term "engineered protein" is known in the art. Briefly, the term "engineered protein" can refer to a polypeptide that is not naturally encoded by an endogenous nucleic acid present within an organism (e.g., a mammal). Examples of engineered proteins include modified enzymes with one or more amino acid substitutions, deletions, insertions, or additions that result in an increase in stability and/or catalytic activity of the engineered enzyme, fusion proteins, humanized antibodies, chimeric antibodies, divalent antibodies, trivalent antibodies, four binding domain antibodies, a diabody, and antigen-binding proteins that contain at least one recombinant scaffolding sequence.

The terms "polypeptide," "peptide," and "protein" are used interchangeably and are known in the art and can mean any peptide-bond linked chain of amino acids, regardless of length or post-translational modification.

The term "antibody" is known in the art. The term "antibody" may be used interchangeably with the term "immunoglobulin." Briefly, it can refer to a whole antibody comprising two light chain polypeptides and two heavy chain polypeptides. Whole antibodies include different antibody isotypes including IgM, IgG, IgA, IgD, and IgE antibodies. The term "antibody" includes, for example, a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified or a recombinant antibody.

The antibody can also be an engineered protein or antibody-like protein containing at least one immunoglobulin domain (e.g., a fusion protein). The engineered protein or antibody-like protein can also be a bi-specific antibody or a tri-specific antibody, or a dimer, trimer, or multimer antibody, or a diabody, a DVD-Ig, a CODV-Ig, an Affibody®, or a Nanobody®.

The term "antibody fragment," "antigen-binding fragment," or similar terms are known in the art and can, for example, refer to a fragment of an antibody that retains the ability to bind to a target antigen (e.g., human C5) and inhibit the activity of the target antigen. Such fragments include, e.g., a single chain antibody, a single chain Fv fragment (scFv), an Fd fragment, a Fab fragment, a Fab' fragment, or an F(ab')2 fragment. A scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein. See, e.g., Todorovska et al. (2001) *J Immunol Methods* 248(1):47-66; Hudson and Kortt (1999) *J Immunol Methods* 231(1):177-189; Poljak (1994) *Structure* 2(12):1121-1123; Rondon and Marasco (1997) *Annual Review of Microbiology* 51:257-283. An antigen-binding fragment can also include the variable region of a heavy chain polypeptide and the variable region of a light chain polypeptide. An antigen-binding fragment can thus comprise the CDRs of the light chain and heavy chain polypeptide of an antibody.

The term "antibody fragment" also can include, e.g., single domain antibodies such as camelized single domain antibodies. See, e.g., Muyldermans et al. (2001) *Trends Biochem Sci* 26:230-235; Nuttall et al. (2000) *Curr Pharm Biotech* 1:253-263; Reichmann et al. (1999) *J Immunol Meth* 231:25-38; PCT application publication nos. WO 94/04678 and WO 94/25591; and U.S. Pat. No. 6,005,079. The term "antibody fragment" also includes single domain antibodies comprising two $V_H$ domains with modifications such that single domain antibodies are formed.

The term "antibody" also includes "antigen-binding fragment" and "antibody fragment."

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The Complement System

As is well known, the complement system acts in conjunction with other immunological systems of the body to defend against intrusion of cellular and viral pathogens. There are at least 25 complement proteins. Complement components achieve their immune defensive functions by interacting in a series of intricate but precise enzymatic cleavage and membrane binding events. The resulting complement cascade leads to the production of products with opsonic, immunoregulatory, and lytic functions.

The complement cascade can progress via the classical pathway ("CP"), the lectin pathway ("LP"), or the alternative pathway ("AP"). The lectin pathway is typically initiated with binding of mannose-binding lectin ("MBL") to high mannose substrates. The AP can be antibody independent, and can be initiated by certain molecules on pathogen surfaces. The CP is typically initiated by antibody recognition of, and binding to, an antigenic site on a target cell. These pathways converge at the C3 convertase—the point where complement component C3 is cleaved by an active protease to yield C3a and C3b.

The AP C3 convertase is initiated by the spontaneous hydrolysis of complement component C3, which is abundant in the plasma in the blood. This process, also known as "tickover," occurs through the spontaneous cleavage of a thioester bond in C3 to form C3i or $C3(H_2O)$. Tickover is facilitated by the presence of surfaces that support the binding of activated C3 and/or have neutral or positive charge characteristics (e.g., bacterial cell surfaces). This formation of $C3(H_2O)$ allows for the binding of plasma protein Factor B, which in turn allows Factor D to cleave Factor B into Ba and Bb. The Bb fragment remains bound to C3 to form a complex containing $C3(H_2O)Bb$—the "fluid-phase" or "initiation" C3 convertase. Although only produced in small amounts, the fluid-phase C3 convertase can cleave multiple C3 proteins into C3a and C3b and results in the generation of C3b and its subsequent covalent binding to a surface (e.g., a bacterial surface). Factor B bound to the surface-bound C3b is cleaved by Factor D to thus form the surface-bound AP C3 convertase complex containing C3b, Bb. See, e.g., Müller-Eberhard (1988) *Ann Rev Biochem* 57:321-347.

The AP C5 convertase—$(C3b)_2,Bb$—is formed upon addition of a second C3b monomer to the AP C3 convertase. See, e.g., Medicus et al. (1976) *J Exp Med* 144:1076-1093 and Fearon et al. (1975) *J Exp Med* 142:856-863. The role of the second C3b molecule is to bind C5 and present it for cleavage by Bb. See, e.g., Isenman et al. (1980) *J Immunol* 124:326-331. The AP C3 and C5 convertases are stabilized by the addition of the trimeric protein properdin as described in, e.g., Medicus et al. (1976), supra. However, properdin binding is not required to form a functioning alternative pathway C3 or C5 convertase. See, e.g., Schreiber et al. (1978) *Proc Natl Acad Sci USA* 75: 3948-3952, and Sissons et al. (1980) *Proc Natl Acad Sci USA* 77: 559-562.

The CP C3 convertase is formed upon interaction of complement component C1, which is a complex of C1q, C1r, and C1s, with an antibody that is bound to a target antigen (e.g., a microbial antigen). The binding of the C1q portion of C1 to the antibody-antigen complex causes a conformational change in C1 that activates C1r. Active C1r then cleaves the C1-associated C1s to thereby generate an active serine protease. Active C1s cleaves complement component C4 into C4b and C4a. Like C3b, the newly generated C4b fragment contains a highly reactive thiol that readily forms amide or ester bonds with suitable molecules on a target surface (e.g., a microbial cell surface). C1s also cleaves complement component C2 into C2b and C2a. The complex formed by C4b and C2a is the CP C3 convertase, which is capable of processing C3 into C3a and C3b. The CP C5 convertase—C4b,C2a,C3b—is formed upon addition of a $C_3b$ monomer to the CP C3 convertase. See, e.g., Müller-Eberhard (1988), supra and Cooper et al. (1970) *J Exp Med* 132:775-793.

In addition to its role in C3 and C5 convertases, C3b also functions as an opsonin through its interaction with complement receptors present on the surfaces of antigen-presenting cells such as macrophages and dendritic cells. The opsonic function of C3b is generally considered to be one of the most important anti-infective functions of the complement system. Patients with genetic lesions that block C3b function are prone to infection by a broad variety of pathogenic organisms, while patients with lesions later in the complement cascade sequence, i.e., patients with lesions that block C5 functions, are found to be more prone only to *Neisseria* infection, and then only somewhat more prone.

The AP and CP C5 convertases cleave C5, which is a 190 kDa beta globulin found in normal human serum at approximately 75 μg/ml (0.4 μM). C5 is glycosylated, with about 1.5-3 percent of its mass attributed to carbohydrate. Mature C5 is a heterodimer of a 999 amino acid 115 kDa alpha chain that is disulfide linked to a 655 amino acid 75 kDa beta chain. C5 is synthesized as a single chain precursor protein product of a single copy gene (Haviland et al. (1991) *J Immunol.* 146:362-368). The cDNA sequence of the transcript of this human gene predicts a secreted pro-C5 precursor of 1658 amino acids along with an 18 amino acid leader sequence. See, e.g., U.S. Pat. No. 6,355,245.

The pro-C5 precursor is cleaved after amino acids 655 and 659, to yield the beta chain as an amino terminal fragment (amino acid residues +1 to 655 of the above sequence) and the alpha chain as a carboxyl terminal fragment (amino acid residues 660 to 1658 of the above sequence), with four amino acids (amino acid residues 656-659 of the above sequence) deleted between the two.

C5a is cleaved from the alpha chain of C5 by either alternative or classical C5 convertase as an amino terminal fragment comprising the first 74 amino acids of the alpha chain (i.e., amino acid residues 660-733 of the above sequence). Approximately 20 percent of the 11 kDa mass of C5a is attributed to carbohydrate. The cleavage site for convertase action is at, or immediately adjacent to, amino acid residue 733. A compound that would bind at, or adjacent to, this cleavage site would have the potential to block access of the C5 convertase enzymes to the cleavage site and thereby act as a complement inhibitor. A compound that binds to C5 at a site distal to the cleavage site could also have the potential to block C5 cleavage, for example, by way of steric hindrance-mediated inhibition of the interaction between C5 and the C5 convertase. A compound, in a mechanism of action consistent with that of the tick saliva complement inhibitor, *Ornithodoros moubata* C inhibitor ("OmCI"), may also prevent C5 cleavage by reducing flexibility of the C345C domain of the alpha chain of 05, which reduces access of the C5 convertase to the cleavage site of C5. See, e.g., Fredslund et al. (2008) *Nat Immunol* 9(7): 753-760.

C5 can also be activated by means other than C5 convertase activity. Limited trypsin digestion (see, e.g., Minta and Man (1997) *J Immunol* 119:1597-1602 and Wetsel and Kolb (1982) *J Immunol* 128:2209-2216) and acid treatment (Yamamoto and Gewurz (1978) *J Immunol* 120:2008 and Damerau et al. (1989) *Molec Immunol* 26:1133-1142) can also cleave 05 and produce active C5b.

Cleavage of C5 releases C5a, a potent anaphylatoxin and chemotactic factor, and leads to the formation of the lytic terminal complement complex, C5b-9. C5a and C5b-9 also have pleiotropic cell activating properties, by amplifying the release of downstream inflammatory factors, such as hydrolytic enzymes, reactive oxygen species, arachidonic acid metabolites and various cytokines.

The first step in the formation of the terminal complement complex involves the combination of C5b with C6, C7, and 08 to form the C5b-8 complex at the surface of the target cell. Upon the binding of the C5b-8 complex with several C9 molecules, the membrane attack complex ("MAC", C5b-9, terminal complement complex—"TCC") is formed. When sufficient numbers of MACs insert into target cell membranes the openings they create (MAC pores) mediate rapid osmotic lysis of the target cells, such as red blood cells. Lower, non-lytic concentrations of MACs can produce other effects. In particular, membrane insertion of small numbers of the C5b-9 complexes into endothelial cells and platelets can cause deleterious cell activation. In some cases, activation may precede cell lysis.

C3a and C5a are anaphylatoxins. These activated complement components can trigger mast cell degranulation, which releases histamine from basophils and mast cells, and other mediators of inflammation, resulting in smooth muscle contraction, increased vascular permeability, leukocyte activation, and other inflammatory phenomena including cellular proliferation resulting in hypercellularity. C5a also functions as a chemotactic peptide that serves to attract pro-inflammatory granulocytes to the site of complement activation.

C5a receptors are found on the surfaces of bronchial and alveolar epithelial cells and bronchial smooth muscle cells. C5a receptors have also been found on eosinophils, mast cells, monocytes, neutrophils, and activated lymphocytes.

While a properly functioning complement system provides a robust defense against infecting microbes, inappropriate regulation or activation of complement has been implicated in the pathogenesis of a variety of disorders, including, e.g., rheumatoid arthritis; lupus nephritis; asthma; ischemia-reperfusion injury; atypical hemolytic uremic syndrome ("aHUS"); dense deposit disease; paroxysmal nocturnal hemoglobinuria (PNH); macular degeneration (e.g., age-related macular degeneration; hemolysis, elevated liver enzymes, and low platelets (HELLP) syndrome; thrombotic thrombocytopenic purpura (TTP); spontaneous fetal loss; Pauci-immune vasculitis; epidermolysis bullosa; recurrent fetal loss; multiple sclerosis (MS); traumatic brain injury; and injury resulting from myocardial infarction, cardiopulmonary bypass and hemodialysis. See, e.g., Holers et al. (2008) Immunological Reviews 223:300-316.

Anti-C5 Antibody

An anti-C5 antibody for use in the methods of this disclosure for treating patients, for use as a capture antibody, and/or for use as a detection antibody, is any anti-human C5 antibody.

In certain embodiments, the anti-C5 antibody is eculizumab, an antigen-binding fragment thereof, a polypeptide comprising the antigen-binding fragment of eculizumab, a fusion protein comprising the antigen binding fragment of eculizumab, or a single chain antibody version of eculizumab.

In some embodiments, the complement C5 protein is a human complement C5 protein (the human proprotein is depicted in SEQ ID NO:4).

The anti-C5 antibody is one that binds to a complement C5 protein and is also capable of inhibiting the generation of C5a. An anti-C5 antibody can also be capable of inhibiting, e.g., the cleavage of C5 to fragments C5a and C5b, and thus preventing the formation of terminal complement complex.

For example, an anti-C5 antibody blocks the generation or activity of the C5a active fragment of a C5 protein (e.g., a human C5 protein). Through this blocking effect, the antibody inhibits, e.g., the proinflammatory effects of C5a. An anti-C5 antibody can further have activity in blocking the generation or activity of C5b. Through this blocking effect, the antibody can further inhibit, e.g., the generation of the C5b-9 membrane attack complex at the surface of a cell.

In some embodiments, the anti-C5 antibody is eculizumab. SEQ ID NO:5 depicts the entire heavy chain of eculizumab; SEQ ID NO:6 depicts the entire light chain of eculizumab; SEQ ID NOs:9-11 depict, respectively, CDR1-3 of the heavy chain of eculizumab; SEQ ID NOs: 12-14 depict, respectively, CDR1-3 of the light chain of eculizumab; SEQ ID NO:15 depicts the variable region of the heavy chain of eculizumab; and SEQ ID NO:16 depicts the variable region of the light chain of Eculizumab.

Eculizumab is a humanized anti-human C5 monoclonal antibody (Alexion Pharmaceuticals, Inc.), with a human IgG$_2$/IgG$_4$ hybrid constant region, so as to reduce the potential to elicit proinflammatory responses. Eculizumab has the trade name Soliris ° and is currently approved for treating paroxysmal nocturnal hemoglobinuria ("PNH") and atypical hemolytic uremic syndrome ("aHUS"). Paroxysmal nocturnal hemoglobinuria is a form of hemolytic anemia, intravascular hemolysis being a prominent feature due to the absence of the complement regulatory protein CD59 and CD55. CD59, for example, functions to block the formation of the terminal complement complex. AHUS involves chronic uncontrolled complement activation, resulting in, inter alia, inhibition of thrombolitic microangiopathy, the formation of blood clots in small blood vessels throughout the body, and acute renal failure. Eculizumab specifically binds to human C5 protein and blocks the formation of the generation of the potent proinflammatory protein C5a. Eculizumab further blocks the formation of the terminal complement complex. Eculizumab treatment reduces intravascular hemolysis in patients with PNH and decreases complement levels in aHUS. See, e.g., Hillmen et al., *N Engl J Med* 2004; 350:552-9; Rother et al., *Nature Biotechnology* 2007; 25(11): 1256-1264; Hillmen et al., *N Engl J Med* 2006, 355; 12, 1233-1243; Zuber et al., *Nature Reviews Nephrology* 8, 643-657 (2012)|doi:10.1038/nrneph.2012.214; U.S. Patent Publication Number 2012/0237515, and U.S. Pat. No. 6,355, 245.

In yet further other embodiments, the anti-C5 antibody is a single chain version of eculizumab, including pexelizumab (SEQ ID NO:1)—a specific single chain version of the whole antibody eculizumab. See, e.g., Whiss (2002) *Curr Opin Investig Drugs* 3(6):870-7; Patel et al. (2005) *Drugs Today (Barc)* 41(3):165-70; Thomas et al. (1996) *Mol Immunol* 33(17-18):1389-401; and U.S. Pat. No. 6,355,245. In yet other embodiments, the inhibitor for use in methods of this invention is a single chain variant of pexelizumab, with the arginine (R) at position 38 (according to Kabat numbering and the amino acid sequence number set forth in SEQ ID NO:2) of the light chain of the pexelizumab antibody amino acid sequence changed to a glutamine (Q). The single chain antibody having the amino acid sequence depicted in SEQ ID NO:2 is a variant of the single chain antibody pexelizumab (SEQ ID NO:1), in which the arginine (R) at position 38 has been substituted with a glutamine (Q). An exemplary linker amino acid sequence present in a variant pexelizumab antibody is shown in SEQ ID NO:3.

In certain embodiments, the anti-C5 antibody is a variant derived from eculizumab, having one or more improved properties (e.g., improved pharmacokinetic properties) relative to eculizumab. The variant eculizumab antibody (also referred to herein as an eculizumab variant, a variant eculizumab, or the like) or C5-binding fragment thereof is one that: (a) binds to complement component C5; (b) inhibits the generation of C5a; and can further inhibit the cleavage of C5 into fragments C5a and C5b. The variant eculizumab antibody can have a serum half-life in a human that is greater than, or at least, 10 (e.g., greater than, or at least, 11, 12, 13, 14, 15, 16, 17, 18, 19, 20, 21, 22, 23, 24, 25, 26, 27, 28, 29, 30, 31, 32, 33 or 34) days. Such variant eculizumab antibodies are described in PCT/US2015/019225 and U.S. Pat. No. 9,079,949.

In certain embodiments, the eculizumab variant antibody is an antibody defined by the sequences depicted in SEQ ID NO:7 (heavy chain) and SEQ ID NO:8 (light chain), or an antigen-binding fragment thereof. This antibody is also known as ALXN1210. This antibody binds to human C5 and inhibits the formation of C5a, as well as the cleavage of C5 to fragments C5a and C5b, and thus preventing the formation of terminal complement complex.

In certain embodiments, the eculizumab variant is BNJ441 (an antibody comprising the sequences depicted in SEQ ID NO:24, SEQ ID NO:25, and SEQ ID NO:16; see also the sequences depicted in SEQ ID NOs:6-8). In certain embodiments, the eculizumab variant is defined by the sequences depicted in SEQ ID NO:24, SEQ ID NO:25 and SEQ ID NO:8.

In certain embodiments, the anti-C5 antibody is a polypeptide C5 inhibitor comprising or consisting of one or more sequences depicted by SEQ ID NOs:1-3, 5-16, and 23-29, and 33, such that the resulting polypeptide binds to complement protein C5 ("C5").

In some embodiments, an anti-C5 antibody for use in methods of this disclosure is not a whole antibody. In some embodiments, an anti-C5 antibody is a single chain antibody. In some embodiments, an anti-C5 antibody for use in methods of this disclosure is a bispecific antibody. In some embodiments, an anti-C5 antibody for use in methods of this disclosure is a humanized monoclonal antibody, a chimeric monoclonal antibody, or a human monoclonal antibody, or an antigen binding fragment of any of them.

The anti-C5 antibody for use in methods of this disclosure can comprise, or can consist of, the amino acid sequence depicted in SEQ ID NO:1, SEQ ID NO:2, SEQ ID NO:5 and SEQ ID NO:6, or SEQ ID NO: 7 and SEQ ID NO: 8, or an antigen binding fragment of any of the above. The polypeptide can comprise one or more of the amino acid sequence depicted in SEQ ID NOs:9-16.

In yet other embodiments, the anti-C5 antibody is LFG316 (Novartis, Basel, Switzerland, and MorphoSys, Planegq, Germany) or another antibody defined by the sequences of Table 1 in U.S. Pat. Nos. 8,241,628 and 8,883,158, Mubodina® (Adienne Pharma & Biotech, Bergamo, Italy) (see, e.g., U57,999,081), rEV576 (coversin) (Volution Immuno-pharmaceuticals, Geneva, Switzerland) (see, e.g., Penabad et al., *Lupus,* 2014 October; 23(12):1324-6. doi: 10.1177/0961203314546022), ARC1005 (Novo Nordisk, Bagsvaerd, Denmark), SOMAmers (SomaLogic, Boulder, CO), SOB1002 (Swedish Orphan Biovitrum, Stockholm, Sweden), RA101348 (Ra Pharmaceuticals, Cambridge, MA).

In some embodiments, the anti-C5 antibody may be a monoclonal antibody. In other embodiments, the anti-C5 antibody comprises the variable region, or a fragment thereof, of an antibody, such as a monoclonal antibody. In other embodiments, the anti-C5 antibody is an immunoglobulin that binds specifically to a C5 complement protein. In other embodiments, the anti-C5 antibody is an engineered protein or a recombinant protein. In some embodiments, an anti-C5 antibody is not a whole antibody, but comprises parts of an antibody. In some embodiments, an anti-C5 antibody is a single chain antibody. In some embodiments, an anti-C5 antibody is a bispecific antibody. In some embodiments, the anti-C5 antibody is a humanized monoclonal antibody, a chimeric monoclonal antibody, or a human monoclonal antibody, or an antigen binding fragment of any of them. Methods of making an anti-C5 antibody are known in the art.

As stated above, the anti-C5 antibody inhibits complement component C5 protein. In particular, the anti-C5 antibody inhibits the generation of the C5a anaphylatoxin, or the generation of c5a and the C5b active fragments of a complement component C5 protein (e.g., a human C5 protein). Accordingly, the anti-C5 antibody inhibits, e.g., the proinflammatory effects of C5a; and may inhibit the generation of the C5b-9 membrane attack complex ("MAC") at the surface of a cell and subsequent cell lysis. See, e.g., Moongkarndi et al. (1982) *Immunobiol* 162:397 and Moongkarndi et al. (1983) *Immunobiol* 165:323.

In some embodiments, the anti-C5 antibodies are variant antibodies of an anti-C5 antibody (such as eculizumab) that still bind to the antigen, including deletion variants, insertion variants, and/or substitution variants. See, e.g., the polypeptides depicted in SEQ ID NO:1, SEQ ID NO:2, or SEQ ID NO:7 and SEQ ID NO:8. Methods of making such variants, by, for example, recombinant DNA technology, are well known in the art.

In some embodiments, an anti-C5 antibody is a fusion protein. The fusion protein can be constructed recombinantly such that the fusion protein is expressed from a nucleic acid that encodes the fusion protein. The fusion protein can comprise one or more C5-binding polypeptide segments (e.g., C5-binding segments depicted in SEQ ID NO:1, SEQ ID NO:2, or SEQ ID NO:5 and/or SEQ ID NO:6, SEQ ID NO: 7 and/or SEQ ID NO: 8, or any one or more of SEQ ID NOs:9-16) and one or more segments that are heterologous to the C5-binding segment(s). The heterologous sequence can be any suitable sequence, such as, for example, an antigenic tag (e.g., FLAG, polyhistidine, hemagglutinin ("HA"), glutathione-S-transferase ("GST"), or maltose-binding protein ("MBP")). Heterologous sequences can also be proteins useful as diagnostic or detectable markers, for example, luciferase, green fluorescent protein ("GFP"), or chloramphenicol acetyl transferase ("CAT"). In some embodiments, the heterologous sequence can be a targeting moiety that targets the C5-binding segment to a cell, tissue, or microenvironment of interest. In some embodiments, the targeting moiety is a soluble form of a human complement receptor (e.g., human complement receptor 2) or an antibody (e.g., a single chain antibody) that binds to C3b or C3d. In some embodiments, the targeting moiety is an antibody that binds to a tissue-specific antigen, such as a kidney-specific antigen. Methods of constructing such fusion proteins, such as by recombinant DNA technology, are well known in the art.

In some embodiments, the anti-C5 antibodies are fused to a targeting moiety. For example, a construct can contain a C5-binding polypeptide and a targeting moiety that targets the polypeptide to a site of complement activation. Such targeting moieties can include, e.g., soluble form of complement receptor 1 (CR1), a soluble form of complement receptor 2 (CR2), or an antibody (or antigen-binding fragment thereof) that binds to C3b and/or C3d.

Methods for generating fusion proteins (e.g., fusion proteins containing a C5-binding polypeptide and a soluble form of human CR1 or human CR2), including recombinant DNA technology, are known in the art and described in, e.g., U.S. Pat. No. 6,897,290; U.S. patent application publication no. 2005265995; and Song et al. (2003) *J Clin Invest* 11(12):1875-1885.

In certain embodiments, the anti-C5 antibody is a bispecific antibody. Methods for producing a bispecific antibody (e.g., a bispecific antibody comprising an anti-C5 antibody and an antibody that binds to C3b and/or C3d) are also known in the art. A bispecific antibody comprising a C5-binding antibody and any other antibody is contemplated.

A wide variety of bispecific antibody formats are known in the art of antibody engineering and methods for making the bispecific antibodies (e.g., a bispecific antibody comprising an anti-C5 antibody [i.e., a C5-binding antibody] and an antibody that binds to C3b, C3d, or a tissue-specific antigen) are well within the purview of those skilled in the art. See, e.g., Suresh et al. (1986) *Methods in Enzymology* 121:210; PCT Publication No. WO 96/27011; Brennan et al. (1985) Science 229:81; Shalaby et al., *J. Exp. Med.* (1992) 175:217-225; Kostelny et al. (1992) *J Immunol* 148(5): 1547-1553; Hollinger et al. (1993) *Proc Natl Acad Sci USA* 90:6444-6448; Gruber et al. (1994) *J Immunol* 152:5368; and Tutt et al. (1991) *J Immunol* 147:60.

Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques. U.S. Pat. No. 5,534,254 describes several different types of bispecific antibodies including, e.g., single chain Tv fragments linked together by peptide couplers, chelating agents, or chemical or disulfide couplings. In another example, Segal and Bast [(1995) *Curr Protocols Immunol Suppl.* 14:2.13.1-2.13.16] describes methods for chemically cross-linking two monospecific antibodies to thus form a bispecific antibody. A bispecific antibody can be formed, e.g., by conjugating two single chain antibodies which are selected from, e.g., a C5-binding antibody and an antibody that binds to, e.g., C3b, C3d, or a lung-specific antigen, an eye-specific antigen, a kidney-specific antigen, etc.

The bispecific antibody can be a tandem single chain (sc) Tv fragment, which contains two different scFv fragments covalently tethered together by a linker (e.g., a polypeptide linker). See, e.g., Ren-Heidenreich et al. (2004) *Cancer* 100:1095-1103 and Korn et al. (2004) *J Gene Med* 6:642-651. Examples of linkers can include, but are not limited to, $(Gly_4Ser)_2$ [GGGGSGGGGS, SEQ ID NO:17], $(Gly_4Ser)_3$ [GGGGSGGGGSGGGGS, SEQ ID NO:18], $(Gly_3Ser)_4$ [GGGSGGGSGGGSGGGS, SEQ ID NO:19], (G3S) [GGGS, SEQ ID NO:20], $SerGly_4$ [SGGGG, SEQ ID NO:21], and $SerGly_4SerGly_4$ [SGGGGSGGGG, SEQ ID NO:22].

In some embodiments, the linker can contain, or be, all or part of a heavy chain polypeptide constant region such as a CH1 domain as described in, e.g., Grosse-Hovest et al. (2004) *Proc Natl Acad Sci USA* 101:6858-6863. In some embodiments, the two antibody fragments can be covalently tethered together by way of a polyglycine-serine or polyserine-glycine linker as described in, e.g., U.S. Pat. Nos. 7,112,324 and 5,525,491, respectively. See also U.S. Pat. No. 5,258,498. Methods for generating bispecific tandem scFv antibodies are described in, e.g., Maletz et al. (2001) *Int J Cancer* 93:409-416; Hayden et al. (1994) *Ther Immunol* 1:3-15; and Honemann et al. (2004) *Leukemia* 18:636-644. Alternatively, the antibodies can be "linear antibodies" as described in, e.g., Zapata et al. (1995) *Protein Eng.* 8(10):1057-1062. Briefly, these antibodies comprise a pair of tandem Fd segments ($V_H$-$C_H$1-$V_H$-$C_H$1) that form a pair of antigen binding regions.

A bispecific antibody can also be a diabody. Diabody technology described by, e.g., Hollinger et al. (1993) *Proc Natl Acad Sci USA* 90:6444-6448 has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. See also Zhu et al. (1996) *Biotechnology* 14:192-196 and Helfrich et al. (1998) *Int J Cancer* 76:232-239. Bispecific single chain diabodies ("scDb") as well as methods for generating scDb are described in, e.g., Brusselbach et al. (1999) *Tumor Targeting* 4:115-123; Kipriyanov et al. (1999) *J Mol Biol* 293:41-56; and Nettlebeck et al. (2001) *Mol Ther* 3:882-891.

Variant forms of bispecific antibodies such as the tetravalent dual variable domain immunoglobulin (DVD-Ig) molecules described in Wu et al. (2007) *Nat Biotechnol* 25(11): 1290-1297 can also be used in the methods of this invention. The DVD-Ig molecules are designed such that two different light chain variable domains ($V_L$) from two different parent antibodies are linked in tandem directly or via a short linker by recombinant DNA techniques, followed by the light chain constant domain. Methods for generating DVD-Ig molecules from two parent antibodies are further described in, e.g., PCT Publication Nos. WO 08/024188 and WO 07/024715. Also embraced is the bispecific format described in, e.g., U.S. patent application publication no. 20070004909. Another bispecific format that can be used is the Cross-Over Dual V Region (CODV-Ig) which is a format for engineering four domain antibody-like molecules described in WO2012/135345. CODV-Ig was shown to be useful in engineering bispecific antibody-like molecules where steric hindrance at the C-terminal V domains (internal) may prevent construction of a DVD-Ig.

The C5-binding antibodies and/or targeting-moieties that are used to form the bispecific antibody molecules can be, e.g., chimeric, humanized, rehumanized, deimmunized, or fully human, all of which are well known in the art.

An anti-C5 antibody may be produced by recombinant DNA techniques. For example, a nucleic acid encoding a C5-binding polypeptide (e.g., a C5-binding polypeptide comprising or consisting of the amino acid sequence depicted in SEQ ID NO:2) can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

Several possible vector systems (such as plasmid vector systems) well known in the art are available for the expression of an anti-C5 antibody from nucleic acids in a number of cells, including in mammalian cells.

The expression vectors can be introduced by methods well known in the art into cells in a manner suitable for subsequent expression of the nucleic acid.

An anti-C5 antibody may be expressed in any appropriate host cells. Appropriate host cells include, for example, yeast, bacteria, insect, plant, and mammalian cells, including bacteria such as *E. coli*, fungi such as *Saccharomyces cerevisiae* and *Pichia pastoris*, insect cells such as SF9, mammalian cell lines (e.g., human cell lines), primary cell lines (e.g., primary mammalian cells), Chinese hamster ovary ("CHO") cells, and a suitable myeloma cell line such as NS0.

In some embodiments, an anti-C5 antibody may be expressed in, and purified from, transgenic animals (e.g., transgenic mammals). For example, an anti-C5 antibody may be produced in transgenic non-human mammals (e.g., rodents, sheep or goats) and isolated from milk as described in, e.g., Houdebine (2002) *Curr Opin Biotechnol* 13(6):625-629; van Kuik-Romeijn et al. (2000) *Transgenic Res* 9(2): 155-159; and Pollock et al. (1999) *J Immunol Methods* 231(1-2):147-157.

The anti-C5 antibody may be produced from cells by culturing a host cell transformed with the expression vector containing nucleic acid encoding the polypeptides, under conditions, and for an amount of time, sufficient to allow expression of the proteins. Such conditions for protein expression will vary with the choice of the expression vector and the host cell, and will be easily ascertained by one skilled in the art through routine experimentation. See, e.g., Current Protocols in Molecular Biology, Wiley & Sons, and Molecular Cloning—A Laboratory Manual—3rd Ed., Cold Spring Harbor Laboratory Press, New York (2001), which has comprehensive disclosure of recombinant DNA technology.

Following expression, the anti-C5 antibody may be isolated or purified in a variety of ways known to those skilled in the art.

In some embodiments, an anti-C5 antibody described herein comprises a heavy chain variable region comprising the following amino acid sequence:

(SEQ ID NO: 24)
QVQLVQSGAEVKKPGASVKVSCKASGHIFSNYWIQWVRQAPGQGLEWMGE
ILPGSGHTEYTENFKDRVTMTRDTSTSTVYMELSSLRSEDTAVYYCARYF
FGSSPNWYFDVWGQGTLVTVSS.

In some embodiments, an anti-C5 antibody comprises a light chain variable region comprising the following amino acid sequence:

(SEQ ID NO: 16)
DIQMTQSPSSLSASVGDRVTITCGASENIYGALNWYQQKPGKAPKLLIY
GATNLADGVPSRFSGSGSGTDFTLTISSLQPEDFATYYCQNVLNTPLTF
GQGTKVEIK.

An anti-C5 antibody can, in some embodiments, comprise a variant human Fc constant region that binds to human neonatal Fc receptor (FcRn) with greater affinity than that of the native human Fc constant region from which the variant human Fc constant region was derived. For example, the Fc constant region can comprise one or more (e.g., two, three, four, five, six, seven, or eight or more) amino acid substitutions relative to the native human Fc constant region from which the variant human Fc constant region was derived. The substitutions can increase the binding affinity of an IgG antibody containing the variant Fc constant region to FcRn at pH 6.0, while maintaining the pH dependence of the interaction. See, e.g., Hinton et al. (2004) *J Biol Chem* 279:6213-6216 and Datta-Mannan et al. (2007) *Drug Metab Dispos* 35:1-9. Methods for testing whether one or more substitutions in the Fc constant region of an antibody increase the affinity of the Fc constant region for FcRn at pH 6.0 (while maintaining pH dependence of the interaction) are known in the art and exemplified in the working examples. See, e.g., Datta-Mannan et al. (2007) *J Biol Chem* 282(3): 1709-1717; International Publication No. WO 98/23289; International Publication No. WO 97/34631; and U.S. Pat. No. 6,277,375.

Substitutions that enhance the binding affinity of an antibody Fc constant region for FcRn are known in the art and include, e.g., (1) the M252Y/S254T/T256E triple substitution described by Dall'Acqua et al. (2006) *J Biol Chem* 281: 23514-23524; (2) the M428L or T250Q/M428L substitutions described in Hinton et al. (2004) *J Biol Chem* 279:6213-6216 and Hinton et al. (2006) *J Immunol* 176: 346-356; and (3) the N434A or T307/E380A/N434A substitutions described in Petkova et al. (2006) *Int Immunol* 18(12):1759-69. The additional substitution pairings: P257I/Q3111, P257I/N434H, and D376V/N434H are described in, e.g., Datta-Mannan et al. (2007) *J Biol Chem* 282(3):1709-1717.

In some embodiments, the variant constant region has a substitution at EU amino acid residue 255 for valine. In some embodiments, the variant constant region has a substitution at EU amino acid residue 309 for asparagine. In some embodiments, the variant constant region has a substitution at EU amino acid residue 312 for isoleucine. In some embodiments, the variant constant region has a substitution at EU amino acid residue 386.

In some embodiments, the variant Fc constant region comprises no more than 30 (e.g., no more than 29, 28, 27, 26, 25, 24, 23, 22, 21, 20, 19, 18, 17, 16, 15, 14, 13, 12, 11, 10, nine, eight, seven, six, five, four, three, or two) amino acid substitutions, insertions, or deletions relative to the native constant region from which it was derived. In some embodiments, the variant Fc constant region comprises one or more amino acid substitutions selected from the group consisting of: M252Y, S254T, T256E, N434S, M428L, V259I, T250I, and V308F. In some embodiments, the variant human Fc constant region comprises a methionine at position 428 and an asparagine at position 434, each in EU numbering. In some embodiments, the variant Fc constant region comprises a 428L/434S double substitution as described in, e.g., U.S. Pat. No. 8,088,376.

In some embodiments, the variant constant region comprises a substitution at amino acid position 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434, or 436 (EU numbering) relative to the native human Fc constant region. In some embodiments, the substitution is selected from the group consisting of: methionine for glycine at position 237; alanine for proline at position 238; lysine for serine at position 239; isoleucine for lysine at position 248; alanine, phenylalanine, isoleucine, methionine, glutamine, serine, valine, tryptophan, or tyrosine for threonine at position 250; phenylalanine, tryptophan, or tyrosine for methionine at position 252; threonine for serine at position 254; glutamic acid for arginine at position 255; aspartic acid, glutamic acid, or glutamine for threonine at position 256; alanine, glycine, isoleucine, leucine, methionine, asparagine, serine, threonine, or valine for proline at position 257; histidine for glutamic acid at position 258; alanine for aspartic acid at position 265; phenylalanine for aspartic acid at position 270; alanine, or glutamic acid for asparagine at position 286; histidine for threonine at position 289; alanine for asparagine at position 297; glycine for serine at position 298; alanine for valine at position 303; alanine for valine at position 305; alanine, aspartic acid, phenylalanine, glycine, histidine, isoleucine, lysine, leucine, methionine, asparagine, proline, glutamine, arginine, serine, valine, tryptophan, or tyrosine for threonine at position 307; alanine, phenylalanine, isoleucine, leucine, methionine, proline, glutamine, or threonine for valine at position 308; alanine, aspartic acid, glutamic acid, proline, or arginine for leucine or valine at position 309; alanine, histidine, or isoleucine for glutamine at position 311; alanine or histidine for aspartic acid at position 312; lysine or arginine for leucine at position 314; alanine or histidine for asparagine at position 315; alanine for lysine at position 317; glycine for asparagine at position 325; valine for isoleucine at position 332; leucine for lysine at position 334; histidine for lysine at position 360; alanine for aspartic acid at position 376; alanine for glutamic acid at position 380; alanine for glutamic acid at position 382; alanine for asparagine or serine at position 384; aspartic acid or histidine for glycine at position 385; proline for glutamine at position 386; glutamic acid for proline at position 387; alanine or serine for asparagine at position 389; alanine for serine at position 424; alanine, aspartic acid, phenylalanine, glycine, histidine, isoleucine, lysine, leucine, asparagine, proline, glutamine, serine, threonine, valine, tryptophan, or tyrosine for methionine at position 428; lysine for histidine at position 433; alanine, phenylalanine, histidine, serine, tryptophan, or tyrosine for asparagine at position 434; and histidine for tyrosine or phenylalanine at position 436, all in EU numbering.

An anti-C5 antibody may be used as a therapeutic agent and is administered to a patient in needed thereof as any suitable formulation/composition and by any suitable route (such as by IV injection). An anti-C5 antibody may also be used as a capture antibody or a detection antibody in methods disclosed herein.

Back Disassociation ELSIA Assay Modeling

When quantifying target/efficacy biomarkers, traditional plate based ligand binding assays have potential to overestimate free analyte. Overestimation of free analyte in such situations suggests lower lack of efficacy than that which is true in vivo. Eculizumab is a mAb therapeutic approved for 2 ultra rare disease indications, and targets complement factor C5 (190 kD). Proper quantification of free C5 in the presence of drug is crucial.

Based on Biacore results, approximately 15% of Eculizumab-C5 complexes dissociate in 60 minutes, with $k_a = \sim 1.1e\ 6$ (1/M s) and $k_d = 4.6e^{-5}$ (1/s) at 25° C., in traditional plate based ligand binding assays.

Table 1 shows the amount (in %) of antibody that remains bound to its antigen as a function (Kd—percent that dissociates per second) of time.

TABLE 1

| kd (1/s) | 1 hour | 24 hours 1 Day | 48 hours 2 Days | 72 hours 3 Days | 168 hours 1 Week |
|---|---|---|---|---|---|
| 5E−03 | 0 | 0 | 0 | 0 | 0 |
| 5E−04 | 16.5 | 0 | 0 | 0 | 0 |
| 5E−05 | 83.5 | 1.3 | 0 | 0 | 0 |
| 5E−06 | 98.2 | 64.9 | 42.1 | 27.4 | 4.9 |
| 5E−07 | 99.8 | 95.8 | 91.7 | 87.8 | 73.9 |
| 5E−08 | 100 | 99.6 | 99.1 | 98.7 | 97 |
| 5E−09 | 100 | 100 | 99.9 | 99.9 | 99.7 |

The experimental evidence shows that antigen binding to ELSIA plate requires at least 30 hours for solution and plate to arrive at equilibrium.

The critical parameters are incubation time, dilution time, dilution temperature, and sample vs. assay range. Shorter plate incubation time may decrease disassociation. Cooling during two dilution steps may slow off rate k d and keep antigen-mAb and antigen-mAb-antigen from disassociating. Shorter dilution time may decrease disassociation. Dilute less may decrease disassociation. Measure neat samples if possible.

Antigen Concentration and mAb concentration (PK) data mismatch is due to: Different assay dilutions and times; Measured Antigen Concentration is over estimating free Antigen; and measured mAb (PK) is over estimating true free mAb due to disassociation from dilution and under estimating total mAb due to solution antigen.

Hemolysis modeling (using hemolytic assay for human serum samples containing C5) suggests that antigen, PK, and hemolysis (PD) data mismatch is due to: Different assay dilutions and times; Measured antigen concentration is over estimating free Antigen in hemolysis assay; Measured mAb—Eculizumab—(PK) is over estimating true free mAb due to disassociation from dilution and under estimating total mAb due to solution antigen; and Measured hemolysis is over estimating true free Antigen due to disassociation from dilution.

Equilibrium Equation
kon $$mAb + L = mAb*L$$

koff $$K_d = 1/k_a = [mAb]_{free} \times [L]_{free}/[mAb*L]_{bound}$$

$$Kd = \frac{kon}{koff} \quad (M)$$

$K_d$=dissociation constant, $K_a$=association constant
$K_{off}$=dissociation rate, $k_{on}$=association rate After dosing, binding of mAb to soluble L (ligand) in vivo assumed to follow law of mass action. Ex vivo conditions such as sample collection, storage, etc. may shift equilibrium to conditions different from in vivo.

$k_{off}$ values often strongly temperature and buffer sensitive. Equilibration time increases by about 30-fold at 0° C. compared to 30° C. The dissociation rate constant should always be determined under the conditions of the assay.

$L_{free}$ Measurements
Increasingly used in drug development to guide decisions; useful in dose and schedule selection. Understanding L kinetics can help define efficacious $mAb_{free}$ levels.

Assays for Measuring Free C5 Target Ligand
Modified ELISA Assay Format
Remove bound forms prior to performing ELISA. Measure amount of dissociation using biacore or ELISA and subtract from what is measured. Measure total Eculizumab concentration using LC/MS or other method(s) and determine total C5. Calculate free C5 using equilibrium equation. Calculation is based on the equilibrium equation, which requires a good estimate of $K_d$ in vivo.

Modified MSD Free C5 Assay
Sample incubation decreased from 60-minute to proposed 15-minute incubation. Sample dilution decreased from 1:1000 to 1:2 (50% serum). Samples incubated on ice instead of at RT to possibly reduce dissociation.

Remove Bound Forms before ELISA:
Molecular Sieve
Solid Phase Extraction
Affinity separation, i.e. protein G, protein A or anti-human FC column
Additional processes may introduce error due to adsorption to column or filter
Dissociation may also occur and processes are labor intensive Certain Embodiment Methods of Quantifying Free C5
The Gyros system (Gyros AB, Uppsala, Sweden; www.gyros.com) is used in the methods disclosed herein. Since a Gyros assay passes samples along the microstructures in a matter of seconds, there may not be opportunity for back dissociation to occur. The Gyros system uses an affinity flow-through format and eliminates incubations and shortens run times. The Gyros platform uses Gyros' proprietary CD technology engineered with highly reproducible nano-liter microfluidics integrated with Gyrolab platforms, which automate immunoassays with parallel processing using laser-induced fluorescence detection. This is possible through precise, automated control of centrifugal and capillary forces which steer liquid flow through nanoliter-scale microfluidic structures contained within the CD.

Circular Bioaffy compact disc (CD) is used. PCR plates may be used for samples and reagents. Many available PCR plates may be used. The plates are sealed with foil to prevent evaporation. The capture reagent (such as a biotinylated anti-C5 antibody) enters the CD by capillary action. Hydrophobic breaks stop liquid flow. The CD is subjected to centrifugal force inside an instrument dedicated for the assay, such as a Gyrolab xPlore or Gyrolab XP. The centrifugal force drives reagents into columns inside the CD. Capture reagent binds to strepavidin-coated particles in the columns. The sample then enters the CD by capillary action and the sample applied to activated columns. The detection reagent (e.g. AlexaFluor labeled anti-C5 antibody; one that binds to a different epitope than the anti-C5 antibody used as capture reagent) then enters by capillary action and applied to columns. The columns are then scanned by laser (112 columns within 90 seconds). Rexxip A may be used for standards, QCs, samples and Rexxip F for detection Ab. Laser induced fluorescence is then used to measure the concentration or amount of the sample (e.g., C5).

The Gyros assay uses very little sample volume (such as 4 μL) and takes very little time (such as 1.5 hours). It has a calibration range of 0.78 pM-300 pM.

This disclosure provides a method of quantitating free (unbound) human C5 complement protein (C5) from a sample comprising:
  a. binding biotinylated anti-C5 capture antibody to strepavidin-coated particles; wherein said biotinylated anti-C5 capture antibody is added by capillary action to a Gyros Bioaffy 200 CD comprising columns with the strepavidin-coated particles; wherein said CD is subjected to centrifugal force inside a Gyrolab xPlore or a Gyrolab XP instrument, thus driving the biotinylated anti-C5 capture antibody to the strepavidin-coated particles in the columns;

b. capturing the free (unbound) C5 in the sample; wherein the sample is added to the CD by capillary action; wherein said CD is subjected to centrifugal force inside the Gyrolab xPlore or a Gyrolab XP instrument, thus driving the sample to the biotinylated anti-C5 capture antibody bound on the strepavidin-coated particles in the columns;

c. detecting the captured free C5; wherein an AlexaFluor labeled anti-C5 antibody detection is added to the CD by capillary action, wherein said anti-C5 detection antibody binds C5 at a different epitope from the epitope bound by the capture antibody; wherein said CD is subjected to centrifugal force inside the Gyrolab xPlore or a Gyrolab XP instrument, thus driving the detection antibody to the free C5 bound to the capture antibody bound on the strepavidin-coated particles in the columns; and d. quantitating the captured free C5 using laser-induced fluorescence detection.

Any suitable instrument for use of a Gyro assay, such as Gyrolab xPlore or Gyrolab XP, may be used.

In certain embodiments, Rexxip A buffer is used for samples and Rexxip F buffer is used for diluting the detection antibody. Any suitable buffer may be used.

In certain embodiments, the Gyros instrument is primed two separate times with Bioaffy wash 1 and pH 11 buffer. Any suitable buffer may be used and priming may be skipped and may be done any suitable number of times.

In another aspect, a method is provided of quantitating free (unbound) human C5 complement protein (C5) from a sample comprising: a. binding biotinylated anti-C5 capture antibody to strepavidin-coated Meso Scale Discovery® (MSD®) (Meso Scale Diagnostic, Rockville, MD; https://www.mesoscale.com/en 96-well assay plate; b. capturing the free (unbound) C5 in the sample by adding the sample to the plate; c. detecting the captured free C5 by adding sulfo-tagged anti-C5 (in certain embodiments, ruthenyled sulfo-tagged anti-C5) detection antibody to the plate; and d. quantitating the captured free C5 using electrochemiluminescence; wherein the sample is diluted by about 1:2; wherein the sample is kept on ice; wherein steps b.-C. are about 15 to 30 minutes, and wherein the biotinylated capture anti-C5 antibody is added at a concentration of about 5 µg/mL.

C5 in a sample, such as a serum sample from a patient treated with eculizumab, may be free (unbound) or may be bound to eculizumab.

In certain embodiments, the method further comprises calculating the concentration or amount of free C5 antibody in the sample by comparing the data obtained from step d. to a standard curve prepared from known amounts of C5 added to a C5 depleted sample. The sample with the controls is processed the same way as the patient's sample.

In certain embodiments, the method further comprises calculating the concentration of free C5 antibody with the Gyros Evaluator software, or other suitable software.

In certain embodiments, the sample is obtained from a human patient. In certain further embodiments, the sample is a serum sample. In yet other embodiments, the sample is from a patient undergoing treatment with an anti-C5 antibody, such as eculizumab or ALXN1210. In certain embodiments, the sample is taken before treatment with eculizumab or ALXN1210. In other embodiments, the sample is taken after treatment with eculizumab or ALXN1210. The sample may be any suitable sample that may contain C5 and may be serum, plasma, blood, urine, solid sample, etc. The samples may be obtained and prepared for use according to methods known in the art.

In certain embodiments, the biotinylated capture antibody is eculizumab or ALXN1210. The biotinylated capture antibody may be any anti-C5 antibody.

In certain embodiments, the detection anti-C5 antibody is N19-8 (mouse anti-human C5 antibody). The detection anti-C5 antibody may be any anti-C5 antibody. The detection anti-C5 antibody in any given assay is one that recognizes a different epitope on C5 as compared to the capture antibody used in that assay; and thus does not compete for binding to C5 with the capture antibody.

Methods of conjugating an antibody with biotin or AlexaFluor are known in the art.

In certain embodiments, the sample is a human serum sample from a patient; the free C5 of the patient's pre-treatment and post-treatment with an anti-C5 antibody serum samples are quantitated, and both the pre-treatment and the post-treatment sample is diluted to the same dilution. In further embodiments, the dilution used is 1:30.

Examplary Utility

The methods disclosed herein may be used for any purpose that requires quantifying the concentration or amount of free (unbound) C5 in a sample. The methods, for example, may be used to detect the concentration or amount of free (unbound) C5 in a human serum sample from a patient being treated by eculizumab therapy. The concentration or amount of free (unbound) C5 in such a sample would allow the patient's disease state be monitored. This assay has the advantage in such an example of quantifying free (unbound) C5 and not the C5 molecules bound to eculizumab used as therapy.

Proper quantification of free C5 is essential for a number of reasons, such as monitoring disease state, modeling, dosage selection, and label claims.

EXAMPLES

For this invention to be better understood, the following examples are set forth. These examples are for purposes of illustration only and are not be construed as limiting the scope of the invention in any manner.

Example 1. Gyrolab Platform for Quantifying Free C5

Complement protein C5 is an important component of the complement cascade, and a target of Alexion drugs eculizumab and ALXN1210. Proper quantification of this target is essential for both modeling and label claims. Many ligand binding assay formats that use drug as a capture reagent for free target are inherently flawed in that during sample incubation, the capture reagent can set up a dynamic equilibrium with target that is already bound to drug in matrix. Due to this equilibrium, it is possible for the assay to overestimate the amount of free target in matrix, thus leading to potentially inaccurate modeling, dosage selection, filing data, and label claims.

A common strategy for overcoming this overestimation in ligand binding assays is to abbreviate sample incubation time, thus reducing the opportunity for capture reagent to pull bound target from drug in matrix. In order to accomplish this, it is often necessary to increase the coating reagent concentration by as much as 5 times, which can in essence minimize the effects of the shortened sample incubation. Also, pretreatment samples tend to have much higher levels of free target than post treatment samples, often requiring different sample dilutions for each situation.

The Gyrolab technology is based on assay washes, reagents, and samples spinning across microstructures on a disc at proscribed intervals. The required time for a sample to be spun across a microstructure immobilized with capture reagent is about six seconds, so theoretically there is almost no time for any bound target in matrix to dissociate and be bound by the drug used as capture antibody. Additionally, the broad dynamic range of Gyros assays is more amenable to having one universal sample dilution across a range of study samples, rather than one for pretreatment samples and another for post treatment.

Materials & Methods

Materials:

Bioaffy 200 discs, Rexxip A buffer, Rexxip F buffer, pH 11 buffer, plate foil (Gyros US, Inc., Warren NJ)

Purified human C5, C5 depleted serum (CompTech, Tyler TX)

Biotinylated eculizumab, biotinylated ALXN1210, AlexaFluor labeled N19/8 antibody (Alexion Pharmaceuticals, New Haven CT)

96 well PCR plates, Bioaffy wash 1 (PBS with 0.1% Tween 0.02% sodium azide) (All wash ingredients from ThermoFisher, Waltham, MA)

Equipment:

Gyros xPlore or XP Workstation instrument (Gyros US, Inc., Warren NJ)

Method:

The Gyros instrument is primed two separate times with Bioaffy wash 1 and pH 11 buffer, each buffer with its own station. During these prime cycles (about twenty minutes each), assay reagents, washes, and samples are prepared as described below. The number of Bioaffy 200 discs required for the run (one for Gyros xPlore, up to five for Gyros XP Workstation) are removed from refrigerated storage and allowed to come to ambient room temperature.

The assay's standard curve is prepared from purified human C5 protein which is spiked into C5 depleted human serum at 300 µg/mL and then diluted 3 fold as follows: 300 (initial spike), 100, 33.3, 11.1, 3.70, 1.23, 0.41, 0.14, 0.045, 0.015, and 0.005 µg/mL. The 0.005 µg/mL standard sample is an anchor point. Once formulated in C5 depleted serum, the curve is diluted 1:5 in Rexxip A buffer, mixed, and then diluted one more time in Rexxip A buffer at 1:6 with mixing for a final dilution of 1:30. Diluted standards are put on the PCR plate in their respective positions and at their required volumes.

Quality control (QC) samples are formulated in the same manner as standard samples. Purified human C5 is spiked into C5 depleted human serum at 240, 10.0, and 0.045 µg/mL. These samples are then diluted twice (1:5 and then 1:6 in Rexxip A buffer) as described for the standard curve samples for a final dilution of 1:30. When required, samples at the limits of detection (300 µg/mL for upper limit of detection (ULOQ) and 0.015 µg/mL for lower limit of detection (LLOQ)) are formulated the same way. Diluted QCs are put on the PCR plate in their respective positions and at their required volumes.

Unknown human serum samples are diluted twice (1:5 and then 1:6 in Rexxip A buffer) for a final dilution of 1:30. Diluted unknown serum samples are put on the PCR plate in their respective positions and at their required volumes.

Biotinylated capture reagent (eculizumab or ALXN1210) is formulated to a working concentration of 100 µg/mL in Bioaffy wash 1, and AlexaFluor labeled N19/8 is formulated to a working concentration of 1 µg/mL in Rexxip F. Both of these reagents are placed in their respective predetermined locations on the PCR plate at their required volumes. Bioaffy wash 1 is used as the assay buffer and is loaded into respective predetermined locations on the PCR plate.

The PCR plate loaded with standards, QCs, any unknown serum samples, assay reagents, and assay washes is sealed with foil and then loaded onto the Gyros instrument. The required number of Bioaffy 200 discs is also loaded onto the instrument.

Assays are run on the Gyros system using the Gyros Client software. This is a three step assay (capture, analyte, detect) whereby capture antibody, sample, and detection antibody are added at programmed intervals and between intermittent wash steps. Assay run time is about one hour per disc. Data is processed by the Gyros Evaluator software, or can be exported for import into a laboratory information system (LIMS) such as Watson. This assay uses a 5PL curve fit with response weighting.

Results

The Gyros assay for the quantification of free C5 in human serum has a dynamic range of 0.039-18.75 µg/mL or 0.015-300 µg/mL, regardless of capture reagent used (eculizumab or ALXN1210). This dynamic range and sample dilution (in certain embodiments, 1:20 to 1:30 for the initial pre-treatment samples and then 2-fold for all samples after initial treatment) cover all anticipated concentrations of samples, whether pretreatment which could have free levels as high as 240 µg/mL (although rarely over 200 µg/mL), or post treatment which could have levels well below 0.5 µg/mL. See table 2 for details on assay performance over this range with ALXN1210 as capture reagent.

TABLE 2

Gyros QC Performance Across Dynamic Range of Free C5 Measurement in Human Serum (2 days, 4 separate runs)

| QC Level | Expected µg/mL | Mean measured µg/mL | Std Dev | % CV | % Recovery |
|---|---|---|---|---|---|
| ULOQ | 300 | 271.8 | 16.390 | 6.0 | 90.6 |
| HQC | 240 | 235.5 | 9.032 | 3.8 | 98.1 |
| MQC | 10 | 8.61 | 0.656 | 7.6 | 86.1 |
| LQC | 0.045 | 0.0391 | 0.006 | 15.9 | 87.0 |
| LLOQ | 0.015 | 0.0152 | 0.003 | 17.1 | 101.5 |

Selectivity of a target biomarker assay is an important assay parameter. Table 3 shows data for ten donor sera spiked with 50 µg/mL of purified C5 reference material, which has an additive effect on the measurement of the endogenous C5 levels already in each sample. The Gyros assay accurately measured purified C5 spiked into samples containing the endogenous counterpart.

TABLE 3

Gyros Selectivity of Ten Donor Samples for Free C5 in Human Serum (ALXN1210 capture)

| Sample | Mean Unspiked (endogenous) | CV % | Mean Spiked | CV % | Corrected (Blk Endog + Spiked Conc) Conc | % Bias |
|---|---|---|---|---|---|---|
| SEL01 | 48.3 | 4.1 | 108.9 | 8.9 | 98.3 | 10.8 |
| SEL02 | 151.9 | 4.4 | 205.8 | 4.0 | 201.9 | 1.9 |
| SEL03 | 56.3 | 3.2 | 111.3 | 7.4 | 106.3 | 4.8 |

TABLE 3-continued

Gyros Selectivity of Ten Donor Samples for Free
C5 in Human Serum (ALXN1210 capture)

| Sample | Mean Unspiked (endogenous) | CV % | Mean Spiked | CV % | Corrected (Blk Endog + Spiked Conc) Conc | % Bias |
|---|---|---|---|---|---|---|
| SEL04 | 140.2 | 10.3 | 194.8 | 1.1 | 190.2 | 2.4 |
| SEL05 | 96.3 | 3.0 | 180.5 | 8.9 | 146.3 | 23.4 |
| SEL06 | 136.4 | 9.5 | 178.2 | 3.9 | 186.4 | −4.4 |
| SEL07 | 143.8 | 4.2 | 207.3 | 2.4 | 193.8 | 7.0 |
| SEL08 | 95.4 | 1.5 | 164.3 | 1.5 | 145.4 | 13.0 |
| SEL09 | 149.9 | 5.7 | 209.7 | 2.7 | 199.9 | 4.9 |
| SEL10 | 110.6 | 0.3 | 167.5 | 4.1 | 160.6 | 4.3 |
| Spike Control | 51.6 | 2.2 | — | — | — | — |

Parallelism is an important element to determine in a biomarker assay, as it can be a determination of the goodness of fit of a surrogate matrix (here, C5 depleted human serum) standard curve and its purified reference material (here, purified human C5). By pretreating matrix samples with extra dilutions prior to the proscribed dilution of 1:30, parallelism can show differences in assay response between the surrogate curve and unknown samples measured from it. FIG. 1 shows parallelism results for both three individual donor sera and three QC sample concentrations that are prepared similarly to the QC samples described above. These data suggest that the assay has parallelism, and that the surrogate curve is appropriate. FIG. 1. Individual sera samples and QC samples spiked in C5 depleted serum then diluted in same serum prior to MRD pass parallelism test.

A human serum pool was spiked at various concentrations of eculizumab. This was repeated with another aliquot of the same pool with various concentrations of ALXN1210. Both sets of spiked samples were assayed on both the plate based free C5 assay and the Gyros free C5 assay. Eculizumab spiked samples were assayed using eculizumab as a capture reagent on both assay platforms, and ALXN1210 samples were assayed using ALXN1210 as capture on both. Tables 4 and 5 show results for the plate based and Gyros assay, respectively. Gyros assay results for each set of spiked samples are lower, indicating that unlike the plate based assay, there is little to no bound C5 being pulled from drug in serum and bound to the capture reagent.

TABLE 4

Plate Based Assay Results for Free C5 in Human Serum,
ALXN1210 and Eculizumab Spike

| Drug Conc (µg/mL) in Human Serum | ALXN1210, Measured Free C5, ug/mL, N = 3 | Eculizumab, Measured Free C5, ug/mL, N = 3 | Free C5 Ratio 1210/Ecu |
|---|---|---|---|
| 200 | 0.25 | 0.03 | 8.3 |
| 100 | 0.46 | 0.04 | 12.2 |
| 50 | 0.80 | 0.06 | 12.5 |
| 20 | 22.8 | 17.3 | 1.3 |
| 5 | 72.1 | 72.9 | 1.0 |
| 0 | 91.6 | 91.8 | 1.0 |

TABLE 6

Gyros Assay Results for Free C5 in Human Serum,
ALXN1210 and Eculizumab Spikes

| Drug Conc (µg/mL) in Human Serum | ALXN1210 spike, Measured Free C5, ug/mL, N = 6 | Eculizumab spike, Measured Free C5, ug/mL, N = 3 | Free C5 Ratio 1210/Ecu |
|---|---|---|---|
| 200 | 0.037 | <0.005 | 7.4 |
| 100 | 0.12 | <0.005 | 24 |
| 50 | 0.46 | <0.005 | 92 |
| 20 | 15.1 | 8.1 | 1.9 |
| 5 | 52.5 | 46.1 | 1.1 |
| 0 | 63.5 | 63.5 | NA |

Discussion

The Gyros assay for the quantification of free C5 in human serum has a broad dynamic range (0.015-300 µg/mL for either eculizumab or ALXN1210 capture reagent). This dynamic range at the sample dilution of 1:30 enables measurement of both pretreatment and post treatment samples, thereby eliminating the requirement for different dilutions for each respective scenario. This common dilution also takes away sample processing errors, whereby samples can be assayed at incorrect dilutions.

The selectivity and parallelism of the assay show that the surrogate matrix and reference material are appropriate for the endogenous counterpart being measured in human serum.

Data from spiked samples run on both the Gyros assay and a plate based assay, both using therapeutic drugs as a capture reagent, suggest that the Gyros assay vastly reduces the potential of drug being used as a capture reagent to reach any equilibrium with C5 that is already bound to drug in a serum sample. This reduction in equilibrium and its associated potential for over quantifying C5 that truly is free, along with the extended dynamic range that affords a common sample dilution, enable the end user to have more accurate measurements.

Example 2. Free C5 Gyro Assay

Figure 2:
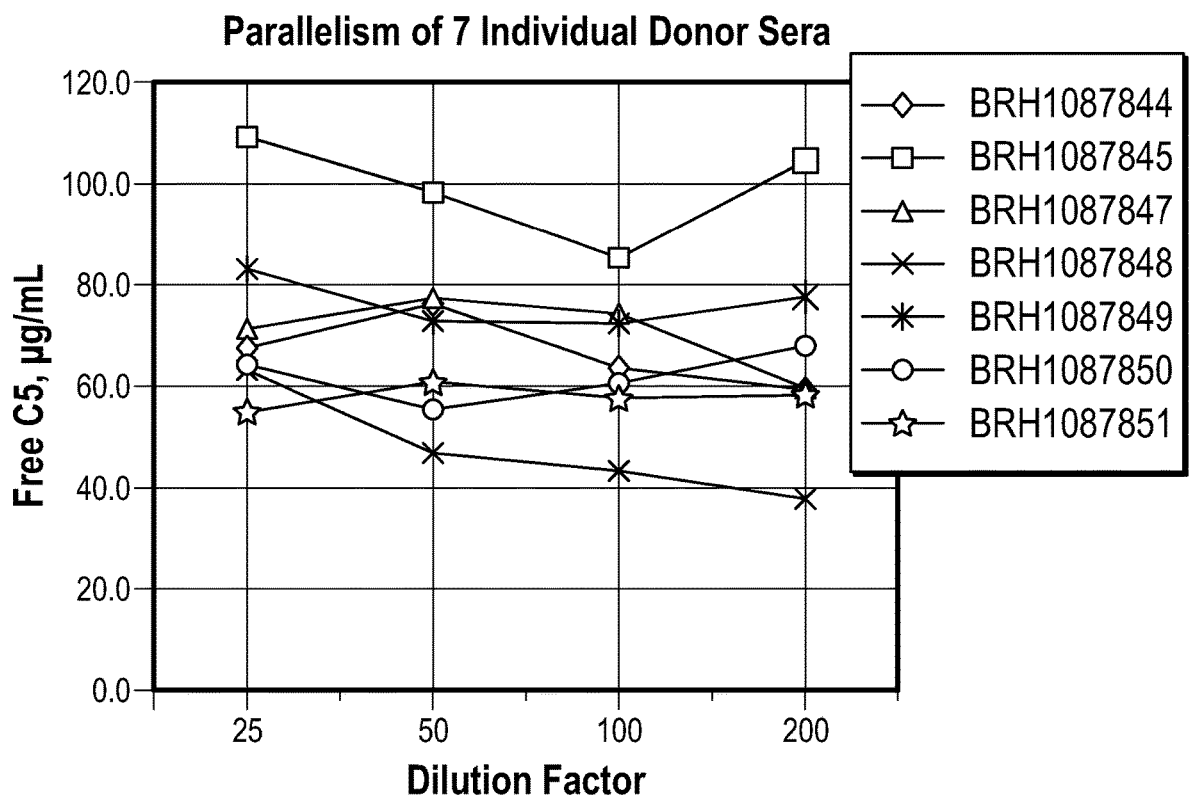
FIG. 2 is a graph showing parallelism of 7 individual donor sera.
Figures 4C, 5:
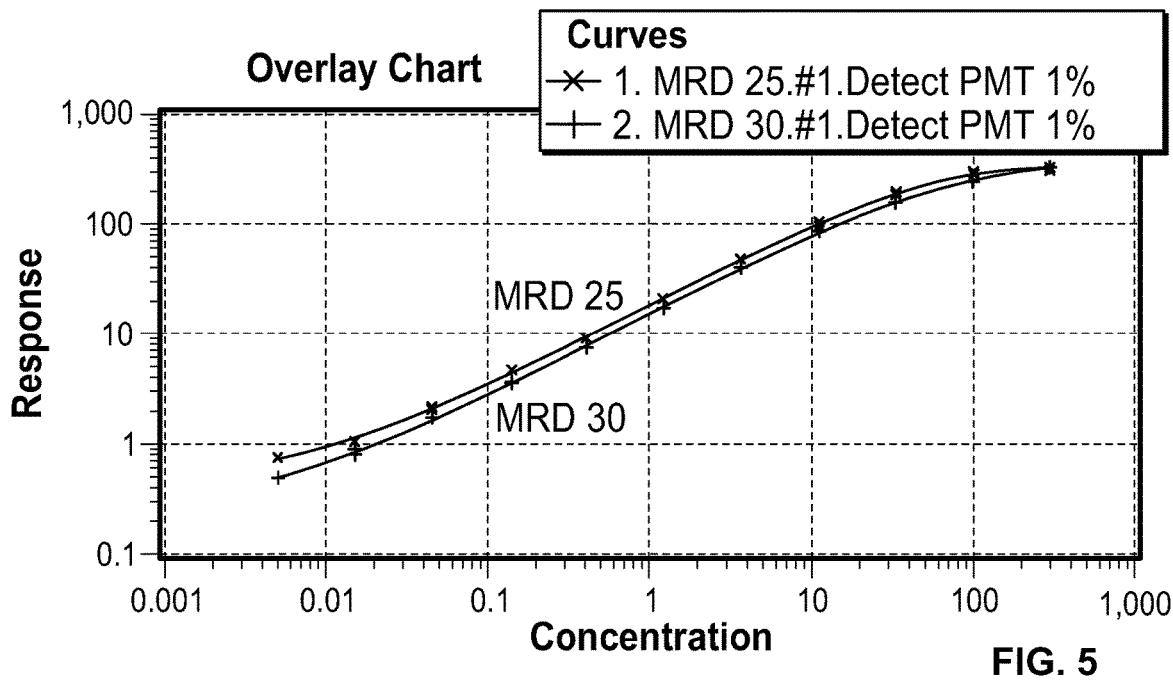
FIG. 4C shows selectivity in early CRO transfer results.
FIG. 5 shows that MRD (minimum required dilution) of 30 is optimal.

Assay Parameters
Capture Ab @ 100 µg/mL
Detect Ab @ 1 µg/mL
Purified human C5 as reference material
C5 depleted serum for formulation of standards and QCs
Bioaffy 200 nL discs
Rexxip A for standards, QCs, samples (sample dilution 30)
Rexxip F for detection Ab
Wash 1: Bioaffy wash 1
Wash 2: pH 11 buffer
3 step assay (C-A-D)
PMT 1%
Current plate based ECL assay format has dynamic range of 0.0274-20.0 µg/mL
Sample dilution scheme: 20 for pretreatment, 2 for treatment
Typical endogenous concentrations of free C5 range from 50.0 to 150.0 µg/mL
Proposed curve range 0.005-300.0 µg/mL, preferably common dilution for all samples
Parallelism of 7 individual donor sera is shown in FIG. 2 and FIG. 3. This is an improvement over prior ECL assays, where dilutions beyond MRD yielded diminishing returns.
Early CRO assay transfer results are shown in FIG. 4A and FIG. 4B (summary data for two days; N=6 for each QC level (2 runs, each of N=3) (Confirmation of MRD (30)). Limits of quantitation cover desired range of assay; one dilution covers all anticipated eventualities. FIG. 4C shows selectivity in early CRO transfer results.

FIG. 5 shows that MRD (minimum required dilution) of 30 is optimal. Going from 25 to 30 lost a bit of low end sensitivity (5 ng/mL vs. 15 ng/mL); 15 ng/mL still 2× more sensitive than ECL (Electrochemiluminescence) assay.

FIG. 6 shows that no carryover in a carryover assessment, confirming concentration of reagents and parameters.

FIG. 7 shows summary comparison.

Example 3. Prior Art Free C5 Assay Using Meso Scale Discovery® Electrochemiluminescence Technology Prior art free C5 assays have shown to have limitations. An example is shown below.

This prior art free C5 assay is designed to quantify free C5 complement protein in human serum samples using Meso Scale Discovery® electrochemiluminescence technology. Eculizumab is conjugated to biotin and immobilized on a streptavidin coated MSD® 96-well assay plate. Assay standard curve samples are prepared by serial dilution of purified human C5 in C5 depleted serum and added to the plate along with test and quality control samples. Captured C5 on the immobilized eculizumab is detected using N19-8 conjugated to a MSD® SulfoTag, which binds to a different epitope on C5 than that bound by eculizumab. The N19-8-Tag emits light as an ECL signal upon electrochemical stimulation initiated at the electrode surface of the assay plate. The intensity of the signal is proportional to the amount of C5 captured. The ECL signal of the captured complex is measured using the MSD® Sector Imager 2400. A weighted 4-parameter curve fit standard curve is generated by plotting the ECL signal of the standard samples on the y-axis against the corresponding C5 concentration on the x-axis. The concentration of C5 in each serum sample can be determined by interpolating the ECL signals of samples with readings in the linear range of the standard curve to the standard curve of known C5 concentrations. The mean of triplicate wells for each standard curve dilution, QC samples, and patient samples is calculated and reported.

This assay has been found to have certain limitations for measuring free C5 in the presence of eculizumab. A consistent bias was noted between measured free C5 concentration compared to theoretical calculation based on eculizumab to C5 binding molar ratio (1:2.53). This bias leads to an overestimation of free C5 even at high concentrations of eculizumab (35-2000 µg/mL). Therefore, an experiment was performed to assess the limitations of the assay by spiking 35 µg/mL eculizumab against various C5 concentrations. The results clearly demonstrated a bias between measured free C5 concentration and theoretical free C5 concentration. This bias may be introduced by dissociation between eculizumab and C5 in the test sample during assay procedures. Certain assay conditions are determined to shift the binding equilibrium towards dissociation based on Le Chatelier's principle.

Assay Modification and Rationale

Using the same assay platform, four major modifications were implemented into the new C5 assay as summarized in the table below:

TABLE 6

Modifications to Old Free C5 Assay

| Assay Modification | Old Free C5 Assay | New Free C5 Assay | Rationale |
|---|---|---|---|
| Lower Sample Dilution | 1:1000 | 1:2 | Minimize dilutional effect on original sample equilibrium based on Le Chatelier's principle |
| Lower Sample Preparation Temperature | Room Temp | On Ice | Slow down eculizumab-C5 dissociation in the sample |
| Shorter Sample Incubation Time | 60 minutes | 15 minutes | Reduce time eculizumab-C5 dissociation in the sample |
| Higher Coating Concentration | 500 ng/mL | 5 µg/mL | Increase the rate of capturing free C5, and shorten incubation time |

Results

With the four modifications, additional experiments were performed to compare old and new free C5 assay in terms of assay accuracy. Theoretically calculated free C5 concentrations were produced to illustrate the target concentration we expected to see in a human body. Various concentrations of eculizumab were spiked into pooled normal human serum and measured on both old and new free C5 assay. The results strongly suggest that the new free C5 assay provided much more accurate results as compared to the theoretical values. Additionally, the results, confirmed by several different analysts, demonstrated the accuracy, precision and robustness of the assay. All results are within the range of the assay (0.0016 to 20 µg/mL) with precision of ≤25% CV.

TABLE 7

Old VS. New C5 Assay Results Comparison

| | Measured Free C5 Concentration in NHS | | Theoretical | | |
|---|---|---|---|---|---|
| Spiked eculizumab (µg/mL) | Old Free C5 Assay (µg/mL) | New Free C5 Assay (µg/mL) | Free C5 Concentration* (µg/mL) | % Bias Old VS. Theoretical | % Bias New VS. Theoretical |
| 2000 | 0.56 | 0.002 | 0.001 | 55900 | 100 |
| 1000 | 1.16 | 0.003 | 0.001 | 115900 | 200 |
| 500 | 2.37 | 0.005 | 0.003 | 78900 | 67 |
| 250 | 4.77 | 0.009 | 0.005 | 95300 | 80 |
| 125 | 8.62 | 0.013 | 0.011 | 78264 | 18 |
| 62.5 | 16.4 | 0.028 | 0.027 | 60641 | 4 |
| 31.3 | 35.1 | 0.19 | 0.19 | 18374 | 0 |
| 15.6 | 74.9 | 30.4 | 30.4 | 146 | 0 |
| 9.4 | 96.4 | 42.6 | 46.2 | 109 | −8 |
| 5 | 101.4 | 58.2 | 57.3 | 77 | 2 |
| 1 | 119.3 | 68.5 | 67.5 | 77 | 1 |
| 0 | 113.2 | 77.5 | 70 | 62 | 11 |

*Theoretical concentration calculated based on binding stoichiometry using an average human C5 concentration of 70 µg/mL in physiological buffer.

Conclusion

The modifications of old free C5 assay have resulted in improvements in assay accuracy by minimizing the effects of eculizumab-C5 dissociation. The % bias increases with increasing eculizumab concentration, compared to the theoretical % free C5, at concentrations 250 µg/mL. Serum free C5 results at eculizumab concentrations 250 µg/mL, with the new assay, should therefore be interpreted with caution. However, these very low levels of free C5 concentrations are not expected to initiate hemolysis in clinical samples.

Because of the improved performance of the new serum free C5 assay compared to the old assay, Switch from eculizumab coated plate to ALXN1210 coated plate is adapted to ensure the assay is more reflective of free C5 measurement in ALXN1210 serum samples.

Example 4. Assay for the Quantification of C5a in Human Plasma Using the GyroLab Platform This study validated a Gyros assay to measure free C5a in Human Plasma. This assay employed the GyroLab platform and used a biotinylated antibody (ALXN1007) to capture free C5a and an Alexa 647 labeled anti C5a antibody to detect C5a in human plasma. The study demonstrated that the method is suitable for its intended purpose of quantifying C5a in human plasma.

Abbreviations
BPM: Bioanalytical Project Manager
CV: Coefficient of Variation
C5a: Complement Factor 5a
Low VS: Low Validation Sample
Mid VS: Mid Validation Sample
High VS: High Validation Sample
LLOQ: Lower Limit of Quantitation
ULOQ: Upper Limit of Quantification
BLQ: Below Limit of Quantification
ALQ: Above the Limit of Quantification
MRD: Minimum Required Dilution
PBST: Phosphate Buffer Saline, 0.01% Tween
C5a DesArg purified human complement protein at 0.51 mg/ML is used as reference standard.

A freshly prepared quantification standard curve consisting of 11 non-zero standards was spiked with C5a, diluted into Rexxip AN buffer and was included on all CDs tested. A Blank was also tested and included on all CDs. The concentrations of C5a were 60, 30, 15, 7.5, 3.75, 1.88, 0.938, 0.469, 0.234, 0.117, and ng/mL. The 0.059 ng/mL and 0.117 ng/mL data points were evaluated as anchor points. All calibration standards were diluted 2-fold into assay diluent before testing and were tested in duplicate on each CD tested. The Gyrolab XP performed the duplicates by adding sample twice from the same well. The data was fit to a five-parameter logistical curve regression model within the Gyros data analysis software.

Validation control samples representing an Upper Limit (ULOQ), High (High-VS), Mid (Mid-VS), Low (Low-VS) and 2 Lower limit (LLOQ-1 and LLOQ-2) concentrations of the biomarker C5a were prepared by spiking C5a into Rexxip AN at levels to assess the quantification range. A Blank, consisting of Rexxip AN, was used for all assays. One set of each ULOQ, High VS, Mid-VS, Low-VS, LLOQ-1 and LLOQ-2, and a Blank was included on each CD during validation. All controls were prepared fresh and diluted 2-fold into assay diluent. C5a was spiked at the following concentrations.

ULOQ=40 ng/mL
High VS=20 ng/mL
Mid-VS=2.5 ng/mL
Low VS=0.625 ng/mL
LLOQ-1=0.200 ng/mL
LLOQ-2=0.156 ng/mL To remove C5, endogenous samples (Individuals 2 and 11) were subjected to Dynabead treatment, included on all CDs and tested in duplicate to access the utility of using the samples for trending purposes.

General Assay Procedure

The C5a quantification curve and validation control samples were prepared and diluted in a PCR plate containing Rexxip AN buffer then subsequently diluted to an MRD of 2 in assay diluent (1M NaCl+0.5% Tween).

Samples used for the validation assessment may be subjected to incubation with anti-C5 antibody coupled to magnetic beads for a minimum of 1 hour with rapid shaking to remove C5. For those samples, 10 uL of sample was added to 20 uL of anti C5 coupled beads and incubated with vigorous shaking for 1 hour. After incubation with shaking, the plate was subjected to a plate based magnet for a minimum of 2 minutes to separate the beads from the solution. 10 uL of sample was carefully removed without disturbing the bead pellet and added to a PCR plate according to the Gyros loading list. The final MRD for the samples is 3 and the dilution factor on the Gyros loading list is 1.5.

Biotinylated ALXN1007 (capture antibody) was prepared at 100 ug/mL in PBST and added to the PCR plate according to the Gyro Lab loading list. Alexa 647 labeled anti-C5a (detection antibody) was prepared at 4 ug/ml in Rexxip F buffer and added to the PCR plate according to the Gyro Lab loading list.

Alexa 647 labeled anti-C5a/C5a des-Arg purified human complement protein is a mouse IgG2a mAb, labeled at 4.2 moles of Alexa Fluor® 647 dye per mole antibody.

Method Validation

Method validation of the assay included intra and inter-assay precision and accuracy, calibration curve response and range, dilutional linearity, selectivity, parallelism, short term stability, long term stability, freeze thaw stability and process stability. During validation, runs were accepted based on the acceptance criteria stated for the calibration curve. A summary of all runs performed during validation is shown in Table 8.

TABLE 8

Run Summary

| Run # | Description | Status/Comment |
|---|---|---|
| Run 1 | A&P Selectivity 1-5 & Fresh Stability | Failed due to High CV STD curve |
| Run 2 | A&P Dilutional Linearity & Prozone | Failed due to High CV STD curve |
| Run 3 | A&P Selectivity 1-5 & Fresh Stability | Passed, Repeat of Run 1 |
| Run 4 | A&P Parallelism | Passed, Repeat of Run 2 |
| Run 5 | A&P Dilutional Linearity & Prozone | Passed |
| Run 6 | A&P Selectivity 6-10 & Freeze Thaw 3 | Passed |
| Run 7 | A&P Intra/Inter Process Stability | Passed |
| Run 8 | A&P Short term Stability & Freeze Thaw 6 | Passed |
| Run 9 | A&P Parallelism & Dilutional Linearity | Passed, Repeat of High CV samples |

Calibration Curve Range

To evaluate precision and accuracy of the standard curve, each run for validation contained a standard curve consisting of nine non-zero standards and two anchor points, defined in section 15. The inclusion or exclusion of anchor points was based on the fitting of the curve within the quantifiable range of the curve. A zero (no analyte) blank was included in each assay but was not included in the fitting of the curve. All points were tested in duplicate on seven separate runs by two analysts and the standard curve was calculated using a 5-parameter logistic curve fit within the Gyro Lab Evaluator software.

Precision, represented by the coefficient of variation (CV) expressed as a percent, was calculated using the following expression:

$$CV(\%) = \frac{\text{Standard deviation of the mean of individual measurements}}{\text{Mean of individual measurements}} \times 100$$

% Relative Error (% RE), was calculated using the following expression, where the nominal concentration is equal to the concentration of reference standard spiked into the matrix:

$$\% RE = \frac{(\text{Measured concentration} - \text{Nominal concentration})}{\text{Nominal concentration}} \times 100$$

The total error of the assay was assessed using the following equation:

$$\% TE = \text{absolute } \% RE + \% CV$$

Target Acceptance Criteria: A minimum of 75% of the non-zero standards must have a mean back calculated concentration (BCC) equal to or within ±20% of the nominal value, except at the lowest and highest standards where the mean BCC can be equal to or within ±25%. The CV for each standard must be equal to or less than 20%, except at the lowest and highest standards where the CV may be ≤25%.

All nine non-zero calibration standards met the acceptance criteria at all levels tested, with recoveries ranging from 99.2-109.2% and precision that ranged from 1.5-13.1% CV. The relative error was between 0.4-9.2% RE with total error ranging from 2.1-22.3% TE. The two lowest calibrator concentrations of 0.117 ng/mL and 0.059 ng/mL are used as anchor points during sample analysis and will be included or excluded from analysis based on the fit of the curve. The calibration curve range for the assay was 0.234-60 ng/mL. Data is shown in Table 9.

TABLE 9

| | | | | Calibration Curve Range | | | |
|---|---|---|---|---|---|---|---|
| Standard | Expected Conc (ng/mL) | Run 3 Mean Calc Conc (ng/mL) | Run 5 Mean Calc Conc (ng/mL) | Run 6 Mean Calc Conc (ng/mL) | Run 9 Mean Calc Conc (ng/mL) | Run 4 Mean Calc Conc (ng/mL) | Run 7 Mean Calc Conc (ng/mL) |
| Std 1 | 60 | 64.3 | 59.9 | 60.3 | 60.4 | 59.2 | 60.8 |
| Std 2 | 30 | 29.6 | 30.3 | 29.7 | 29.6 | 30.0 | 29.1 |
| Std 3 | 15 | 16.3 | 14.7 | 15.1 | 15.0 | 16.0 | 16.2 |
| Std 4 | 7.5 | 7.75 | 8.11 | 7.52 | 7.87 | 8.32 | 7.14 |
| Std 5 | 3.75 | 3.64 | 3.45 | 3.89 | 3.87 | 3.64 | 3.98 |
| Std 6 | 1.88 | 1.93 | 2.03 | 1.81 | 1.80 | 1.87 | 1.80 |
| Std 7 | 0.938 | 0.947 | 0.920 | 0.918 | 0.951 | 0.969 | 0.930 |
| Std 8 | 0.469 | 0.501 | 0.499 | 0.474 | 0.511 | 0.454 | 0.514 |
| Std 9 | 0.234 | 0.325 | 0.250 | 0.249 | 0.237 | 0.266 | 0.222 |
| Std 10 | 0.117 | 0.108 | 0.083 | 0.114 | 0.110 | 0.123 | 0.116 |
| Std 11 | 0.059 | 0.103 | 0.095 | 0.060 | Masked | 0.047 | 0.066 |

| | Run 8 | Grand Mean, CV and Recovery | | | | |
|---|---|---|---|---|---|---|
| Standard | Mean Calc Conc (ng/mL) | Mean Calc Conc (ng/mL) | % CV | % Recovery | % RE | % TE |
| Std 1 | 60.4 | 60.8 | 2.7 | 101.3 | 1.3 | 4.0 |
| Std 2 | 30.3 | 29.8 | 1.5 | 99.4 | 0.6 | 2.1 |
| Std 3 | 14.7 | 15.4 | 4.6 | 102.7 | 2.7 | 7.3 |
| Std 4 | 8.31 | 7.86 | 5.5 | 104.8 | 4.8 | 10.3 |
| Std 5 | 3.56 | 3.72 | 5.3 | 99.2 | 0.8 | 6.1 |
| Std 6 | 1.87 | 1.87 | 4.4 | 99.6 | 0.4 | 4.8 |
| Std 7 | 0.976 | 0.944 | 2.4 | 100.7 | 0.7 | 3.1 |
| Std 8 | 0.453 | 0.487 | 5.3 | 103.8 | 3.8 | 9.1 |
| Std 9 | 0.240 | 0.256 | 13.1 | 109.2 | 9.2 | 22.3 |
| Std 10 | 0.128 | 0.112 | 13.0 | 95.6 | 4.4 | 17.4 |
| Std 11 | 0.052 | 0.071 | 32.8 | 119.5 | 19.5 | 52.4 |

Quantifiable Range (Assay Range), Accuracy and Precision

To evaluate the quantifiable range and assay accuracy and precision, each run contained controls.

For intra-assay precision each control was tested one time in replicates of six by one analyst over 1 run. The intra-assay precision run met acceptance criteria for all controls tested. Recoveries ranged for 96.3 to 111.7% with precision that ranged from 2.3 to 20.2% CV. Relative Error ranged from 0.0 to 10.5% and Total Error ranged from 6.6 to 25.3%. Data are shown in Table 10.

TABLE 10

Intra-assay Precision

| Sample | Expected Conc (ng/mL) | Replicate Calc Conc (ng/mL) | | | | | | Mean Calc Conc (ng/mL) | % CV | % Recovery | % RE | % TE |
|---|---|---|---|---|---|---|---|---|---|---|---|---|
| | | 1 | 2 | 3 | 4 | 5 | 6 | | | | | |
| ULOQ | 40.0 | 41.7 | 39.9 | 35.1 | 37.8 | 38.9 | 37.7 | 38.5 | 5.8 | 96.3 | 3.8 | 9.6 |
| High-VS | 20.0 | 19.5 | 20.3 | 22.3 | 18.6 | 20.3 | 19.0 | 20.0 | 6.6 | 100.0 | 0.0 | 6.6 |
| Mid-VS | 2.50 | 2.38 | 2.46 | 2.98 | 2.84 | 2.77 | 2.70 | 2.69 | 8.5 | 107.5 | 7.0 | 15.4 |
| Low-VS | 0.625 | 0.727 | 0.679 | 0.700 | 0.695 | 0.694 | 0.693 | 0.698 | 2.3 | 111.7 | 10.5 | 12.8 |
| LLOQ-1 | 0.200 | 0.264 | 0.232 | 0.148 | 0.222 | 0.191 | 0.178 | 0.206 | 20.2 | 103.0 | 2.9 | 23.1 |
| LLOQ-2 | 0.156 | 0.210 | 0.173 | 0.192 | 0.177 | 0.150 | 0.137 | 0.173 | 15.4 | 111.0 | 9.9 | 25.3 |

Target Acceptance Criteria: For accuracy, the mean calculated concentration for each control must be equal to or within ±25% of the nominal value, except at the LLOQ and ULOQ, where the mean calculated concentration can be equal to or within ±30% of the nominal value. For precision, the CV for each control must be ≤25%, except at the LLOQ and ULOQ, where the CV is ≤30%. The LLOQ of the assay is the lowest control with acceptable precision and accuracy, and the ULOQ of the assay is the highest control with acceptable precision and accuracy. The total error must be ≤40%.

For inter-assay precision each control was tested over seven in runs in duplicate by two analysts. The first two replicates of the intra-assay assessment (Run 7) were included as one inter-assay assessment. Intra-assay precision criteria was met for all controls tested. Recoveries ranged from 96.4 to 116.6% with precision that ranged from 2.0 to 20.5% CV. Relative Error ranged from 1.4 to 16.6% and Total Error ranged from 3.4 to 34.0%. Data are shown in Table 11.

TABLE 11

Inter-assay Precision

| Sample | Expected Conc (ng/mL) | Run 3 Mean Calc Conc (ng/mL) | Run 5 Mean Calc Conc (ng/mL) | Run 6 Mean Calc Conc (ng/mL) | Run 9 Mean Calc Conc (ng/mL) | Run 4 Mean Calc Conc (ng/mL) | Run 7 Mean Calc Conc (ng/mL) |
|---|---|---|---|---|---|---|---|
| ULOQ | 40 | 37.8 | 36.9 | 37.8 | 38.6 | 39.1 | 40.8 |
| HQC | 20 | 20.8 | 19.7 | 20.2 | 20.2 | 20.8 | 19.9 |
| MQC | 2.5 | 2.79 | 2.44 | 2.61 | 2.90 | 2.87 | 2.42 |
| LQC | 0.625 | 0.674 | 0.619 | 0.621 | 0.698 | 0.618 | 0.703 |
| LLOQ1 | 0.200 | 0.248 | 0.277 | 0.176 | 0.244 | 0.224 | 0.248 |
| LLOQ2 | 0.156 | 0.209 | 0.193 | 0.154 | 0.174 | 0.108 | 0.192 |

| | Run 8 | Grand Mean, CV and Recovery | | | | |
|---|---|---|---|---|---|---|
| Sample | Mean Calc Conc (ng/mL) | Mean Calc Conc (ng/ml) | % CV | % Recovery | Relative Error | Total Error |
| ULOQ | 38.9 | 38.5 | 3.3 | 96.4 | 3.6 | 6.9 |
| HQC | 20.5 | 20.3 | 2.0 | 101.4 | 1.4 | 3.4 |

TABLE 11-continued

| | | Inter-assay Precision | | | | |
|---|---|---|---|---|---|---|
| MQC | 2.68 | 2.67 | 7.3 | 106.9 | 6.9 | 14.2 |
| LQC | 0.632 | 0.652 | 5.9 | 104.3 | 4.3 | 10.2 |
| LLOQ1 | 0.216 | 0.233 | 13.7 | 116.6 | 16.6 | 30.3 |
| LLOQ2 | 0.210 | 0.177 | 20.5 | 113.5 | 13.5 | 34.0 |

Mean Calc Conc = mean calculated concentration

Target Acceptance Criteria: For accuracy, the mean calculated concentration for each control must be equal to or within ±25% of the nominal value, except at the LLOQ and ULOQ, where the mean calculated concentration can be equal to or within ±30% of the nominal value. For precision, the CV for each control must be ≤25%, except at the LLOQ and ULOQ, where the CV is ≤30%. The LLOQ of the assay is the lowest control with acceptable precision and accuracy, and the ULOQ of the assay is the highest control with acceptable precision and accuracy. The total error must be ≤40%.

Dilutional linearity and minimum required dilution (MRD) were evaluated in four individual lots of matrix. Matrices were spiked with reference standard above the ULOQ at 100 ng/mL and diluted 4 fold 3 times in assay diluent then treated with anti C5 coupled magnetic beads to remove any contaminating C5. Dilutional linearity samples were evaluated one time over two runs and tested in duplicate by one analyst. Individual-13 from run 5 was re-evaluated in run 9 due high CV associated with the 64 fold dilution. The assay demonstrates dilution linearity with the four lots of spiked matrix with all dilutions for all lots meeting acceptance criteria. The maximum dilution is 64 fold. The recovery for each dilution when corrected for dilution ranged from 94.0 to 117% with CVs that ranged from 0.8 to 11.1%. The minimum required dilution for plasma samples as required by bead treatment is three. Samples that are ALQ with the standard bead treatment MRD can be diluted up to 64 fold to obtain results that are within the quantifiable range of the assay. Data is shown in Table 11.

Target Acceptance Criteria: For dilutional linearity, the mean concentrations of dilutions that fall within the quantifiable range, when corrected for dilution, must be equal to or within 25% of the nominal value and have CVs ≤25%. The largest dilution in any of the samples that meets the acceptance criteria is the maximum allowed sample dilution.

TABLE 11

| | | Dilutional Linearity | | | | | | |
|---|---|---|---|---|---|---|---|---|
| | | Run 5 | | | | | | |
| | | IND-6 BRH1240220 (male) | | | | IND-7 BRH1240220 (male) | | |
| Dilution | Expected Conc (ng/mL) | Ave Calc Conc (ng/mL) | % CV | Corrected Conc (ng/mL) | % recovery | Ave Calc Conc (ng/mL) | % CV | Corrected Conc (ng/mL) | % recovery |
| 1 | 100 | ALQ | N/A | ALQ | N/A | ALQ | NA | ALQ | N/A |
| 4 | 25 | 26.7 | 4.7 | 106.7 | 106.7 | 29.3 | 8.5 | 117.2 | 117.2 |
| 16 | 6.25 | 6.69 | 0.8 | 107.1 | 107.1 | 7.27 | 3.6 | 116.3 | 116.3 |
| 64 | 1.56 | 1.67 | 5.0 | 106.9 | 106.9 | 1.67 | 1.9 | 106.6 | 106.6 |
| 0 | 0 | BLQ | N/A | BLQ | N/A | BLQ | N/A | BLQ | N/A |

| | Run 5 | | | | Run 9 | | | |
|---|---|---|---|---|---|---|---|---|
| | IND-17 BRH12402231 (female) | | | | IND-13 BRH12402227 (female) | | | |
| Dilution | Ave Calc Conc (ng/mL) | % CV | Corrected Conc (ng/mL) | % Recovery | Ave Calc Conc (ng/mL) | % CV | Corrected Conc (ng/mL) | % recovery |
| 1 | ALQ | N/A | ALQ | N/A | ALQ | N/A | ALQ | N/A |
| 4 | 28.1 | 11.1 | 112.3 | 112.3 | 26.2 | 10.0 | 104.7 | 104.7 |
| 16 | 7.3 | 10.1 | 116.4 | 116.4 | 6.5 | 2.6 | 104.3 | 104.3 |
| 64 | 1.6 | 7.2 | 103.8 | 103.8 | 1.5 | 2.6 | 94.0 | 94.0 |
| 0 | BLQ | N/A | BLQ | N/A | BLQ | N/A | BLQ | N/A |

ALQ = above the limit of quantification
BLQ = below the limit of quantification
N/A = a value could not be calculated The prozone (Hock Effect) was evaluated in matrix spiked at 500 ng/mL. Prozone was evaluated one time in duplicate by one analyst. The sample was treated with anti C5 coupled magnetic beads. The calculated response was greater than the quantifiable range of the assay and demonstrated that no prozone (hook effect) was observed. Data are shown in Table 12.

TABLE 12

Prozone (Hook Effect)

| Sample | Spiked Concentration (ng/ml) | Calc Conc (ng/mL) | Mean Response RFU | % CV |
|---|---|---|---|---|
| Prozone | 500 | >90 | 168 | 1.7 |

The prozone effect is demonstrated if the observed response is within or below the quantifiable range of the assay for a sample whose nominal concentration is above the ULOQ.

Assay selectivity was evaluated by spiking ten individual lots of matrix with C5a at 5, 1, and 0.3 ng/mL and subsequently treating with anti C5 antibody coupled magnetic beads. An un-spiked sample of each individual was also evaluated. Lots that were shown to contain low levels of C5a during pre-qualification were selected. Selectivity samples were evaluated one time in duplicate over 2 runs by one analyst. The assay met target acceptance criteria for selectivity. Eight out of ten spiked individuals when corrected for endogenous C5a recovered within 25% of the nominal value. Data are shown in Table 13.

Target Acceptance Criteria: A minimum of 80% of the spiked matrices must be equal to or within ±25% of the nominal value.

TABLE 13

Selectivity

| Sample | Expected Conc (ng/mL) | Ave Calc Conc (ng/mL) | % CV | Endogenous subtracted | % recovery |
|---|---|---|---|---|---|
| IND-1 | 5 | 5.10 | 2.6 | 4.50 | 90.1 |
| BRH1240215 | 1 | 1.38 | 0.3 | 0.784 | 78.4 |
| (male) | 0.3 | 0.757 | 17.1 | 0.157 | 52.2 |
|  | 0 | 0.601 | 2.9 | 0.000 | N/A |
| IND-6 | 5 | 5.68 | 18.1 | 5.16 | 103.2 |
| BRH1240220 | 1 | 1.54 | 5.0 | 1.022 | 102.2 |
| (male) | 0.3 | 0.783 | 9.5 | 0.264 | 87.9 |
|  | 0 | 0.519 | 1.5 | 0.000 | N/A |

TABLE 13-continued

Selectivity

| Sample | Expected Conc (ng/mL) | Ave Calc Conc (ng/mL) | % CV | Endogenous subtracted | % recovery |
|---|---|---|---|---|---|
| IND-7 | 5 | 5.80 | 9.1 | 5.51 | 110.2 |
| BRH1240221 | 1 | 1.43 | 15.0 | 1.137 | 113.7 |
| (male) | 0.3 | 0.539 | 16.6 | 0.250 | 83.2 |
|  | 0 | 0.289 | 21.5 | 0.000 | N/A |
| IND-13 | 5 | 5.64 | 0.3 | 5.30 | 105.9 |
| BRH1240227 | 1 | 1.30 | 13.7 | 0.957 | 95.7 |
| (female) | 0.3 | 0.667 | 2.8 | 0.322 | 107.4 |
|  | 0 | 0.345 | 11.8 | 0.000 | N/A |
| IND-17 | 5 | 5.47 | 0.1 | 5.17 | 103.5 |
| BRH1240231 | 1 | 1.16 | 6.8 | 0.861 | 86.1 |
| (female) | 0.3 | 0.546 | 3.8 | 0.252 | 83.9 |
|  | 0 | 0.294 | 8.7 | 0.000 | N/A |
| IND-20 | 5 | 5.41 | 0.3 | 4.84 | 96.7 |
| BRH1240234 | 1 | 1.44 | 1.7 | 0.865 | 86.5 |
| (female) | 0.3 | 0.723 | 5.0 | 0.145 | 48.4 |
|  | 0 | 0.578 | 1.3 | 0.000 | N/A |
| IND-18 | 5 | 6.00 | 2.0 | 5.47 | 109.4 |
| BRH1240232 | 1 | 1.67 | 0.0 | 1.136 | 113.6 |
| (female) | 0.3 | 0.791 | 0.5 | 0.256 | 85.5 |
|  | 0 | 0.535 | 3.9 | 0.000 | N/A |
| IND-19 | 5 | 6.37 | 5.1 | 6.05 | 121.1 |
| BRH1240233 | 1 | 1.44 | 2.6 | 1.119 | 111.9 |
| (female) | 0.3 | 0.658 | 2.3 | 0.339 | 113.0 |
|  | 0 | 0.319 | 4.6 | 0.000 | N/A |
| IND-3 | 5 | 6.46 | 3.4 | 5.82 | 116.4 |
| BRH1240217 | 1 | 1.76 | 0.8 | 1.110 | 111.0 |
| (female) | 0.3 | 0.875 | 8.5 | 0.230 | 76.5 |
|  | 0 | 0.646 | 5.7 | 0.000 | N/A |
| IND-8 | 5 | 5.61 | 0.2 | 5.10 | 102.0 |
| BRH1240222 | 1 | 1.55 | 7.1 | 1.042 | 104.2 |
| (female) | 0.3 | 0.808 | 3.2 | 0.295 | 98.4 |
|  | 0 | 0.513 | 4.4 | 0.000 | N/A |

N/A = a value could not be calculated
IND = individual

Parallelism

Six individuals (3 males and 3 females) shown to have endogenous detectable levels of C5a during pre-qualification were selected to assess parallelism. Samples were subjected to 3 two-fold serial dilutions in assay diluent then subjected to bead treatment with anti C5 coupled magnetic beads. Parallelism samples were evaluated over 2 runs by 2 analysts. Four out of the six individuals that were tested in Run 4 were repeated in Run 9 due to high sample CVs. The assay demonstrated a lack of parallelism and underscores the relative quantitative nature of the assay, but does not preclude it from use. Samples CV's ranged from 0.1% to 27.1%. Data are shown in Table 14.

TABLE 14

Parallelism

| | Run 9 | | | | | | | | | Run 4 | | | |
|---|---|---|---|---|---|---|---|---|---|---|---|---|---|
| | Individual 2 BRH1240216 (Male) | | Individual 4 BRH1240218 (Male) | | Individual 5 BRH1240219 (Male) | | Individual 16 BRH1240230 (Female) | | Individual 11 BRH1240230 (Female) | | Individual 14 BRH1240227 (Female) | |
| Fold dilution | Ave Conc (ng/mL) | % CV | Ave Conc (ng/mL) | % CV | Ave Conc (ng/mL) | % CV | Ave Conc (ng/mL) | % CV | Ave Conc (ng/mL) | % CV | Ave Conc (ng/mL) | % CV |
| Neat | 1.45 | 1.9 | 0.801 | 11.6 | 2.41 | 4.0 | 0.588 | 0.1 | 5.39 | 12.1 | 0.683 | 8.5 |
| 2 | 0.507 | 11.7 | 0.500 | 22.1 | 0.686 | 4.3 | 0.402 | 27.1 | 9.63 | 3.5 | N/A | N/A |
| 4 | 0.411 | 19.9 | N/A | N/A | 0.412 | 13.7 | N/A | N/A | 7.41 | 9.6 | N/A | N/A |
| 8 | N/A | N/A | N/A | N/A | N/A | N/A | N/A | N/A | 4.30 | 3.2 | N/A | N/A |

N/A = a value could not be calculated

Stability

The stability of samples subjected to short-term storage at approximately 4° C. and at room temperature, long-term storage at the intended storage temperature, and several freeze and thaw cycles were investigated. Matrix spiked with a high (5 ng/mL) and low concentration (1 ng/mL) of C5a was used for stability assessment. Multiple aliquots of the stability samples were prepared for storage at the intended storage temperature, (−80° C.), room temperature, approximately 4° C., and for freeze/thaw experiments. One aliquot at each level was analyzed immediately as the fresh control sample (Reference condition). The remaining samples were tested after the specified storage period and condition. All stability assessments included a freshly prepared standard curve and validation samples to assess the assay acceptability. All stability samples were treated with anti C5 antibody coupled magnetic beads. Process stability was also evaluated.

Short Term Stability

Aliquots of the low and high stability samples were thawed and stored at room temperature for 2 hours and 20 minutes, and at approximately 4° C. for up to 23 hours and 29 minutes. All short term stability samples were run in replicates of six. The stability samples met the acceptance criteria for short term stability. The samples for each condition were within 30% of the reference standard and the CVs ranged from 4.6 to 11.6%. Data are shown in Table 15.

TABLE 15

Short Term Stability

| Sample | Condtion | Time | Replicate Calc Conc (ng/mL) | | | | | | Mean Calc Conc (ng/mL) | % CV | % of Reference |
| --- | --- | --- | --- | --- | --- | --- | --- | --- | --- | --- | --- |
| | | | 1 | 2 | 3 | 4 | 5 | 6 | | | |
| High Stability | Reference condition | 0 Hrs | 5.07 | 6.16 | 5.91 | 5.32 | 5.62 | 5.70 | 5.63 | 7.0 | N/A |
| | Room Temperature | 2 hr 20 min | 5.69 | 4.16 | 4.93 | 5.58 | 4.65 | 5.24 | 5.04 | 11.6 | 89.6 |
| | 2-8° C. | 23 hrs and 29 min | 5.51 | 5.39 | 5.10 | 5.49 | 4.92 | 5.47 | 5.31 | 4.6 | 94.4 |
| Low Stability | Reference condition | 0 Hrs | 1.27 | 1.26 | 1.13 | 1.19 | 1.18 | 1.24 | 1.21 | 4.6 | N/A |
| | Room Temperature | 2 hr 20 min | 0.904 | 0.971 | 1.01 | 1.03 | 0.867 | 0.949 | 0.955 | 6.5 | 78.8 |
| | 2-8° C. | 23 hrs and 29 min | 0.875 | 0.984 | 0.875 | 0.788 | 0.954 | 0.936 | 0.902 | 7.8 | 74.4 |

N/A = value not calculated

Target Acceptance Criteria: The mean calculated concentration for each short-term stability sample must be equal to or within ±30% of the value of the fresh control sample and have a CV 30%.

Long term stability will be evaluated at 1, 3, 6, 9, 12, 18, 21 and 24 months. Aliquots of the low and high concentration stability samples were prepared and stored at the appropriate temperature (−80° C.). All long-term stability samples will be run, at minimum, in replicates of six. The validation report will be amended to include the long-term stability data.

Target Acceptance Criteria: The mean calculated concentration for each long-term stability sample must be equal to or within ±30% of the value of the fresh control sample and have a CV Freeze and Thaw Stability Aliquots of the low and high concentration stability samples were subjected to 6 freeze and thaw cycles at approximately −80° C. The stability samples were thawed at room temperature for at least one hour and then re-frozen for a minimum of 12 hours before being subjected to a new cycle. Assessment of freeze and thaw stability was conducted on samples that completed three and six freeze/thaw cycles. All freeze and thaw stability samples were tested in replicates of six. The stability samples met the acceptance criteria for freeze and thaw stability. The samples for each condition were within 30% of the reference standard and the CVs ranged from 1.4 to 8.1%. Data are shown in Table 16.

TABLE 16

Freeze Thaw Stability

| Sample | Condition | Replicate Calc Conc (ng/mL) | | | | | | Mean Calc Conc (ng/mL) | % CV | % of Reference |
|---|---|---|---|---|---|---|---|---|---|---|
| | | 1 | 2 | 3 | 4 | 5 | 6 | | | |
| High Stability | Reference condition | 5.07 | 6.16 | 5.91 | 5.32 | 5.62 | 5.70 | 5.63 | 7.0 | N/A |
| | Freeze Thaw Cycle 3 | 5.98 | 5.94 | 5.86 | 5.80 | 5.77 | 5.92 | 5.88 | 1.4 | 104.5 |
| | Freeze Thaw Cycle 6 | 4.84 | 5.14 | 4.73 | 4.82 | 5.08 | 4.53 | 4.86 | 4.6 | 86.3 |
| Low Stability | Reference condition | 1.27 | 1.26 | 1.13 | 1.19 | 1.18 | 1.24 | 1.21 | 4.6 | N/A |
| | Freeze Thaw Cycle 3 | 1.01 | 1.16 | 1.06 | 1.16 | 0.994 | 1.03 | 1.07 | 6.9 | 88.0 |
| | Freeze Thaw Cycle 6 | 0.930 | 1.06 | 1.03 | 0.840 | 0.977 | 0.988 | 0.971 | 8.1 | 80.1 |

N/A = value not calculated

Target Acceptance Criteria: The mean calculated concentration for each freeze and thaw stability sample must be equal to or within ±30% of the value of the fresh control sample and have a CV that is 30%.

Process Stability (Robustness)

Process stability was evaluated by preparing a standard curve, QC's and capture and detection reagents that were then split into in two assay-ready PCR plates. The endogenous samples were also included for each time point. The plates were sealed and placed on the deck of the Gyros Instrument. Each plate was evaluated at time 0 hours and 2 hours using one disk per plate. The standard curves met acceptance criteria for both time points tested. The grand mean % recovery for nine zero standards ranged from 96.8 to 104.4% with CV's that ranged from 0.4 to 8.3%. The grand mean recovery for the QC's ranged from 98.3 to 118.3% with CV's that ranged from 1.5 to 18%. Data for the standard curves and QC's tested for each time point are shown in Table 17. Data for the endogenous samples are shown in Table 18. The assay demonstrates process stability for up to 2 hours.

TABLE 17

Process Stability Standards and QC's

| Sample | Expected Conc (ng/mL) | 0 hours | | | 2 hours | | | Grand Mean, CV and Recovery | | |
|---|---|---|---|---|---|---|---|---|---|---|
| | | Average Conc (ng/mL) | % CV | % Recovery | Average Conc (ng/mL) | % CV | % Recovery | Mean Conc (ng/mL) | % CV | % Recovery |
| STD1 | 60 | 60.8 | 3.5 | 101.4 | 60.4 | 2.1 | 100.7 | 60.6 | 0.5 | 101.1 |
| STD2 | 30 | 29.1 | 5.0 | 97.1 | 29.7 | 2.3 | 99.1 | 29.4 | 1.5 | 98.1 |
| STD3 | 15 | 16.2 | 5.9 | 107.7 | 15.0 | 4.1 | 100.0 | 15.6 | 5.2 | 103.9 |
| STD4 | 7.5 | 7.14 | 3.8 | 95.2 | 7.65 | 6.3 | 102.1 | 7.40 | 4.9 | 98.6 |
| STD5 | 3.75 | 3.98 | 4.7 | 106.1 | 3.85 | 2.2 | 102.8 | 3.92 | 2.2 | 104.4 |
| STD6 | 1.88 | 1.80 | 5.5 | 95.9 | 1.84 | 9.2 | 97.7 | 1.82 | 1.3 | 96.8 |
| STD7 | 0.938 | 0.930 | 1.2 | 99.2 | 0.936 | 1.8 | 99.8 | 0.933 | 0.4 | 99.5 |
| STD8 | 0.469 | 0.514 | 0.5 | 109.5 | 0.457 | 2.7 | 97.4 | 0.485 | 8.3 | 103.5 |
| STD9 | 0.234 | 0.222 | 8.9 | 94.9 | 0.247 | 5.7 | 105.6 | 0.235 | 7.6 | 100.3 |
| STD10 | 0.117 | 0.116 | 28.4 | 99.0 | 0.127 | 6.5 | 108.4 | 0.121 | 6.4 | 103.7 |
| STD11 | 0.059 | 0.066 | 26.6 | 111.0 | 0.050 | 46.6 | 85.3 | 0.058 | 18.5 | 98.2 |
| ULOQ | 40 | 40.8 | 3.1 | 102.0 | 39.9 | 4.0 | 99.8 | 40.4 | 1.5 | 100.9 |
| High-VS | 20 | 19.9 | 2.9 | 99.4 | 19.5 | 3.9 | 97.3 | 19.7 | 1.5 | 98.3 |
| Mid VS | 2.5 | 2.42 | 2.3 | 96.9 | 2.62 | 2.8 | 104.7 | 2.52 | 5.5 | 100.8 |
| Low-VS | 0.625 | 0.703 | 4.8 | 112.5 | 0.602 | 0.8 | 96.3 | 0.652 | 11.0 | 104.4 |
| LLOQ-2 | 0.200 | 0.248 | 9.0 | 124.1 | 0.192 | 0.4 | 96.1 | 0.220 | 18.0 | 110.1 |
| LLOQ-1 | 0.156 | 0.192 | 13.8 | 122.8 | 0.178 | 2.3 | 113.8 | 0.185 | 5.3 | 118.3 |

TABLE 18

Process Stability for Endogenous samples

| Time Sample | 0 hours | | 2 hours | | Mean | |
|---|---|---|---|---|---|---|
| | Average Conc (ng/mL) | % CV | Average Conc (ng/mL) | % CV | Conc (ng/mL) | % CV |
| End-1 | 5.84 | 2.6 | 5.83 | 10.4 | 5.83 | 0.2 |
| End-2 | 0.835 | 28.5 | 0.785 | 3.3 | 0.810 | 4.4 |

Assay plates were read on a Gyrolab XP workstation and were analyzed using the GyroLab evaluator software and imported into Microsoft Excel 2007 or later version.

Descriptive statistics, such as arithmetic means, standard deviations, precision (% CV) were determined using Microsoft Excel 2007 or later version.

There was one plan amendment that allowed for the masking of a maximum of two of the nine non-zero standard points if the CV was greater than 25%.

There were two Deviations noted during the study.

Deviation #226

The clock and thermometer were not documented on the Supplemental Bioanalytical Worksheets for Runs 1 through 8. The deviation had no impact on the study data as all runs performed as expected and the time and temperature were noted by using the calibrated clock and thermometer in the laboratory.

Deviation #237

Requirement: Biotin ALXN1007 (capture antibody) is prepared at 100 ug/mL in PBST and added to the PCR plate according to the Gyro Lab loading list.

Deviation: Biotin ALXN1007 (capture antibody) was prepared at 89 ug/mL in PBST and added to the PCR plate according to the Gyro Lab loading list.

The deviation occurred on Run 1. The deviation was that the Biotin ALXN was prepared at 89 ug/ml and not 100 ug/mL as specified in the General Assay procedure section. A typographical error was discovered on the supplemental worksheet by the analyst during the analysis for run 1 where a previous stock concentration of the ALXN1007 was noted on the worksheet and used for the calculation. The analyst made the correction to the worksheet and documented the correction. Upon peer review of the run it was discovered and documented that the correction was calculated incorrectly.

The deviation had no impact on the study as the Run is noted as failed and data was not used for analysis in the study. The run failed to meet target criteria due to high CV's associated with the standard curve.

TABLE 19

Assay Procedure

| Step | Procedure | Initial |
|---|---|---|
| 1 | Add 20 uL of DynaBead coupled N19/8 to the appropriate wells of a PCR 96 well plate according to the sample plate map. | |
| 2 | Add 10 uL of the samples according to the sample plate map. | |
| 3 | Seal the plate with a foil seal and mix vigorously on plate shaker for a minimum of 1 hr at room temperature. Start time:_ End time:_ Start temp:_° C. End temp:_° C. | |
| 4 | Start the Gyrolab Server and Gyrolab Client software and set up the run. Use PBST as Wash Station Solution 1 and pH 11 Wash Station Solution 2. | |
| 5 | Print the Gyrolab Control Loading List. | |
| 6 | Prime the Gyros Instrument 2 times. | |
| 7 | Remove CD and place at room temperature for at least 30 min before starting the run. Start time:_ End time:_ Start temp:_° C. End temp:_° C. | |
| 8 | Prepare STD curve, blank, and QC's as described in the supplemental worksheet. | |
| 9 | Dilute STD Curve 2 fold (MRD2) into 1M NaCl, 0.5% Tween in PCR plate (i.e. 10 μL into 10 μL) according to Loading List. | |
| 10 | Dilute QCs 2 fold (MRD2) into 1M NaCl, 0.5% Tween into PCR plate according to the loading list. | |
| 11 | Place plate from Step 3 on magnet for a minimum of 2 minutes to separate beads. Start time:_ End time:_ | |
| 12 | Remove 10 uL of sample from the plate from step 3 being careful not to disturb the beads and add according to the loading list map from step 3. | |
| 13 | Prepare capture and detection antibodies as described in the supplemental worksheet. | |
| 14 | Load plates and CD(s) into instrument when instructed by software. | |
| 15 | Run the assay. | |
| 16 | Unload plates and CD(s) from instrument when instructed by software after run has completed. | |
| 17 | If this was the last run of the day, place the instrument in Standby. | |

TABLE 20

Assay Procedure (Bead Preparation)

| Step | Procedure | Initial |
|---|---|---|
| 1 | Remove Dynabead bottle from refrigerated storage and vortex vigorously for at least 30 seconds to get beads in solution | |
| 2 | Pipette 1.0 mL of resuspended beads from the storage bottle into a 1.5 mL microcentrifuge tube | |
| 3 | Place microcentrifuge tube into magnet slot and wait a minimum of 2 minutes for beads to be pulled out of solution Start time:_ End time:_ Start temp:_° C. End temp:_° C. | |
| 4 | Using a P1000 pipette, gently remove buffer from tube without disturbing magnetized beads | |
| 5 | Pipette 1.0 mL of PBS into tube and vortex vigorously to get beads into solution | |
| 6 | Place microcentrifuge tube into magnet slot and wait a minimum of 2 minutes for beads to be pulled out of solution Start time:_ End time:_ Start temp:_° C. End temp:_° C. | |
| 7 | Using a P1000 pipette, gently remove buffer from tube without disturbing magnetized beads | |
| 8 | Pipette 1.0 mL of PBS into tube and vortex vigorously to get beads into solution | |
| 9 | Place microcentrifuge tube into magnet slot and wait a minimum of 2 minutes for beads to be pulled out of solution Start time:_ End time:_ Start temp:_° C.End temp:_° C. | |
| 10 | Using a P1000 pipette, gently remove buffer from tube without disturbing magnetized beads | |
| 11 | Pipette 1.0 mL of PBS into tube and vortex vigorously to get beads into solution | |
| 12 | Place microcentrifuge tube into magnet slot and wait a minimum of 2 minutes for beads to be pulled out of solution Start time:_ End time:_ Start temp:_° C. End temp:_° C. | |
| 13 | After removal of the third wash, resuspend beads with 1.0 mL of N19/8 Ab at a concentration of 20 μg/mL in PBS | |
| 14 | Vortex vigorously to get beads into solution and place on tube rack mixer for a minimum of one hour at room temperature Start time:_ End time:_ Start temp:_° C. End temp:_° C. | |
| 15 | Place microcentrifuge tube into magnet slot and wait for a minimum of 2 minutes for beads to be pulled out of solution Start time:_ End time:_ Start temp:_° C. End temp:_° C. | |
| 16 | Using a P1000 pipette, gently remove buffer from tube without disturbing magnetized beads | |
| 17 | Pipette 1.0 mL of PBS into tube and vortex vigorously to get beads into solution | |

TABLE 20-continued

Assay Procedure (Bead Preparation)

| Step | Procedure | Initial |
|---|---|---|
| 18 | Place microcentrifuge tube into magnet slot and wait a minimum of 2 minutes for beads to be pulled out of solution<br>Start time:_ End time:_<br>Start temp:_° C. End temp:_° C. | |
| 19 | Using a P1000 pipette, gently remove buffer from tube without disturbing magnetized beads | |
| 20 | Pipette 1.0 mL of PBS into tube and vortex vigorously to get beads into solution | |
| 21 | Place microcentrifuge tube into magnet slot and wait a minimum of 2 minutes for beads to be pulled out of solution<br>Start time:_ End time:_<br>Start temp:_° C. End temp:_° C. | |
| 22 | Using a P1000 pipette, gently remove buffer from tube without disturbing magnetized beads | |
| 23 | Pipette 1.0 mL of PBS into tube and vortex vigorously to get beads into solution | |
| 24 | Place microcentrifuge tube into magnet slot and wait a minimum of 2 minutes for beads to be pulled out of solution<br>Start time:_ End time:_<br>Start temp:_° C. End temp:_° C. | |
| 25 | Using a P1000 pipette, gently remove buffer from tube without disturbing magnetized beads | |
| 26 | Pipette 1.0 mL of 1M NaCl, 0.5% Tween into tube and vortex vigorously to get beads into solution | |
| 27 | Vortex vigorously to get beads into solution | |
| 28 | Assign an RP # and set the expiration date to 1 week from date of preparation | |
| 29 | Label tube and store at 4° C. for future use | |

TABLE 21

CRITICAL REAGENTS
The following reagents are used from the specified providers and lots.

| Reagent | Source | Batch/Lot Number |
|---|---|---|
| Biotin ALXN1007 capture (7.7 mg/mL) | Alexion | S426-15 |
| Human C5a des Arg Ref std (5 µg/mL) * | BioAgilytix | RP14Oct16TM01 |
| Alexa647 labeled anti C5a antibody (1.38 mg/mL) | Hycult BioTech | 20574M0716-A |
| Individual 2 (IND-2) | BioReclamation | BRH1240216 |
| Individual 11 (IND-11) | BioReclamation | BRH1240225 |

* Working stock of C5a desArg Purified Human Complement Protein

TABLE 22

ADDITIONAL REAGENTS

| Reagent | Source | Batch/Lot Number |
|---|---|---|
| PCR Plates | Thermo Scientific | 00437243 |
| Gyro Lab Wash Buffer (PBS + 0.01% Tween20) | BioAgilytix Labs | RP16Jan17TM01 |
| Assay Diluent (1M NaCl + 0.5% Tween20) | BioAgilytix Labs | RP16Jan17TM02 |
| Rexxip F | Gyros Labs | 0003539 |
| Rexxip AN | Gyros Labs | 0003680<br>0003500 |
| 1 × PBS + 0.01% Tween (PBST) | BioAgilytix Labs | RP16Jan17TM01 |
| Gyrolab Wash Buffer pH 11 | Gyros | RP16Jan17TM03<br>RP23Jan17TM01<br>RP27Jan17TM01 |
| 20% Ethanol (Standby Solution) | BioAgilytix Labs | RP28Nov16BN02 |
| Dynabead My One Streptavidin C1 Dyna Beads | Life Technologies | 00429328<br>00411637 |
| Gyrolab Bioaffy 1000 CD | Gyros | 0003490 |
| Biotinylated n19/8 | Alexion | S388-95 |

OTHER EMBODIMENTS

The foregoing description discloses only exemplary embodiments of the invention.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the appended claims. Thus, while only certain features of the invention have been illustrated and described, many modifications and changes will occur to those skilled in the art. It is therefore to be understood that the appended claims are intended to cover all such modifications and changes as fall within the true spirit of the invention.

TABLE 23

SOME NUCLEIC ACID AND AMINO ACID SEQUENCES

```
SEQ ID NO: 1 (coded protein disclosed as SEQ ID NO: 2)
gat atc cag atg acc cag tcc ccg tcc tcc ctg tcc gcc tct gtg ggc    48
Asp Ile Gln Met Thr Gln Ser Pro Ser Ser Leu Ser Ala Ser Val Gly
1               5                   10                  15 gat agg gtc acc atc acc tgc ggc gcc agc gaa aac atc tat ggc gcg    96
Asp Arg Val Thr Ile Thr Cys Gly Ala Ser Glu Asn Ile Tyr Gly Ala
            20                  25                  30 ctg aac tgg tat caa cag aaa ccc ggg aaa gct ccg aag ctt ctg att   144
Leu Asn Trp Tyr Gln Gln Lys Pro Gly Lys Ala Pro Lys Leu Leu Ile
                35                  40                  45 tac ggt gcg acg aac ctg gca gat gga gtc cct tct cgc ttc tct gga   192
Tyr Gly Ala Thr Asn Leu Ala Asp Gly Val Pro Ser Arg Phe Ser Gly
            50                  55                  60
```

TABLE 23-continued

SOME NUCLEIC ACID AND AMINO ACID SEQUENCES

```
tcc ggc tcc gga acg gat ttc act ctg acc atc agc agt ctg cag cct    240
Ser Gly Ser Gly Thr Asp Phe Thr Leu Thr Ile Ser Ser Leu Gln Pro
65                  70                  75                  80 gaa gac ttc gct acg tat tac tgt cag aac gtt tta aat act ccg ttg    288
Glu Asp Phe Ala Thr Tyr Tyr Cys Gln Asn Val Leu Asn Thr Pro Leu
                85                  90                  95 act ttc gga cag ggt acc aag gtg gaa ata aaa cgt act ggc ggt ggt    336
Thr Phe Gly Gln Gly Thr Lys Val Glu Ile Lys Arg Thr Gly Gly Gly
            100                 105                 110 ggt tct ggt ggc ggt gga tct ggt ggt ggc ggt tct caa gtc caa ctg    384
Gly Ser Gly Gly Gly Gly Ser Gly Gly Gly Gly Ser Gln Val Gln Leu
        115                 120                 125 gtg caa tcc ggc gcc gag gtc aag aag cca ggg gcc tca gtc aaa gtg    432
Val Gln Ser Gly Ala Glu Val Lys Lys Pro Gly Ala Ser Val Lys Val
    130                 135                 140 tcc tgt aaa gct agc ggc tat att ttt tct aat tat tgg att caa tgg    480
Ser Cys Lys Ala Ser Gly Tyr Ile Phe Ser Asn Tyr Trp Ile Gln Trp
145                 150                 155                 160 gtg cgt cag gcc ccc ggg cag ggc ctg gaa tgg atg ggt gag atc tta    528
Val Arg Gln Ala Pro Gly Gln Gly Leu Glu Trp Met Gly Glu Ile Leu
                165                 170                 175 ccg ggc tct ggt agc acc gaa tat acc gaa aat ttt aaa gac cgt gtt    576
Pro Gly Ser Gly Ser Thr Glu Tyr Thr Glu Asn Phe Lys Asp Arg Val
            180                 185                 190 act atg acg cgt gac act tcg act agt aca gta tac atg gag ctc tcc    624
Thr Met Thr Arg Asp Thr Ser Thr Ser Thr Val Tyr Met Glu Leu Ser
        195                 200                 205 agc ctg cga tcg gag gac acg gcc gtc tat tat tgc gcg cgt tat ttt    672
Ser Leu Arg Ser Glu Asp Thr Ala Val Tyr Tyr Cys Ala Arg Tyr Phe
    210                 215                 220 ttt ggt tct agc ccg aat tgg tat ttt gat gtt tgg ggt caa gga acc    720
Phe Gly Ser Ser Pro Asn Trp Tyr Phe Asp Val Trp Gly Gln Gly Thr
225                 230                 235                 240 ctg gtc act gtc tcg agc tga                                        741
Leu Val Thr Val Ser Ser
                245

SEQ ID NO: 2
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
                20                  25                  30

Leu Asn Trp Tyr Gln Gln Lys Pro Gly Lys Ala Pro Lys Leu Leu Ile
            35                  40                  45

Tyr Gly Ala Thr Asn Leu Ala Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Gly Gly Gly
            100                 105                 110

Gly Ser Gly Gly Gly Gly Ser Gly Gly Gly Gly Ser Gln Val Gln Leu
        115                 120                 125

Val Gln Ser Gly Ala Glu Val Lys Lys Pro Gly Ala Ser Val Lys Val
    130                 135                 140

Ser Cys Lys Ala Ser Gly Tyr Ile Phe Ser Asn Tyr Trp Ile Gln Trp
145                 150                 155                 160
```

TABLE 23-continued

SOME NUCLEIC ACID AND AMINO ACID SEQUENCES

Val Arg Gln Ala Pro Gly Gln Gly Leu Glu Trp Met Gly Glu Ile Leu
                165                 170                 175

Pro Gly Ser Gly Ser Thr Glu Tyr Thr Glu Asn Phe Lys Asp Arg Val
                180                 185                 190

Thr Met Thr Arg Asp Thr Ser Thr Ser Thr Val Tyr Met Glu Leu Ser
                195                 200                 205

Ser Leu Arg Ser Glu Asp Thr Ala Val Tyr Tyr Cys Ala Arg Tyr Phe
        210                 215                 220

Phe Gly Ser Ser Pro Asn Trp Tyr Phe Asp Val Trp Gly Gln Gly Thr
225                 230                 235                 240

Leu Val Thr Val Ser Ser
                245

SEQ ID NO: 3
Gly Gly Gly Gly Ser Gly Gly Gly Gly Ser Gly Gly Gly Gly Ser

SEQ ID NO: 4
Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
                20                  25                  30

Val Gly Ala Ser Glu Asn Ile Val Ile Gln Val Tyr Gly Tyr Thr Glu
                35                  40                  45

Ala Phe Asp Ala Thr Ile Ser Ile Lys Ser Tyr Pro Asp Lys Lys Phe
        50                  55                  60

Ser Tyr Ser Ser Gly His Val His Leu Ser Ser Glu Asn Lys Phe Gln
65                  70                  75                  80

Asn Ser Ala Ile Leu Thr Ile Gln Pro Lys Gln Leu Pro Gly Gly Gln
                85                  90                  95

Asn Pro Val Ser Tyr Val Tyr Leu Glu Val Val Ser Lys His Phe Ser
                100                 105                 110

Lys Ser Lys Arg Met Pro Ile Thr Tyr Asp Asn Gly Phe Leu Phe Ile
            115                 120                 125

His Thr Asp Lys Pro Val Tyr Thr Pro Asp Gln Ser Val Lys Val Arg
        130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Val Asp Met Val Glu Glu
                165                 170                 175

Ile Asp His Ile Gly Ile Ile Ser Phe Pro Asp Phe Lys Ile Pro Ser
            180                 185                 190

Asn Pro Arg Tyr Gly Met Trp Thr Ile Lys Ala Lys Tyr Lys Glu Asp
            195                 200                 205

Phe Ser Thr Thr Gly Thr Ala Tyr Phe Glu Val Lys Glu Tyr Val Leu
        210                 215                 220

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
                245                 250                 255

Asn Lys Val Val Thr Glu Ala Asp Val Tyr Ile Thr Phe Gly Ile Arg
                260                 265                 270

Glu Asp Leu Lys Asp Asp Gln Lys Glu Met Met Gln Thr Ala Met Gln
        275                 280                 285

Asn Thr Met Leu Ile Asn Gly Ile Ala Gln Val Thr Phe Asp Ser Glu
        290                 295                 300

TABLE 23-continued

SOME NUCLEIC ACID AND AMINO ACID SEQUENCES

Thr Ala Val Lys Glu Leu Ser Tyr Tyr Ser Leu Glu Asp Leu Asn Asn
305             310             315             320

Lys Tyr Leu Tyr Ile Ala Val Thr Val Ile Glu Ser Thr Gly Gly Phe
                325             330             335

Ser Glu Glu Ala Glu Ile Pro Gly Ile Lys Tyr Val Leu Ser Pro Tyr
            340             345             350

Lys Leu Asn Leu Val Ala Thr Pro Leu Phe Leu Lys Pro Gly Ile Pro
            355             360             365

Tyr Pro Ile Lys Val Gln Val Lys Asp Ser Leu Asp Gln Leu Val Gly
        370             375             380

Gly Val Pro Val Ile Leu Asn Ala Gln Thr Ile Asp Val Asn Gln Glu
385             390             395             400

Thr Ser Asp Leu Asp Pro Ser Lys Ser Val Thr Arg Val Asp Asp Gly
                405             410             415

Val Ala Ser Phe Val Leu Asn Leu Pro Ser Gly Val Thr Val Leu Glu
                420             425             430

Phe Asn Val Lys Thr Asp Ala Pro Asp Leu Pro Glu Glu Asn Gln Ala
            435             440             445

Arg Glu Gly Tyr Arg Ala Ile Ala Tyr Ser Ser Leu Ser Gln Ser Tyr
    450             455             460

Leu Tyr Ile Asp Trp Thr Asp Asn His Lys Ala Leu Leu Val Gly Glu
465             470             475             480

His Leu Asn Ile Ile Val Thr Pro Lys Ser Pro Tyr Ile Asp Lys Ile
                485             490             495

Thr His Tyr Asn Tyr Leu Ile Leu Ser Lys Gly Lys Ile Ile His Phe
            500             505             510

Gly Thr Arg Glu Lys Phe Ser Asp Ala Ser Tyr Gln Ser Ile Asn Ile
    515             520             525

Pro Val Thr Gln Asn Met Val Pro Ser Ser Arg Leu Leu Val Tyr Tyr
    530             535             540

Ile Val Thr Gly Glu Gln Thr Ala Glu Leu Val Ser Asp Ser Val Trp
545             550             555             560

Leu Asn Ile Glu Glu Lys Cys Gly Asn Gln Leu Gln Val His Leu Ser
            565             570             575

Pro Asp Ala Asp Ala Tyr Ser Pro Gly Gln Thr Val Ser Leu Asn Met
            580             585             590

Ala Thr Gly Met Asp Ser Trp Val Ala Leu Ala Ala Val Asp Ser Ala
    595             600             605

Val Tyr Gly Val Gln Arg Gly Ala Lys Lys Pro Leu Glu Arg Val Phe
    610             615             620

Gln Phe Leu Glu Lys Ser Asp Leu Gly Cys Gly Ala Gly Gly Gly Leu
625             630             635             640

Asn Asn Ala Asn Val Phe His Leu Ala Gly Leu Thr Phe Leu Thr Asn
                645             650             655

Ala Asn Ala Asp Asp Ser Gln Glu Asn Asp Glu Pro Cys Lys Glu Ile
                660             665             670

Leu Arg Pro Arg Arg Thr Leu Gln Lys Lys Ile Glu Glu Ile Ala Ala
            675             680             685

Lys Tyr Lys His Ser Val Val Lys Lys Cys Cys Tyr Asp Gly Ala Cys
            690             695             700

Val Asn Asn Asp Glu Thr Cys Glu Gln Arg Ala Ala Arg Ile Ser Leu
705             710             715             720

TABLE 23-continued

SOME NUCLEIC ACID AND AMINO ACID SEQUENCES

Gly Pro Arg Cys Ile Lys Ala Phe Thr Glu Cys Cys Val Val Ala Ser
            725                 730                 735

Gln Leu Arg Ala Asn Ile Ser His Lys Asp Met Gln Leu Gly Arg Leu
            740                 745                 750

His Met Lys Thr Leu Leu Pro Val Ser Lys Pro Glu Ile Arg Ser Tyr
            755                 760                 765

Phe Pro Glu Ser Trp Leu Trp Glu Val His Leu Val Pro Arg Arg Lys
            770                 775                 780

Gln Leu Gln Phe Ala Leu Pro Asp Ser Leu Thr Thr Trp Glu Ile Gln
785                 790                 795                 800

Gly Ile Gly Ile Ser Asn Thr Gly Ile Cys Val Ala Asp Thr Val Lys
            805                 810                 815

Ala Lys Val Phe Lys Asp Val Phe Leu Glu Met Asn Ile Pro Tyr Ser
            820                 825                 830

Val Val Arg Gly Glu Gln Ile Gln Leu Lys Gly Thr Val Tyr Asn Tyr
            835                 840                 845

Arg Thr Ser Gly Met Gln Phe Cys Val Lys Met Ser Ala Val Glu Gly
850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Gly Ser Ser His Leu Val
            885                 890                 895

Thr Phe Thr Val Leu Pro Leu Glu Ile Gly Leu His Asn Ile Asn Phe
            900                 905                 910

Ser Leu Glu Thr Trp Phe Gly Lys Glu Ile Leu Val Lys Thr Leu Arg
            915                 920                 925

Val Val Pro Glu Gly Val Lys Arg Glu Ser Tyr Ser Gly Val Thr Leu
            930                 935                 940

Asp Pro Arg Gly Ile Tyr Gly Thr Ile Ser Arg Arg Lys Glu Phe Pro
945                 950                 955                 960

Tyr Arg Ile Pro Leu Asp Leu Val Pro Lys Thr Glu Ile Lys Arg Ile
            965                 970                 975

Leu Ser Val Lys Gly Leu Leu Val Gly Glu Ile Leu Ser Ala Val Leu
            980                 985                 990

Ser Gln Glu Gly Ile Asn Ile Leu Thr His Leu Pro Lys Gly Ser Ala
            995                 1000                1005

Glu Ala Glu Leu Met Ser Val Val Pro Val Phe Tyr Val Phe His Tyr
            1010                1015                1020

Tyr Leu Glu Thr Gly Asn His Trp Asn Ile Phe His Ser Asp Pro
            1025                1030                1035

Leu Ile Glu Lys Gln Lys Leu Lys Lys Lys Leu Lys Glu Gly Met
            1040                1045                1050

Leu Ser Ile Met Ser Tyr Arg Asn Ala Asp Tyr Ser Tyr Ser Val
            1055                1060                1065

Trp Lys Gly Gly Ser Ala Ser Thr Trp Leu Thr Ala Phe Ala Leu
            1070                1075                1080

Arg Val Leu Gly Gln Val Asn Lys Tyr Val Glu Gln Asn Gln Asn
            1085                1090                1095

Ser Ile Cys Asn Ser Leu Leu Trp Leu Val Glu Asn Tyr Gln Leu
            1100                1105                1110

Asp Asn Gly Ser Phe Lys Glu Asn Ser Gln Tyr Gln Pro Ile Lys
            1115                1120                1125

TABLE 23-continued

SOME NUCLEIC ACID AND AMINO ACID SEQUENCES

```
Leu Gln Gly Thr Leu Pro Val Glu Ala Arg Glu Asn Ser Leu Tyr
    1130                1135                1140

Leu Thr Ala Phe Thr Val Ile Gly Ile Arg Lys Ala Phe Asp Ile
    1145                1150                1155

Cys Pro Leu Val Lys Ile Asp Thr Ala Leu Ile Lys Ala Asp Asn
    1160                1165                1170

Phe Leu Leu Glu Asn Thr Leu Pro Ala Gln Ser Thr Phe Thr Leu
    1175                1180                1185

Ala Ile Ser Ala Tyr Ala Leu Ser Leu Gly Asp Lys Thr His Pro
    1190                1195                1200

Gln Phe Arg Ser Ile Val Ser Ala Leu Lys Arg Glu Ala Leu Val
    1205                1210                1215

Lys Gly Asn Pro Pro Ile Tyr Arg Phe Trp Lys Asp Asn Leu Gln
    1220                1225                1230

His Lys Asp Ser Ser Val Pro Asn Thr Gly Thr Ala Arg Met Val
    1235                1240                1245

Glu Thr Thr Ala Tyr Ala Leu Leu Thr Ser Leu Asn Leu Lys Asp
    1250                1255                1260

Ile Asn Tyr Val Asn Pro Val Ile Lys Trp Leu Ser Glu Glu Gln
    1265                1270                1275

Arg Tyr Gly Gly Gly Phe Tyr Ser Thr Gln Asp Thr Ile Asn Ala
    1280                1285                1290

Ile Glu Gly Leu Thr Glu Tyr Ser Leu Leu Val Lys Gln Leu Arg
    1295                1300                1305

Leu Ser Met Asp Ile Asp Val Ser Tyr Lys His Lys Gly Ala Leu
    1310                1315                1320

His Asn Tyr Lys Met Thr Asp Lys Asn Phe Leu Gly Arg Pro Val
    1325                1330                1335

Glu Val Leu Leu Asn Asp Asp Leu Ile Val Ser Thr Gly Phe Gly
    1340                1345                1350

Ser Gly Leu Ala Thr Val His Val Thr Thr Val His Lys Thr
    1355                1360                1365

Ser Thr Ser Glu Glu Val Cys Ser Phe Tyr Leu Lys Ile Asp Thr
    1370                1375                1380

Gln Asp Ile Glu Ala Ser His Tyr Arg Gly Tyr Gly Asn Ser Asp
    1385                1390                1395

Tyr Lys Arg Ile Val Ala Cys Ala Ser Tyr Lys Pro Ser Arg Glu
    1400                1405                1410

Glu Ser Ser Ser Gly Ser Ser His Ala Val Met Asp Ile Ser Leu
    1415                1420                1425

Pro Thr Gly Ile Ser Ala Asn Glu Glu Asp Leu Lys Ala Leu Val
    1430                1435                1440

Glu Gly Val Asp Gln Leu Phe Thr Asp Tyr Gln Ile Lys Asp Gly
    1445                1450                1455

His Val Ile Leu Gln Leu Asn Ser Ile Pro Ser Ser Asp Phe Leu
    1460                1465                1470

Cys Val Arg Phe Arg Ile Phe Glu Leu Phe Glu Val Gly Phe Leu
    1475                1480                1485

Ser Pro Ala Thr Phe Thr Val Tyr Glu Tyr His Arg Pro Asp Lys
    1490                1495                1500

Gln Cys Thr Met Phe Tyr Ser Thr Ser Asn Ile Lys Ile Gln Lys
    1505                1510                1515
```

TABLE 23-continued

SOME NUCLEIC ACID AND AMINO ACID SEQUENCES

Val Cys Glu Gly Ala Ala Cys Lys Cys Val Glu Ala Asp Cys Gly
         1520                1525                1530

Gln Met Gln Glu Glu Leu Asp Leu Thr Ile Ser Ala Glu Thr Arg
    1535                1540                1545

Lys Gln Thr Ala Cys Lys Pro Glu Ile Ala Tyr Ala Tyr Lys Val
1550                1555                1560

Ser Ile Thr Ser Ile Thr Val Glu Asn Val Phe Val Lys Tyr Lys
    1565                1570                1575

Ala Thr Leu Leu Asp Ile Tyr Lys Thr Gly Glu Ala Val Ala Glu
        1580                1585                1590

Lys Asp Ser Glu Ile Thr Phe Ile Lys Lys Val Thr Cys Thr Asn
    1595                1600                1605

Ala Glu Leu Val Lys Gly Arg Gln Tyr Leu Ile Met Gly Lys Glu
        1610                1615                1620

Ala Leu Gln Ile Lys Tyr Asn Phe Ser Phe Arg Tyr Ile Tyr Pro
    1625                1630                1635

Leu Asp Ser Leu Thr Trp Ile Glu Tyr Trp Pro Arg Asp Thr Thr
        1640                1645                1650

Cys Ser Ser Cys Gln Ala Phe Leu Ala Asn Leu Asp Glu Phe Ala
    1655                1660                1665

Glu Asp Ile Phe Leu Asn Gly Cys
        1670                1675

SEQ ID NO: 5
QVQLVQSGAEVKKPGASVKVSCKASGYIFSNYWIQWVRQAPGQGLEWMGEILPGSGSTEYTENFKDRVTMTRDTSTS
TVYMELSSLRSEDTAVYYCARYFFGSSPNWYEDVWGQGTLVTVSSASTKGPSVFPLAPCSRSTSESTAALGCLVKDY
FPEPVTVSWNSGALTSGVHTFPAVLQSSGLYSLSSVVTVPSSNFGTQTYTCNVDHKPSNTKVDKTVERKCCVECPPC
PAPPVAGPSVFLFPPKPKDTLMISRTPEVTCVVVDVSQEDPEVQFNWYVDGVEVHNAKTKPREEQFNSTYRVVSVLT
VLHQDWLNGKEYKCKVSNKGLPSSIEKTISKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEALHNHYTQKSLSLSLGK

SEQ ID NO: 6
DIQMTQSPSSLSASVGDRVTITCGASENIYGALNWYQQKPGKAPKLLIYGATNLADGVPSRFSGSGSGTDFTLTISS
LQPEDFATYYCQNVLNTPLTFGQGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC

SEQ ID NO: 7 heavy chain (gv4) (448 amino acids)
QVQLVQSGAEVKKPGASVKVSCKASGHIFSNYWIQWVRQAPGQGLEWMGEILPGSGHTEYTENFKDRVTMTRDTSTS
TVYMELSSLRSEDTAVYYCARYFFGSSPNWYEDVWGQGTLVTVSSASTKGPSVFPLAPCSRSTSESTAALGCLVKDY
FPEPVTVSWNSGALTSGVHTFPAVLQSSGLYSLSSVVTVPSSNFGTQTYTCNVDHKPSNTKVDKTVERKCCVECPPC
PAPPVAGPSVFLFPPKPKDTLMISRTPEVTCVVVDVSQEDPEVQFNWYVDGVEVHNAKTKPREEQFNSTYRVVSVLT
VLHQDWLNGKEYKCKVSNKGLPSSIEKTISKAKGQPREPQVYTLPPSQEEMTKNQVSLTCLVKGFYPSDIAVEWESN
GQPENNYKTTPPVLDSDGSFFLYSRLTVDKSRWQEGNVFSCSVLHEALHSHYTQKSLSLSLGK SEQ ID NO: 8 light chain: (Kappa) (214 amino acids)
DIQMTQSPSSLSASVGDRVTITCGASENIYGALNWYQQKPGKAPKLLIYGATNLADGVPSRFSGSGSGTDFTLTISS
LQPEDFATYYCQNVLNTPLTFGQGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC

SEQ ID NO: 9 GYIFSNYWIQ

SEQ ID NO: 10 EILPGSGSTEYTENFKD

SEQ ID NO: 11 YFFGSSPNWYFDV

SEQ ID NO: 12 GASENIYGALN

SEQ ID NO: 13 GATNLAD

SEQ ID NO: 14 QNVLNTPLT

SEQ ID NO: 15
QVQLVQSGAEVKKPGASVKVSCKASGYIFSNYWIQWVRQAPGQGLEWMGEILPGSGSTEYTENFKDRVTMTRDTSTS
TVYMELSSLRSEDTAVYYCARYFFGSSPNWYEDVWGQGTLVTVSS

TABLE 23-continued

SOME NUCLEIC ACID AND AMINO ACID SEQUENCES

SEQ ID NO: 16
DIQMTQSPSSLSASVGDRVTITCGASENIYGALNWYQQKPGKAPKLLIYGATNLADGVPSRFSGSGSGTDFTLTISS
LQPEDFATYYCQNVLNTPLTFGQGTKVEIK

SEQ ID NO: 23 amino acid sequence of heavy chain constant region of eculizumab
ASTKGPSVFPLAPCSRSTSESTAALGCLVKDYFPEPVTVSWNSGALTSGVH
TFPAVLQSSGLYSLSSVVTVPSSNFGTQTYTCNVDHKPSNTKVDKTVERKC
CVECPPCPAPPVAGPSVFLFPPKPKDTLMISRTPEVTCVVVDVSQEDPEVQF
NWYVDGVEVHNAKTKPREEQFNSTYRVVSVLTVLHQDWLNGKEYKCKV
SNKGLPSSIEKTISKAKGQPREPQVYTLPPSQEEMTKNQVSLTCLVKGFYPS
DIAVEWESNGQPENNYKTTPPVLDSDGSFFLYSRLTVDKSRWQEGNVFSCS
VMHEALHNHYTQKSLSLSLGK SEQ ID NO: 24 amino acid sequence of heavy chain variable region of BNJ441
antibody
QVQLVQSGAEVKKPGASVKVSCKASGHIFSNYWIQWVRQAPGQGLEW
MGEILPGSGHTEYTENFKDRVTMTRDTSTSTVYMELSSLRSEDTAVYYC
ARYFFGSSPNWYFDVWGQGTLVTVSS SEQ ID NO: 25 amino acid sequence of heavy chain constant region of BNJ441
antibody
ASTKGPSVFPLAPCSRSTSESTAALGCLVKDYFPEPVTVSWNSGALTSGV
HTFPAVLQSSGLYSLSSVVTVPSSNFGTQTYTCNVDHKPSNTKVDKTVER
KCCVECPPCPAPPVAGPSVFLFPPKPKDTLMISRTPEVTCVVVDVSQEDPE
VQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVKG
FYPSDIAVEWESNGQPENNYKTTPPVLDSDGSFFLYSRLTVDKSRWQEGN
VFSCSVLHEALHSHYTQKSLSLSLGK SEQ ID NO: 26 amino acid sequence of IgG2 heavy chain constant region variant
comprising YTE substitutions
ASTKGPSVFPLAPCSRSTSESTAALGCLVKDYFPEPVTVSWNSGALTSGVH
TFPAVLQSSGLYSLSSVVTVTSSNFGTQTYTCNVDHKPSNTKVDKTVERKC
CVECPPCPAPPVAGPSVFLEPPKPKDTLYITREPEVTCVVVDVSHEDPEVQF
NWYVDGMEVHNAKTKPREEQFNSTERVVSVLTVVHQDWLNGKEYKCKV
SNKGLPAPIEKTISKTKGQPREPQVYTLPPSREEMTKNQVSLTCLVKGFYP
SDIAVEWESNGQPENNYKTTPPMLDSDGSFFLYSKLTVDKSRWQQGNVF
SCSVMHEALHNHYTQKSLSLSPGK SEQ ID NO: 27 amino acid sequence of entire heavy chain of eculizumab variant
comprising heavy chain constant region depicted in SEQ ID NO: 26 (above)
QVQLVQSGAEVKKPGASVKVSCKASGYIFSNYWIQWVRQAPGQGLEWM
GEILPGSGSTEYTENFKDRVTMTRDTSTSTVYMELSSLRSEDTAVYYCAR
YFFGSSPNWYFDVWGQGTLVTVSSASTKGPSVFPLAPCSRSTSESTAALG
CLVKDYFPEPVTVSWNSGALTSGVHTFPAVLQSSGLYSLSSVVTVTSSNF
GTQTYTCNVDHKPSNTKVDKTVERKCCVECPPCPAPPVAGPSVFLFPPKP
KDTLYITREPEVTCVVVDVSHEDPEVQFNWYVDGMEVHNAKTKPREEQ
FNSTFRVVSVLTVVHQDWLNGKEYKCKVSNKGLPAPIEKTISKTKGQPRE
PQVYTLPPSREEMTKNQVSLTCLVKGFYPSDIAVEWESNGQPENNYKTTP
PMLDSDGSFFLYSKLTVDKSRWQQGNVESCSVMHEALHNHYTQKSLSLS
PGK SEQ ID NO: 28 amino acid sequence of light chain CDR1 of eculizumab (as defined
under Kabat definition) with glycine to histidine substitution at position 8
relative to SEQ ID NO: 12 GASENIYHALN SEQ ID NO: 29 depicts amino acid sequence of heavy chain CDR2 of eculizumab in
which serine at position 8 relative to SEQ ID NO: 10 is substituted with histidine
EILPGSGHTEYTENFKD SEQ ID NO: 30 amino acid sequence of "FLAG" tag DYKDDDDK SEQ ID NO: 31 polyhistidine sequence commonly used as antigenic tag.
HHHHHH SEQ ID NO: 32 amino acid sequence of hemagglutinin tag. YPYDVPDYA SEQ ID NO: 33 amino acid sequence of heavy chain CDR1 of eculizumab in which
tyrosine at position 2 (relative to SEQ ID NO: 9) is substituted with histidine
GHIFSNYWIQ

What is claimed is:

1. A method of quantitating unbound human C5 complement protein (C5) in a sample obtained from a human patient before and after treatment with an anti-C5 antibody, wherein the method comprises:

performing separate assays on the pre-treatment sample and post-treatment sample, wherein each of the assays respectively comprises:
a. binding biotinylated anti-C5 capture antibody to streptavidin coated particles; wherein said biotinylated anti-C5 capture antibody is added by capillary action to a compact disc (CD) comprising columns with the streptavidin coated particles; wherein said CD is subjected to centrifugal force inside an instrument, thus driving the biotinylated anti-C5 capture antibody to the streptavidin coated particles in the columns;
b. capturing the unbound C5 in the pre-treatment sample or the post-treatment sample; wherein the pre-treatment sample or the post-treatment sample is added to the CD by capillary action; wherein said CD is subjected to centrifugal force inside the instrument, thus driving the pre-treatment sample or the post-treatment sample to the biotinylated anti-C5 capture antibody bound to the streptavidin coated particles in the columns;
c. detecting the captured C5; wherein an Alexa Fluor labeled anti-C5 detection antibody is added to the CD by capillary action, wherein said anti-C5 detection antibody binds C5 at a different epitope from the epitope bound by the capture antibody;
wherein said CD is subjected to centrifugal force inside the instrument, thus driving the detection antibody to the C5 bound to the capture antibody bound to the streptavidin coated particles in the columns; and
d. quantitating the captured C5 using laser-induced fluorescence detection, wherein the pre-treatment sample is diluted at least 1:20 and post-treatment sample is diluted about 1:2.

2. The method of claim 1, further comprising calculating the concentration or amount of C5 antibody by comparing data obtained from step d. to a standard curve prepared from known amounts of C5 added to a C5 depleted sample.

3. The method of claim 1, further comprising priming the compact disc two separate times with phosphate buffered saline wash solution.

4. The method of claim 1, wherein the Gyros Bioaffy 200 CD has a dynamic range between 0.015 µg/mL to 300 µg/mL for the anti-C5 antibody.

5. The method of claim 4, wherein the post-treatment sample is diluted by about a 1:30 dilution.

6. The method of claim 1, wherein the sample is a serum sample or plasma sample obtained from a human patient.

7. The method of claim 1, wherein the patient has been treated with an anti-C5 antibody.

8. The method of claim 7, wherein the patient has been treated with an antibody comprising:
(a) heavy chain CDR1, CDR2, CDR3 domains having the sequences of SEQ ID NOs: 9, 10, 11 and light chain CDR1, CDR2, and CDR3 domains having the sequences of SEQ ID NOs: 12, 13, and 14; or
(b) heavy chain CDR1, CDR2, CDR3 domains having the sequences of SEQ ID NOs: 28, 29, 11 and light chain CDR1, CDR2, and CDR3 domains having the sequences of SEQ ID NOs: 12, 13, and 14.

9. The method of claim 1, wherein the detection anti-C5 antibody is N19-8 (mouse anti-human C5 antibody).

* * * * *